United States Patent [19]

Kanda et al.

[11] Patent Number: 5,604,178
[45] Date of Patent: Feb. 18, 1997

[54] N-(SUBSTITUTED AMINO)PYRROLE DERIVATIVES, AND HERBICIDAL COMPOSITIONS

[75] Inventors: Yoichi Kanda; Hideo Arabori; Masato Arahira; Tsutomu Sato, all of Iwaki, Japan

[73] Assignee: Kureha Kagaku Kogyo K.K., Tokyo, Japan

[21] Appl. No.: 323,413

[22] Filed: Oct. 14, 1994

[30] Foreign Application Priority Data

Oct. 15, 1993 [JP] Japan .................................. 5-281889

[51] Int. Cl.$^6$ ......................... A01N 43/66; C07D 251/42
[52] U.S. Cl. ......................... 504/213; 544/198; 544/207; 544/209; 544/212
[58] Field of Search ............................. 504/213; 544/198, 544/207, 209, 212

[56] References Cited

U.S. PATENT DOCUMENTS

| | | | |
|---|---|---|---|
| 4,169,719 | 10/1979 | Levitt | 544/331 |
| 4,440,565 | 4/1984 | Willms et al. | 544/213 |
| 4,473,394 | 9/1984 | Budzinski et al. | 544/212 |
| 4,515,620 | 5/1985 | Bohner | 544/208 |
| 4,601,747 | 7/1986 | Willms et al. | 544/321 |
| 4,718,937 | 1/1988 | Willms et al. | 544/211 |

FOREIGN PATENT DOCUMENTS

| | | |
|---|---|---|
| 51466A2 | 5/1982 | European Pat. Off. . |
| 98569A2 | 7/1983 | Germany . |
| 2015503 | 9/1979 | United Kingdom . |
| 2110689 | 6/1983 | United Kingdom . |
| WO93/24482 | 12/1993 | WIPO . |

*Primary Examiner*—John M. Ford
*Attorney, Agent, or Firm*—Lowe, Price, LeBlanc & Becker

[57] ABSTRACT

This invention is to provide an N-(substituted amino)pyrrole derivative represented by the formula (I): which is used as an effective ingredient of herbicidal compositions:

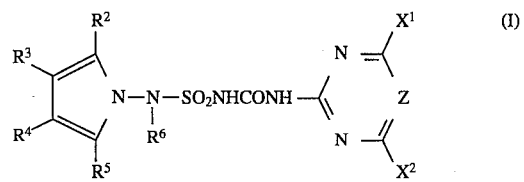

wherein $R^2$, $R^3$, $R^4$ and $R^5$ is independently hydrogen atom, halogen atom, $C_1$–$C_4$ alkyl group, ($C_1$–$C_4$ alkyl)carbonyl group, ($C_3$–$C_6$ cycloalkyl) carbonyl group, ($C_1$–$C_4$ haloalkyl)carbonyl group, ($C_3$–$C_5$ alkenyl)carbonyl group, benzoyl group which may be substituted with 1–3 halogen atoms and/or $C_1$–$C_4$ alkyl groups, N,N-[(di-$C_1$–$C_4$ alkyl)amino]carbonyl group, ($C_1$–$C_4$ alkoxy)carbonyl group, etc., $X^1$ and $X^2$ are independently hydrogen atom, halogen atom, $C_1$–$C_4$ alkyl group, $C_1$–$C_4$ alkoxy group, etc., and Z is nitrogen atom or CH.

7 Claims, No Drawings

N-(SUBSTITUTED AMINO)PYRROLE DERIVATIVES, AND HERBICIDAL COMPOSITIONS

BACKGROUND OF THE INVENTION

1. Field of the Invention

The present invention relates to N-(substituted amino)pyrrole derivatives, production process thereof, and herbicidal compositions containing the derivatives as active ingredients.

2. Description of the Related Art

Regarding herbicidal compounds having an (azinylureylene)sulfonyl group such as a {[(pyrimidin-2-yl- or 1,3,5-triazin-2-yl)aminocarbonyl]aminosulfonyl} group, a variety of compounds has heretofore been reported. For example, there are following reports regarding atoms to which an (azinylureylene)sulfonyl group is attached.

U.S. Pat. No. 4,169,719: Carbon atoms in a nonsubstituted of substituted benzene ring.

EP-A-51466: α-Carbon atom in the unsubstituted of substituted toluene.

U.S. Pat. No. 4,473,394: Carbon atom in the unsubstituted of substituted pyrrole ring.

GB 2,015,503 and EP-A-98569: Oxygen atom of hydroxyl group in unsubstituted of substituted phenols.

U.S. Pat. No. 4,440,565: Oxygen atom of hydroxyl group in unsubstituted of substituted alcohols.

U.S. Pat. No. 4,601,747 and U.S. Pat. No. 4,718,937: Nitrogen atom of the alkanesulfonamide group or alkoxyamino group.

U.S. Pat. No. 4,515,620: Nitrogen atom of the amino group in substituted anilines or 1-aminoindanes.

GB 2,110,689: Nitrogen atom in the ring of pyrrolidine, piperidine, morpholine,thiomorpholine or 1,3-thiazolidine.

Among herbicidal compounds described in the above patent publications, compounds having an (azinylureylene)sulfonyl group such as a {[(pyrimidin-2-yl- or 1,3,5-triazin-2-yl)aminocarbonyl]aminosulfonyl} group on a nitrogen atom of the nitrogen containing heterocyclic ring have been known (GB 2,110,689), but compounds having an (azinylureylene)sulfonyl group which is attached to a nitrogen atom of the pyrrole ring through another nitrogen atom have not been known.

By the way, there have conventionally been strong demands for herbicides capable of exhibiting reliable herbicidal activity even at such low-application dosages as bringing about the advantage of reducing the amount present in the environnment, herbicides capable of exhibiting selectivity between crops and weeds irrespective of variations in environmental conditions, herbicides free from crop injury to the second crop in double cropping, etc. The present invention has been completed with a view toward meeting such demands.

The present inventors have found that compounds having an (azinylureylene)sulfonyl group which bonds to a nitrogen atom of pyrrole ring through another nitrogen atom have excellent herbicidal activity, leading to the completion of the present invention.

SUMMARY OF THE INVENTION

Therefore, an object of the present invention is to provide novel compounds which show excellent herbicidal activity, to provide a preparation process thereof, to provide novel herbicidal compositions containing one or more of the derivatives as active ingredients, and to intermediate compounds thereof.

The present invention has the following constructive features.

In the first aspect of the invention, there is thus provided an N-(substituted amino)pyrrole derivative represented by the formula (I):

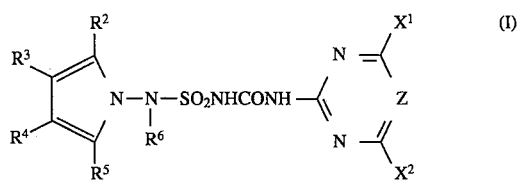

wherein $R^2$, $R^3$, $R^4$ and $R^5$ is independently hydrogen atom, halogen atom, $C_1$–$C_4$ alkyl group, $C_1$–$C_5$ haloalkyl group, $C_2$–$C_5$ alkoxyalkyl group, $C_3$–$C_5$ alkenyl group, $C_3$–$C_5$ haloalkenyl group, $C_3$–$C_5$ alkynyl group, phenyl group which may be substituted with 1–3 halogen atoms and/or $C_1$–$C_4$ alkyl groups, $C_7$–$C_9$ aralkyl group which may be substituted with 1–3 halogen atoms and/or $C_1$–$C_4$ alkyl groups, ($C_1$–$C_4$ alkyl)carbonyl group, ($C_2$–$C_5$ alkoxyalkyl) carbonyl group, ($C_3$–$C_6$ cycloalkyl)carbonyl group, ($C_1$–$C_4$ haloalkyl)carbonyl group, ($C_3$–$C_5$ alkenyl)carbonyl group, benzoyl group which may be substituted with 1–3 halogen atoms and/or $C_1$–$C_4$ alkyl groups, ($C_7$–$C_9$ aralkyl)carbonyl group which may be substituted with 1–3 halogen atoms and/or $C_1$–$C_4$ alkyl groups, carbamoyl group, N-($C_1$–$C_4$ alkyl)aminocarbonyl group, N,N-[(di-$C_1$–$C_4$ alkyl)amino] carbonyl group, carboxyl group, ($C_1$–$C_4$ alkoxy)carbonyl group, ($C_1$–$C_4$ haloalkoxy)carbonyl group, ($C_2$–$C_5$ alkoxyalkoxy)carbonyl group, ($C_3$–$C_5$ alkenyloxy)carbonyl group, ($C_3$–$C_5$ haloalkenyloxy)carbonyl group or ($C_3$–$C_5$ alkynyloxy)carbonyl group;

$R^6$ is hydrogen atom, $C_1$–$C_5$ alkyl group, $C_1$–$C_5$ haloalkyl group, $C_2$–$C_5$ alkoxyalkyl group, $C_3$–$C_5$ alkenyl group, $C_3$–$C_5$ haloalkenyl group, $C_3$–$C_5$ alkynyl group or $C_7$–$C_9$ aralkyl group which may be substituted with 1–3 halogen atoms and/or $C_1$–$C_4$ alkyl groups;

$X^1$ and $X^2$ are independently hydrogen atom, halogen atom, $C_1$–$C_4$ alkyl group, $C_1$–$C_4$ alkoxy group, $C_1$–$C_4$ alkylthio group, $C_1$–$C_4$ haloalkyl group, $C_1$–$C_4$ haloalkoxy group, $C_1$–$C_4$ haloalkylthio group, $C_2$–$C_4$ alkoxyalkyl group, $C_2$–$C_4$ thioalkoxyalkyl group or $NR^7R^8$, wherein $R^7$ and $R^8$ are independently hydrogen atom, $C_1$–$C_4$ alkyl group or $C_1$–$C_4$ alkoxy group; and Z is nitrogen atom or CH.

In the second aspect of the invention, there is provided a process for preparation of the above N-(substituted amino)pyrrole derivative represented by the formula (I), which comprises reacting an N-aminopyrrole derivative of the forumula (II) with an (azinylureylene)sulfonyl halide of the formula (III) according to the following reaction formula:

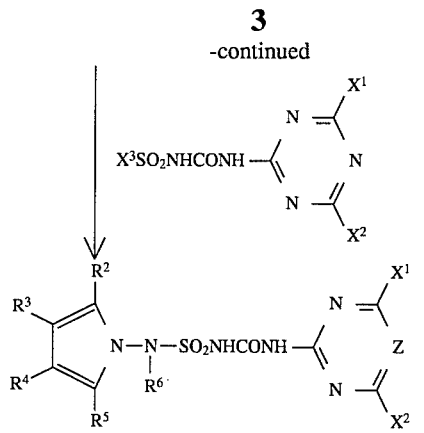

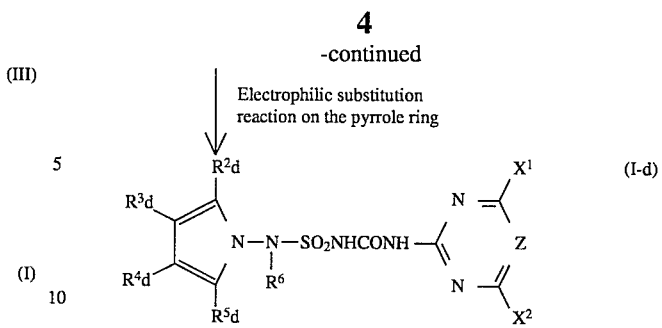

wherein $R^2$–$R^6$, $X^1$, $X^2$ and Z have each the same meaning as defined above and $X^3$ is halogen atom.

In the third aspect of the invention, there is provided a process for preparation of an N-(substituted amino)pyrrole derivative represented by the formula (I-b), which comprises reacting an N-(substituted amino)pyrrole derivative of the forumula (I-a) with a compound represented by the formula (VI) in the presence of a base to replace the hydrogen atom on the N-amino group with $R^1$ according to the following reaction formula:

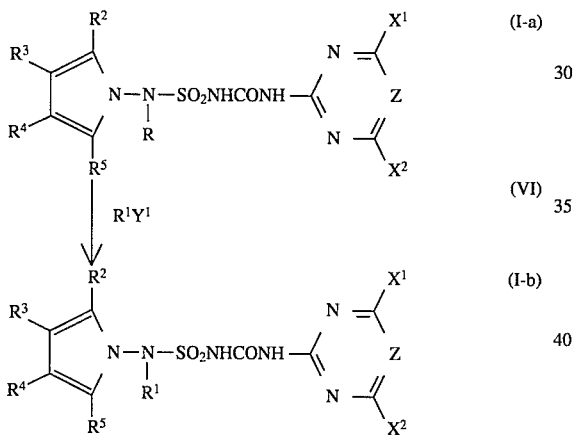

wherein $R^2$–$R^5$, $X^1$, $X^2$ and Z have each the same meaning as defined above and $R^1$ is $C_1$–$C_5$ alkyl group, $C_1$–$C_5$ haloalkyl group, $C_2$–$C_5$ alkoxyalkyl group, $C_3$–$C_5$ alkenyl group, $C_3$–$C_5$ haloalkenyl group, $C_3$–$C_5$ alkynyl group or $C_7$–$C_9$ aralkyl group which may be substituted with 1–3 halogen atoms and/or $C_1$–$C_4$ alkyl groups, and $Y^1$ is halogen atom or $OSO_2OR^1$.

In the fourth aspect of the invention, there is provided a process for preparation of an N-(substituted amino)pyrrole derivative of the formula (I-d), which comprises introducing a substituent into the pyrrole ring of N-(substituted amino)pyrrole derivative of the forumula (I-c) by an electrophilic substitution reaction of the hydrogen atom according to the following reaction formula:

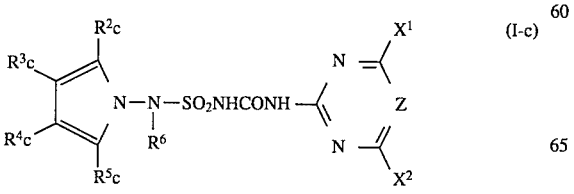

wherein $R^6$, $X^1$, $X^2$ and Z have each the same meaning as defined above, one of $R^2c$–$R^5c$ is hydrogen atom and the others thereof are independently hydrogen atom, halogen atom, $C_1$–$C_4$ alkyl group, $C_1$–$C_5$ haloalkyl group, $C_2$–$C_5$ alkoxyalkyl group, $C_3$–$C_5$ alkenyl group, $C_3$–$C_5$ haloalkenyl group, $C_3$–$C_5$ alkynyl group, phenyl group which may be substituted with 1–3 halogen atoms and/or $C_1$–$C_4$ alkyl groups, $C_7$–$C_9$ aralkyl group which may be substituted with 1–3 halogen atoms and/or $C_1$–$C_4$ alkyl groups, ($C_1$–$C_4$ alkyl)carbonyl group, ($C_2$–$C_5$ alkoxyalkyl)carbonyl group, ($C_3$–$C_6$ cycloalkyl)carbonyl group, ($C_1$–$C_4$ haloalkyl)carbonyl group, ($C_3$–$C_5$ alkenyl)carbonyl group, benzoyl group which may be substituted with 1–3 halogen atoms and/or $C_1$–$C_4$ alkyl groups, ($C_7$–$C_9$ aralkyl)carbonyl group which may be substituted with 1–3 halogen atoms and/or $C_1$–$C_4$ alkyl groups, carbamoyl group, N-($C_1$–$C_4$ alkyl)aminocarbonyl group, N,N-[(di-$C_1$–$C_4$ alkyl)amino]carbonyl group, carboxyl group, ($C_1$–$C_4$ alkoxy)carbonyl group, ($C_1$–$C_4$ haloalkoxy)carbonyl group, ($C_2$–$C_5$ alkoxyalkoxy)carbonyl group, ($C_3$–$C_5$ alkenyloxy)carbonyl group, ($C_3$–$C_5$ haloalkenyloxy)carbonyl group or ($C_3$–$C_5$ alkynyloxy)carbonyl group; one of $R^2d$–$R^5d$ is a substituent for the hydrogen atom which denotes halogen atom, $C_1$–$C_4$ alkyl group, $C_1$–$C_5$ haloalkyl group, $C_2$–$C_5$ alkoxyalkyl group, $C_3$–$C_5$ alkenyl group, $C_3$–$C_5$ haloalkenyl group, $C_3$–$C_5$ alkynyl group, phenyl group which may be substituted with 1–3 halogen atoms and/or $C_1$–$C_4$ alkyl groups, $C_7$–$C_9$ aralkyl group which may be substituted with 1–3 halogen atoms and/or $C_1$–$C_4$ alkyl groups, ($C_1$–$C_4$ alkyl)carbonyl group, ($C_2$–$C_5$ alkoxyalkyl)carbonyl group, ($C_3$–$C_6$ cycloalkyl)carbonyl group, ($C_1$–$C_4$ haloalkyl)carbonyl group, ($C_3$–$C_5$ alkenyl)carbonyl group, benzoyl group which may be substituted with 1–3 halogen atoms and/or $C_1$–$C_4$ alkyl groups, ($C_7$–$C_9$ aralkyl)carbonyl group which may be substituted with 1–3 halogen atoms and/or $C_1$–$C_4$ alkyl groups, carbamoyl group, N-($C_1$–$C_4$ alkyl)aminocarbonyl groups, N,N-[(di-$C_1$–$C_4$ alkyl)amino]carbonyl group, carboxyl group, ($C_1$–$C_4$ alkoxy)carbonyl group, ($C_1$–$C_4$ haloalkoxy)carbonyl group, ($C_2$–$C_5$ alkoxyalkoxy)carbonyl group, ($C_3$–$C_5$ alkenyloxy)carbonyl group, ($C_3$–$C_5$ haloalkenyloxy)carbonyl group or ($C_3$–$C_5$ alkynyloxy)carbonyl group;

and the others of $R^2d$–$R^5d$ are independently hydrogen atom, halogen atom, $C_1$–$C_4$ alkyl group, $C_1$–$C_5$ haloalkyl group, $C_2$–$C_5$ alkoxyalkyl group, $C_3$–$C_5$ alkenyl group, $C_3$–$C_5$ haloalkenyl group, $C_3$–$C_5$ alkynyl group, phenyl group which may be substituted with 1–3 halogen atoms and/or $C_1$–$C_4$ alkyl groups, $C_7$–$C_9$ aralkyl group which may be substituted with 1–3 halogen atoms and/or $C_1$–$C_4$ alkyl groups, ($C_1$–$C_4$ alkyl)carbonyl group, ($C_2$–$C_5$ alkoxyalkyl)carbonyl group, ($C_3$–$C_6$ cycloalkyl)carbonyl group, ($C_1$–$C_4$ haloalkyl)carbonyl group, ($C_3$–$C_5$ alkenyl)carbonyl group, benzoyl group which may be substituted with 1–3 halogen atoms and/or $C_1$–$C_4$ alkyl groups, ($C_7$–$C_9$ aralkyl)carbonyl group which may be substituted with 1–3 halogen atoms and/or $C_1$–$C_4$ alkyl groups, carbamoyl group, N-($C_1$–$C_4$ alkyl)aminocarbonyl group, N,N-[(di-$C_1$–$C_4$ alkyl)amino]carbonyl group, carboxyl group, ($C_1$–$C_4$ alkoxy)carbonyl group, ($C_1$–$C_4$ haloalkoxy)carbonyl group, ($C_2$–$C_5$ alkoxyalkoxy)carbonyl group, ($C_3$–$C_5$ alkenyloxy)carbonyl group, ($C_3$–$C_5$ haloalkenyloxy)carbonyl group or ($C_3$–$C_5$ alkynyloxy)carbonyl group.

In the fifth aspect of the invention, there is provided an N-aminopyrrole derivative of the formula (II-p) which is an intermediate for production of the N-(substituted amino)pyrrole derivative of the above forumula (I);

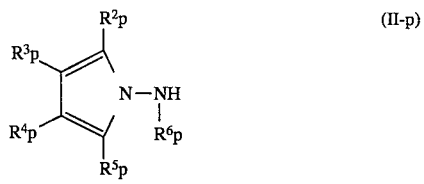

(II-p)

wherein $R^2p$, $R^3p$, $R^4p$ and $R^5p$ are independently hydrogen atom, halogen atom, $C_1$–$C_4$ alkyl group, $C_1$–$C_5$ haloalkyl group, $C_2$–$C_5$ alkoxyalkyl group, $C_3$–$C_5$ alkenyl group, $C_3$–$C_5$ haloalkenyl group, $C_3$–$C_5$ alkynyl group, phenyl group which may be substituted with 1–3 halogen atoms and/or $C_1$–$C_4$ alkyl groups, $C_7$–$C_9$ aralkyl group which may be substituted with 1–3 halogen atoms and/or $C_1$–$C_4$ alkyl groups, ($C_1$–$C_4$ alkyl)carbonyl group, ($C_2$–$C_5$ alkoxyalkyl) carbonyl group, ($C_3$–$C_6$ cycloalkyl)carbonyl group, ($C_1$–$C_4$ haloalkyl)carbonyl group, ($C_3$–$C_5$ alkenyl)carbonyl group, benzoyl group which may be substituted with 1–3 halogen atoms and/or $C_1$–$C_4$ alkyl groups, ($C_7$–$C_9$ aralkyl)carbonyl group which may be substituted with 1–3 halogen atoms and/or $C_1$–$C_4$ alkyl groups, carbamoyl group, N-($C_1$–$C_4$ alkyl)aminocarbonyl group, N,N-[(di-$C_1$–$C_4$ alkyl)amino] carbonyl group, carboxyl group, ($C_1$–$C_4$ alkoxy)carbonyl group, ($C_1$–$C_4$ haloalkoxy)carbonyl group, ($C_2$–$C_5$ alkoxyalkoxy)carbonyl group, ($C_3$–$C_5$ alkenyloxy)carbonyl group, ($C_3$–$C_5$ haloalkenyloxy)carbonyl group or ($C_3$–$C_5$ alkynyloxy)carbonyl group; and $R^6p$ is hydrogen atom, $C_1$–$C_5$ alkyl group, $C_1$–$C_5$ haloalkyl group, $C_2$–$C_5$ alkoxyalkyl group, $C_3$–$C_5$ alkenyl group, $C_3$–$C_5$ haloalkenyl group, $C_3$–$C_5$ alkynyl group or $C_7$–$C_9$ aralkyl group which may be substituted with 1–3 halogen atoms and/or $C_1$–$C_4$ alkyl groups;

exclusive of the compound in which $R^2p$–$R^6p$ each is hydrogen atom and the compound in which $R^2p$ and $R^5p$ are each methyl group and $R^3p$, $R^4p$ and $R^6p$ are each hydrogen atom.

In the sixth aspect of the invention, there is provided an N-(1H-pyrrol-1-yl)phthalimide derivative of the formula (IX-q) which is an intermediate for production of an N-aminopyrrole derivative of the above forumula (II-p);

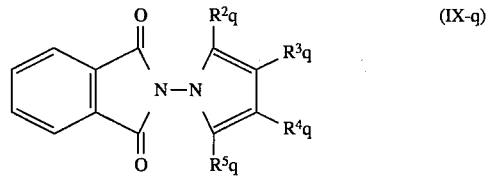

(IX-q)

wherein $R^2q$, $R^3q$, $R^4q$ and $R^5q$ are independently hydrogen atom, halogen atom, $C_1$–$C_4$ alkyl group, $C_1$–$C_5$ haloalkyl group, $C_2$–$C_5$ alkoxyalkyl group, $C_3$–$C_5$ alkenyl group, $C_3$–$C_5$ haloalkenyl group, $C_3$–$C_5$ alkynyl group, phenyl group which may be substituted with 1–3 halogen atoms and/or $C_1$–$C_4$ alkyl groups, $C_7$–$C_9$ aralkyl group which may be substituted with 1–3 halogen atoms and/or $C_1$–$C_4$ alkyl groups, ($C_1$–$C_4$ alkyl)carbonyl group, ($C_2$–$C_5$ alkoxyalkyl) carbonyl group, ($C_3$–$C_6$ cycloalkyl)carbonyl group, ($C_1$–$C_4$ haloalkyl)carbonyl group, ($C_3$–$C_5$ alkenyl)carbonyl group, benzoyl group which may be substituted with 1–3 halogen atoms and/or $C_1$–$C_4$ alkyl groups, ($C_7$–$C_9$ aralkyl)carbonyl group which may be substituted with 1–3 halogen atoms and/or $C_1$–$C_4$ alkyl groups, carbamoyl group, N-($C_1$–$C_4$ alkyl)aminocarbonyl group, N,N-[(di-$C_1$–$C_4$ alkyl)amino] carbonyl group, carboxyl group, ($C_1$–$C_4$ alkoxy)carbonyl group, ($C_1$–$C_4$ haloalkoxy)carbonyl group, ($C_2$–$C_5$ alkoxyalkoxy)carbonyl group, ($C_3$–$C_5$ alkenyloxy)carbonyl group, ($C_3$–$C_5$ haloalkenyloxy)carbonyl group, ($C_3$–$C_5$ alkynyloxy)carbonyl group or chlorocarbonyl group;

exclusive of the compound in which $R^2q$–$R^5q$ are each hydrogen atom and the compound in which $R^2q$ and $R^5q$ are each methyl group and $R^3q$ and $R^4q$ are each hydrogen atom.

In the seventh aspect of the invention, there is provided a herbicidal composition which comprises a herbicidally effective amount of an N-(substituted amino)pyrrole derivative of the formula (I) as an active ingredient.

In the above definition of $X^1$, $X^2$ and z in the pyrimidine ring and the triazine ring, it is preferred that $X^1$ and $X^2$ are independently halogen atom, $C_1$–$C_2$ alkyl group, $C_1$–$C_2$ fluoroalkyl group, $C_1$–$C_2$ fluoroalkoxy group, $C_2$–$C_4$ alkoxyalkyl group or $NR^7R^8$ wherein $R^7$ and $R^8$ are independently hydrogen atom or $C_1$–$C_2$ alkyl group.

In the above definition, the fluoroalkyl group or the fluoroalkoxy group means haloalkyl group or haloalkoxy group in which halogen atoms are fluorine atoms.

DETAILED DESCRIPTION OF PREFERRED EMBODIMENTS

In the following description, $R^1$–$R^6$, $X^1$, $X^2$, $X^3$, Z, $Y^1$, $R^2c$–$R^5c$, $R^2d$–$R^5d$, $R^2p$–$R^6p$ and $R^2q$–$R^5q$ in the formulas have each the same meaning as defined above.

In the following, chemicals used for a series of reactions according to the present invention are exemplified.

Examples of diluent include the following compounds.

Water; organic acids such as formic acid, acetic acid, propioninc acid, and the like; hydrocarbons such as benzene, toluene, xylene, petroleum ether, pentane, hexane, heptane, and the like; halogenated hydrocarbons such as methylene chloride, chloroform, carbon tetrachloride, and the like; alcohols such as methanol, ethanol, isopropanol, t-butanol, and the like; ethers such as diethyl ether, dimethoxyethane, diisopropyl ether, tetrahydrofuran, dioxane, and the like. Other examples are acetonitrile, acetone, ethyl acetate, acetic anhydride, pyridine, dimethylformamide, dimethylacetamide, 1-methyl-2-pyrrolidinone and dimethylfulfoxide, etc.

The reactions may be carried out in the presence of a base or an acid in addition to the above described diluent. Examples of the base include the following compounds.

Carbonates of alkali mental such as sodium carbonate, potassium carbonate, and the like; carbonates of alkaline earth metal such as magnesium carbonate, calcium carbonate, barium carbonate, and the like; hydroxides of alkali metal such as sodium hydroxide, potassium hydroxide, and the like; hydroxides of alkaline earth metal such as magnesium hydroxide, calcium hydroxide, and the like; alkali metals such as lithium, sodium, potassium and the like;

alkaline earth metals such as magnesium, and the like; alkali metal alkoxides such as sodium methoxide, sodium ethoxide, potasium t-butoxide, and the like; alkali metal hydrides such as sodium hydride, potassium hydride, and the like; alkaline earth metal hydrides such as calcium hydride, and the like; organometallic compounds of alkali metal such as methyllithium, ethyllithium, n-butyllithium, phenyllithium, and the like; organic Grignard reagents such as methylmagnesium idodide, ethylmagnesium bromide, n-butylmagnesium bromide, and the like; organocopper compounds prepared from an organometallic compound of alkalki metal or a Grignard reagent with a cuprous salt; alkali metal amides such as lithium diisopropylamide, and the like; ammonium hydroxides, the nitrogen atom of which is unsubstituted of substituted with alkyl groups or aralkyl groups, such as aqueous ammonia, benzyltrimethylammonium hydroxide, tetramethylammonium hydroxide, and the like; and organic amines such as methylamine, ethylamine, n-propylamine, benzylamine, ethanolamine, dimethylamine, benzylmethylamine, dibenzylamide, triethylamine, triethanolamine, pyridine, and the like.

Examples of the acid include inorganic acids such as hydrochloric acid, hydrobromic acid, hydroiodic acid, perchloric acid, sulfuric acid, and the like, organic acids such as formic acid, acetic acid, butyric acid, p-toluenesulfonic acid, and the like; and Lewis acids such as boron trifluoride, alminium chloride, zinc chloride, and the like.

Specific examples of the derivatives of the above formula (I) according to the invention include those shown in Table 1 to Table 4.

TABLE 1

| No. | $R^2, R^3, R^4, R^5$ | $R^6$ | $X^1$ | $X^2$ | Z |
|---|---|---|---|---|---|
| I-1 | In I-1– | H | $CF_3$ | $OCH_3$ | CH |
| I-2 | I-134, | H | $CF_3$ | $OCHF_2$ | CH |
| I-3 |  | H | $CH(CH_3)_2$ | $OCH_3$ | CH |
| I-4 | $R^2 = H$ | H | $CH(OCH_3)_2$ | $CH_3$ | CH |
| I-5 | $R^3 = H$ | H | $CH_2F$ | $OCH_3$ | CH |
| I-6 | $R^4 = H$ | H | $CH_2F$ | $OCHF_2$ | CH |
| I-7 | $R^5 = H$ | H | $CH_2OCH_3$ | $CH_3$ | CH |
| I-8 |  | H | $CH_2OCH_3$ | $OCH_3$ | CH |
| I-9 |  | H | $CH_2OCH_3$ | $OCHF_2$ | CH |
| I-10 |  | H | $CH_3$ | $CF_3$ | CH |
| I-11 |  | H | $CH_3$ | $CH_3$ | CH |
| I-12 |  | H | $CH_3$ | Cl | CH |
| I-13 |  | H | $CH_3$ | F | CH |
| I-14 |  | H | $CH_3$ | H | CH |
| I-15 |  | H | $CH_3$ | $OC_2H_5$ | CH |
| I-16 |  | H | $CH_3$ | $OCF_2CHF_2$ | CH |
| I-17 |  | H | $CH_3$ | $OCF_2CHFCF_3$ | CH |
| I-18 |  | H | $CH_3$ | $OCH_2CF_3$ | CH |
| I-19 |  | H | $CH_3$ | $OCH_2CH_2F$ | CH |
| I-20 |  | H | $CH_3$ | $OCH_2CHF_2$ | CH |
| I-21 |  | H | $CH_3$ | $OCH_3$ | CH |
| I-22 |  | H | $CH_3$ | $OCHF_2$ | CH |
| I-23 |  | H | $CH_3$ | $SCH_3$ | CH |
| I-24 |  | H | $CHF_2$ | $CH_3$ | CH |
| I-25 |  | H | Cl | Cl | CH |
| I-26 |  | H | Cl | H | CH |
| I-27 |  | H | Cl | $N(CH_3)_2$ | CH |
| I-28 |  | H | Cl | $NH_2$ | CH |
| I-29 |  | H | Cl | $OC_2H_5$ | CH |
| I-30 |  | H | Cl | $OCF_2CHF_2$ | CH |
| I-31 |  | H | Cl | $OCF_2CHFCl$ | CH |
| I-32 |  | H | Cl | $OCH_3$ | CH |
| I-33 |  | H | Cl | $OCHF_2$ | CH |
| I-34 |  | H | $N(CH_3)_2$ | $OCF_2CHF_2$ | CH |
| I-35 |  | H | $N(CH_3)_2$ | $OCH_3$ | CH |
| I-36 |  | H | $N(CH_3)_2$ | $OCHF_2$ | CH |
| I-37 |  | H | $N(CH_3)_2$ | $SCHF_2$ | CH |
| I-38 |  | H | $N(CH_3)C_2H_5$ | $OCHF_2$ | CH |
| I-39 |  | H | $N(CH_3)OCH_3$ | $OCHF_2$ | CH |
| I-40 |  | H | $NH_2$ | $OCH_3$ | CH |
| I-41 |  | H | $NHCH_3$ | $OCH_3$ | CH |
| I-42 |  | H | $NHCH_3$ | $OCHF_2$ | CH |
| I-43 |  | H | $OC_2H_5$ | $OC_2H_5$ | CH |
| I-44 |  | H | $OCF_2CHF_2$ | $SCH_3$ | CH |
| I-45 |  | H | $OCH(CH_3)_2$ | $OCHF_2$ | CH |
| I-46 |  | H | $OCH_2CF_3$ | $OCH_3$ | CH |
| I-47 |  | H | $OCH_2CH_2F$ | $OCH_3$ | CH |
| I-48 |  | H | $OCH_2CHF_2$ | $OCH_3$ | CH |
| I-49 |  | H | $OCH_3$ | $OC_2H_5$ | CH |
| I-50 |  | H | $OCH_3$ | $OCF_2CHF_2$ | CH |
| I-51 |  | H | $OCH_3$ | $OCF_2CHFCF_3$ | CH |
| I-52 |  | H | $OCH_3$ | $OCH(CH_3)_2$ | CH |
| I-53 |  | H | $OCH_3$ | $OCH_3$ | CH |
| I-54 |  | H | $OCH_3$ | $SCH_3$ | CH |
| I-55 |  | H | $OCH_3$ | $SCHF_2$ | CH |
| I-56 |  | H | $OCHF_2$ | $OCH_2CF_3$ | CH |
| I-57 |  | H | $OCHF_2$ | $OCH_2CH_3$ | CH |
| I-58 |  | H | $OCHF_2$ | $OCH_3$ | CH |

TABLE 1-continued

| No. | $R^2, R^3, R^4, R^5$ | $R^6$ | $X^1$ | $X^2$ | Z |
|---|---|---|---|---|---|
| I-59 | | H | OCHF$_2$ | OCHF$_2$ | CH |
| I-60 | | H | OCHF$_2$ | SCH$_3$ | CH |
| I-61 | | H | C$_2$H$_5$ | OCH$_3$ | N |
| I-62 | | H | C$_2$H$_5$ | SCH$_3$ | N |
| I-63 | | H | CF$_3$ | OCH$_3$ | N |
| I-64 | | H | CH(CH$_3$)$_2$ | CH$_3$ | N |
| I-65 | | H | CH(CH$_3$)$_2$ | Cl | N |
| I-66 | | H | CH(CH$_3$)$_2$ | OCH$_3$ | N |
| I-67 | | H | CH(CH$_3$)$_2$ | SCH$_3$ | N |
| I-68 | | H | CH$_2$CF$_3$ | CH$_3$ | N |
| I-69 | | H | CH$_2$F | CH$_3$ | N |
| I-70 | | H | CH$_2$F | OCH$_3$ | N |
| I-71 | | H | CH$_2$OCH$_3$ | CH$_3$ | N |
| I-72 | | H | CH$_2$OCH$_3$ | OCH$_3$ | N |
| I-73 | | H | CH$_2$SCH$_3$ | CH$_3$ | N |
| I-74 | | H | CH$_2$SCH$_3$ | Cl | N |
| I-75 | | H | CH$_2$SCH$_3$ | OC$_2$H$_5$ | N |
| I-76 | | H | CH$_2$SCH$_3$ | OCH$_3$ | N |
| I-77 | | H | CH$_2$SCH$_3$ | SCH$_3$ | N |
| I-78 | | H | CH$_3$ | CF$_3$ | N |
| I-79 | | H | CH$_3$ | CH$_3$ | N |
| I-80 | | H | CH$_3$ | Cl | N |
| I-81 | | H | CH$_3$ | F | N |
| I-82 | | H | CH$_3$ | H | N |
| I-83 | | H | CH$_3$ | OCH$_2$CF$_3$ | N |
| I-84 | | H | CH$_3$ | OCH$_2$CH$_2$F | N |
| I-85 | | H | CH$_3$ | OCH$_2$CHF$_2$ | N |
| I-86 | | H | CH$_3$ | OCH$_3$ | N |
| I-87 | | H | CH$_3$ | SCH$_3$ | N |
| I-88 | | H | CH$_3$ | SCHF$_2$ | N |
| I-89 | | H | CHF$_2$ | CH$_3$ | N |
| I-90 | | H | CHF$_2$ | OCH$_3$ | N |
| I-91 | | H | Cl | Cl | N |
| I-92 | | H | Cl | OCH(CH$_3$)$_2$ | N |
| I-93 | | H | Cl | OCH$_2$CF$_3$ | N |
| I-94 | | H | Cl | OCH$_3$ | N |
| I-95 | | H | Cl | SCH$_3$ | N |
| I-96 | | H | F | OCH$_3$ | N |
| I-97 | | H | H | NH(CH$_3$) | N |
| I-98 | | H | N(CH$_3$)$_2$ | OCH$_3$ | N |
| I-99 | | H | N(CH$_3$)$_2$ | SCHF$_2$ | N |
| I-100 | | H | NHCH$_3$ | OCH$_3$ | N |
| I-101 | | H | OC$_2$H$_5$ | OC$_2$H$_5$ | N |
| I-102 | | H | OCF$_2$CHF$_2$ | SCH$_3$ | N |
| I-103 | | H | OCF$_2$CHFBr | SCH$_3$ | N |
| I-104 | | H | OCF$_2$CHFCF$_3$ | SCH$_3$ | N |
| I-105 | | H | OCH(CH$_3$)$_2$ | OCH$_3$ | N |
| I-106 | | H | OCH(CH$_3$)$_2$ | SCH$_3$ | N |
| I-107 | | H | OCH(CH$_3$)CH$_2$CH$_3$ | OCH$_3$ | N |
| I-108 | | H | OCH$_2$CF$_3$ | OCF$_2$CHF$_2$ | N |
| I-109 | | H | OCH$_2$CF$_3$ | OCH$_3$ | N |
| I-110 | | H | OCH$_2$CHF$_2$ | OCH$_3$ | N |
| I-111 | | H | OCH$_3$ | OC$_2$H$_5$ | N |
| I-112 | | H | OCH$_3$ | OCF$_2$CHF$_2$ | N |
| I-113 | | H | OCH$_3$ | OCF$_2$CHFBr | N |
| I-114 | | H | OCH$_3$ | OCF$_2$CHFCF$_3$ | N |
| I-115 | | H | OCH$_3$ | OCF$_2$CHFCl | N |
| I-116 | | H | OCH$_3$ | OCH$_3$ | N |
| I-117 | | H | OCH$_3$ | OCHF$_2$ | N |
| I-118 | | H | OCH$_3$ | SCH(CH$_3$)$_2$ | N |
| I-119 | | H | OCH$_3$ | SCH$_3$ | N |
| I-120 | | H | OCH$_3$ | SCHF$_2$ | N |
| I-121 | | CH$_3$ | CH$_3$ | CH$_3$ | CH |
| I-122 | | CH$_3$ | CH$_3$ | Cl | CH |
| I-123 | | CH$_3$ | CH$_3$ | OCH$_3$ | CH |
| I-124 | | CH$_3$ | Cl | Cl | CH |
| I-125 | | CH$_3$ | Cl | OCH$_3$ | CH |
| I-126 | | CH$_3$ | OCH$_3$ | OCH$_3$ | CH |
| I-127 | | CH$_3$ | CH$_3$ | CH$_3$ | N |
| I-128 | | CH$_3$ | CH$_3$ | Cl | N |
| I-129 | | CH$_3$ | CH$_3$ | OCH$_3$ | N |
| I-130 | | CH$_3$ | Cl | Cl | N |
| I-131 | | CH$_3$ | Cl | OCH$_3$ | N |
| I-132 | | CH$_3$ | N(CH$_3$)$_2$ | OCH$_3$ | N |
| I-133 | | CH$_3$ | OCH$_2$CH$_2$F | OCH$_3$ | N |
| I-134 | | CH$_3$ | OCH$_3$ | OCH$_3$ | N |
| I-135 | In I-135– | H | CF$_3$ | OCH$_3$ | CH |

TABLE 1-continued

| No. | $R^2, R^3, R^4, R^5$ | $R^6$ | $X^1$ | $X^2$ | Z |
|---|---|---|---|---|---|
| I-136 | I-268, | H | $CF_3$ | $OCHF_2$ | CH |
| I-137 | | H | $CH(CH_3)_2$ | $OCH_3$ | CH |
| I-138 | $R^2 = CH_3$ | H | $CH(OCH_3)_2$ | $CH_3$ | CH |
| I-139 | $R^3 = H$ | H | $CH_2F$ | $OCH_3$ | CH |
| I-140 | $R^4 = H$ | H | $CH_2F$ | $OCHF_2$ | CH |
| I-141 | $R^5 = CH_3$ | H | $CH_2OCH_3$ | $CH_3$ | CH |
| I-142 | | H | $CH_2OCH_3$ | $OCH_3$ | CH |
| I-143 | | H | $CH_2OCH_3$ | $OCHF_2$ | CH |
| I-144 | | H | $CH_3$ | $CF_3$ | CH |
| I-145 | | H | $CH_3$ | $CH_3$ | CH |
| I-146 | | H | $CH_3$ | Cl | CH |
| I-147 | | H | $CH_3$ | F | CH |
| I-148 | | H | $CH_3$ | H | CH |
| I-149 | | H | $CH_3$ | $OC_2H_5$ | CH |
| I-150 | | H | $CH_3$ | $OCF_2CHF_2$ | CH |
| I-151 | | H | $CH_3$ | $OCF_2CHFCF_3$ | CH |
| I-152 | | H | $CH_3$ | $OCH_2CF_3$ | CH |
| I-153 | | H | $CH_3$ | $OCH_2CH_2F$ | CH |
| I-154 | | H | $CH_3$ | $OCH_2CHF_2$ | CH |
| I-155 | | H | $CH_3$ | $OCH_3$ | CH |
| I-156 | | H | $CH_3$ | $OCHF_2$ | CH |
| I-157 | | H | $CH_3$ | $SCH_3$ | CH |
| I-158 | | H | $CHF_2$ | $CH_3$ | CH |
| I-159 | | H | Cl | Cl | CH |
| I-160 | | H | Cl | H | CH |
| I-161 | | H | Cl | $N(CH_3)_2$ | CH |
| I-162 | | H | Cl | $NH_2$ | CH |
| I-163 | | H | Cl | $OC_2H_5$ | CH |
| I-164 | | H | Cl | $OCF_2CHF_2$ | CH |
| I-165 | | H | Cl | $OCF_2CHFCl$ | CH |
| I-166 | | H | Cl | $OCH_3$ | CH |
| I-167 | | H | Cl | $OCHF_2$ | CH |
| I-168 | | H | $N(CH_3)_2$ | $OCF_2CHF_2$ | CH |
| I-169 | | H | $N(CH_3)_2$ | $OCH_3$ | CH |
| I-170 | | H | $N(CH_3)_2$ | $OCHF_2$ | CH |
| I-171 | | H | $N(CH_3)_2$ | $SCHF_2$ | CH |
| I-172 | | H | $N(CH_3)C_2H_5$ | $OCHF_2$ | CH |
| I-173 | | H | $N(CH_3)OCH_3$ | $OCHF_2$ | CH |
| I-174 | | H | $NH_2$ | $OCH_3$ | CH |
| I-175 | | H | $NHCH_3$ | $OCH_3$ | CH |
| I-176 | | H | $NHCH_3$ | $OCHF_2$ | CH |
| I-177 | | H | $OC_2H_5$ | $OC_2H_5$ | CH |
| I-178 | | H | $OCF_2CHF_2$ | $SCH_3$ | CH |
| I-179 | | H | $OCH(CH_3)_2$ | $OCHF_2$ | CH |
| I-180 | | H | $OCH_2CF_3$ | $OCH_3$ | CH |
| I-181 | | H | $OCH_2CH_2F$ | $OCH_3$ | CH |
| I-182 | | H | $OCH_2CHF_2$ | $OCH_3$ | CH |
| I-183 | | H | $OCH_3$ | $OC_2H_5$ | CH |
| I-184 | | H | $OCH_3$ | $OCF_2CHF_2$ | CH |
| I-185 | | H | $OCH_3$ | $OCF_2CHFCF_3$ | CH |
| I-186 | | H | $OCH_3$ | $OCH(CH_3)_2$ | CH |
| I-187 | | H | $OCH_3$ | $OCH_3$ | CH |
| I-188 | | H | $OCH_3$ | $SCH_3$ | CH |
| I-189 | | H | $OCH_3$ | $SCHF_2$ | CH |
| I-190 | | H | $OCHF_2$ | $OCH_2CF_3$ | CH |
| I-191 | | H | $OCHF_2$ | $OCH_2CH_3$ | CH |
| I-192 | | H | $OCHF_2$ | $OCH_3$ | CH |
| I-193 | | H | $OCHF_2$ | $OCHF_2$ | CH |
| I-194 | | H | $OCHF_2$ | $SCH_3$ | CH |
| I-195 | | H | $C_2H_5$ | $OCH_3$ | N |
| I-196 | | H | $C_2H_5$ | $SCH_3$ | N |
| I-197 | | H | $CF_3$ | $OCH_3$ | N |
| I-198 | | H | $CH(CH_3)_2$ | $CH_3$ | N |
| I-199 | | H | $CH(CH_3)_2$ | Cl | N |
| I-200 | | H | $CH(CH_3)_2$ | $OCH_3$ | N |
| I-201 | | H | $CH(CH_3)_2$ | $SCH_3$ | N |
| I-202 | | H | $CH_2CF_3$ | $CH_3$ | N |
| I-203 | | H | $CH_2F$ | $CH_3$ | N |
| I-204 | | H | $CH_2F$ | $OCH_3$ | N |
| I-205 | | H | $CH_2OCH_3$ | $CH_3$ | N |
| I-206 | | H | $CH_2OCH_3$ | $OCH_3$ | N |
| I-207 | | H | $CH_2SCH_3$ | $CH_3$ | N |
| I-208 | | H | $CH_2SCH_3$ | Cl | N |
| I-209 | | H | $CH_2SCH_3$ | $OC_2H_5$ | N |
| I-210 | | H | $CH_2SCH_3$ | $OCH_3$ | N |
| I-211 | | H | $CH_2SCH_3$ | $SCH_3$ | N |
| I-212 | | H | $CH_3$ | $CF_3$ | N |

TABLE 1-continued

| No. | R², R³, R⁴, R⁵ | R⁶ | X¹ | X² | Z |
|---|---|---|---|---|---|
| I-213 | | H | CH₃ | CH₃ | N |
| I-214 | | H | CH₃ | Cl | N |
| I-215 | | H | CH₃ | F | N |
| I-216 | | H | CH₃ | H | N |
| I-217 | | H | CH₃ | OCH₂CF₃ | N |
| I-218 | | H | CH₃ | OCH₂CH₂F | N |
| I-219 | | H | CH₃ | OCH₂CHF₂ | N |
| I-220 | | H | CH₃ | OCH₃ | N |
| I-221 | | H | CH₃ | SCH₃ | N |
| I-222 | | H | CH₃ | SCHF₂ | N |
| I-223 | | H | CHF₂ | CH₃ | N |
| I-224 | | H | CHF₂ | OCH₃ | N |
| I-225 | | H | Cl | Cl | N |
| I-226 | | H | Cl | OCH(CH₃)₂ | N |
| I-227 | | H | Cl | OCH₂CF₃ | N |
| I-228 | | H | Cl | OCH₃ | N |
| I-229 | | H | Cl | SCH₃ | N |
| I-230 | | H | F | OCH₃ | N |
| I-231 | | H | H | NH(CH₃) | N |
| I-232 | | H | N(CH₃)₂ | OCH₃ | N |
| I-233 | | H | N(CH₃)₂ | SCHF₂ | N |
| I-234 | | H | NHCH₃ | OCH₃ | N |
| I-235 | | H | OC₂H₅ | OC₂H₅ | N |
| I-236 | | H | OCF₂CHF₂ | SCH₃ | N |
| I-237 | | H | OCF₂CHFBr | SCH₃ | N |
| I-238 | | H | OCF₂CHFCF₃ | SCH₃ | N |
| I-239 | | H | OCH(CH₃)₂ | OCH₃ | N |
| I-240 | | H | OCH(CH₃)₂ | SCH₃ | N |
| I-241 | | H | OCH(CH₃)CH₂CH₃ | OCH₃ | N |
| I-242 | | H | OCH₂CF₃ | OCF₂CHF₂ | N |
| I-243 | | H | OCH₂CF₃ | OCH₃ | N |
| I-244 | | H | OCH₂CHF₂ | OCH₃ | N |
| I-245 | | H | OCH₃ | OC₂H₅ | N |
| I-246 | | H | OCH₃ | OCF₂CHF₂ | N |
| I-247 | | H | OCH₃ | OCF₂CHFBr | N |
| I-248 | | H | OCH₃ | OCF₂CHFCF₃ | N |
| I-249 | | H | OCH₃ | OCF₂CHFCl | N |
| I-250 | | H | OCH₃ | OCH₃ | N |
| I-251 | | H | OCH₃ | OCHF₂ | N |
| I-252 | | H | OCH₃ | SCH(CH₃)₂ | N |
| I-253 | | H | OCH₃ | SCH₃ | N |
| I-254 | | H | OCH₃ | SCHF₂ | N |
| I-255 | | CH₃ | CH₃ | CH₃ | CH |
| I-256 | | CH₃ | CH₃ | Cl | CH |
| I-257 | | CH₃ | CH₃ | OCH₃ | CH |
| I-258 | | CH₃ | Cl | Cl | CH |
| I-259 | | CH₃ | Cl | OCH₃ | CH |
| I-260 | | CH₃ | OCH₃ | OCH₃ | CH |
| I-261 | | CH₃ | CH₃ | CH₃ | N |
| I-262 | | CH₃ | CH₃ | Cl | N |
| I-263 | | CH₃ | CH₃ | OCH₃ | N |
| I-264 | | CH₃ | Cl | Cl | N |
| I-265 | | CH₃ | Cl | OCH₃ | N |
| I-266 | | CH₃ | N(CH₃)₂ | OCH₃ | N |
| I-267 | | CH₃ | OCH₂CH₂F | OCH₃ | N |
| I-268 | | CH₃ | OCH₃ | OCH₃ | N |
| I-269 | In I-269– | H | CF₃ | OCH₃ | CH |
| I-270 | I-402, | H | CF₃ | OCHF₂ | CH |
| I-271 | | H | CH(CH₃)₂ | OCH₃ | CH |
| I-272 | R² = Br | H | CH(OCH₃)₂ | CH₃ | CH |
| I-273 | R³ = H | H | CH₂F | OCH₃ | CH |
| I-274 | R⁴ = H | H | CH₂F | OCHF₂ | CH |
| I-275 | R⁵ = H | H | CH₂OCH₃ | CH₃ | CH |
| I-276 | | H | CH₂OCH₃ | OCH₃ | CH |
| I-277 | | H | CH₂OCH₃ | OCHF₂ | CH |
| I-278 | | H | CH₃ | CF₃ | CH |
| I-279 | | H | CH₃ | CH₃ | CH |
| I-280 | | H | CH₃ | Cl | CH |
| I-281 | | H | CH₃ | F | CH |
| I-282 | | H | CH₃ | H | CH |
| I-283 | | H | CH₃ | OC₂H₅ | CH |
| I-284 | | H | CH₃ | OCF₂CHF₂ | CH |
| I-285 | | H | CH₃ | OCF₂CHFCF₃ | CH |
| I-286 | | H | CH₃ | OCH₂CF₃ | CH |
| I-287 | | H | CH₃ | OCH₂CH₂F | CH |
| I-288 | | H | CH₃ | OCH₂CHF₂ | CH |
| I-289 | | H | CH₃ | OCH₃ | CH |

TABLE 1-continued

| No. | R², R³, R⁴, R⁵ | R⁶ | X¹ | X² | Z |
|---|---|---|---|---|---|
| I-290 | | H | $CH_3$ | $OCHF_2$ | CH |
| I-291 | | H | $CH_3$ | $SCH_3$ | CH |
| I-292 | | H | $CHF_2$ | $CH_3$ | CH |
| I-293 | | H | Cl | Cl | CH |
| I-294 | | H | Cl | H | CH |
| I-295 | | H | Cl | $N(CH_3)_2$ | CH |
| I-296 | | H | Cl | $NH_2$ | CH |
| I-297 | | H | Cl | $OC_2H_5$ | CH |
| I-298 | | H | Cl | $OCF_2CHF_2$ | CH |
| I-299 | | H | Cl | $OCF_2CHFCl$ | CH |
| I-300 | | H | Cl | $OCH_3$ | CH |
| I-301 | | H | Cl | $OCHF_2$ | CH |
| I-302 | | H | $N(CH_3)_2$ | $OCF_2CHF_2$ | CH |
| I-303 | | H | $N(CH_3)_2$ | $OCH_3$ | CH |
| I-304 | | H | $N(CH_3)_2$ | $OCHF_2$ | CH |
| I-305 | | H | $N(CH_3)_2$ | $SCHF_2$ | CH |
| I-306 | | H | $N(CH_3)C_2H_5$ | $OCHF_2$ | CH |
| I-307 | | H | $N(CH_3)OCH_3$ | $OCHF_2$ | CH |
| I-308 | | H | $NH_2$ | $OCH_3$ | CH |
| I-309 | | H | $NHCH_3$ | $OCH_3$ | CH |
| I-310 | | H | $NHCH_3$ | $OCHF_2$ | CH |
| I-311 | | H | $OC_2H_5$ | $OC_2H_5$ | CH |
| I-312 | | H | $OCF_2CHF_2$ | $SCH_3$ | CH |
| I-313 | | H | $OCH(CH_3)_2$ | $OCHF_2$ | CH |
| I-314 | | H | $OCH_2CF_3$ | $OCH_3$ | CH |
| I-315 | | H | $OCH_2CH_2F$ | $OCH_3$ | CH |
| I-316 | | H | $OCH_2CHF_2$ | $OCH_3$ | CH |
| I-317 | | H | $OCH_3$ | $OC_2H_5$ | CH |
| I-318 | | H | $OCH_3$ | $OCF_2CHF_2$ | CH |
| I-319 | | H | $OCH_3$ | $OCF_2CHFCF_3$ | CH |
| I-320 | | H | $OCH_3$ | $OCH(CH_3)_2$ | CH |
| I-321 | | H | $OCH_3$ | $OCH_3$ | CH |
| I-322 | | H | $OCH_3$ | $SCH_3$ | CH |
| I-323 | | H | $OCH_3$ | $SCHF_2$ | CH |
| I-324 | | H | $OCHF_2$ | $OCH_2CF_3$ | CH |
| I-325 | | H | $OCHF_2$ | $OCH_2CH_3$ | CH |
| I-326 | | H | $OCHF_2$ | $OCH_3$ | CH |
| I-327 | | H | $OCHF_2$ | $OCHF_2$ | CH |
| I-328 | | H | $OCHF_2$ | $SCH_3$ | CH |
| I-329 | | H | $C_2H_5$ | $OCH_3$ | N |
| I-330 | | H | $C_2H_5$ | $SCH_3$ | N |
| I-331 | | H | $CF_3$ | $OCH_3$ | N |
| I-332 | | H | $CH(CH_3)_2$ | $CH_3$ | N |
| I-333 | | H | $CH(CH_3)_2$ | Cl | N |
| I-334 | | H | $CH(CH_3)_2$ | $OCH_3$ | N |
| I-335 | | H | $CH(CH_3)_2$ | $SCH_3$ | N |
| I-336 | | H | $CH_2CF_3$ | $CH_3$ | N |
| I-337 | | H | $CH_2F$ | $CH_3$ | N |
| I-338 | | H | $CH_2F$ | $OCH_3$ | N |
| I-339 | | H | $CH_2OCH_3$ | $CH_3$ | N |
| I-340 | | H | $CH_2OCH_3$ | $OCH_3$ | N |
| I-341 | | H | $CH_2SCH_3$ | $CH_3$ | N |
| I-342 | | H | $CH_2SCH_3$ | Cl | N |
| I-343 | | H | $CH_2SCH_3$ | $OC_2H_5$ | N |
| I-344 | | H | $CH_2SCH_3$ | $OCH_3$ | N |
| I-345 | | H | $CH_2SCH_3$ | $SCH_3$ | N |
| I-346 | | H | $CH_3$ | $CF_3$ | N |
| I-347 | | H | $CH_3$ | $CH_3$ | N |
| I-348 | | H | $CH_3$ | Cl | N |
| I-349 | | H | $CH_3$ | F | N |
| I-350 | | H | $CH_3$ | H | N |
| I-351 | | H | $CH_3$ | $OCH_2CF_3$ | N |
| I-352 | | H | $CH_3$ | $OCH_2CH_2F$ | N |
| I-353 | | H | $CH_3$ | $OCH_2CHF_2$ | N |
| I-354 | | H | $CH_3$ | $OCH_3$ | N |
| I-355 | | H | $CH_3$ | $SCH_3$ | N |
| I-356 | | H | $CH_3$ | $SCHF_2$ | N |
| I-357 | | H | $CHF_2$ | $CH_3$ | N |
| I-358 | | H | $CHF_2$ | $OCH_3$ | N |
| I-359 | | H | Cl | Cl | N |
| I-360 | | H | Cl | $OCH(CH_3)_2$ | N |
| I-361 | | H | Cl | $OCH_2CF_3$ | N |
| I-362 | | H | Cl | $OCH_3$ | N |
| I-363 | | H | Cl | $SCH_3$ | N |
| I-364 | | H | F | $OCH_3$ | N |
| I-365 | | H | H | $NH(CH_3)$ | N |
| I-366 | | H | $N(CH_3)_2$ | $OCH_3$ | N |

TABLE 1-continued

| No. | R², R³, R⁴, R⁵ | R⁶ | X¹ | X² | Z |
|---|---|---|---|---|---|
| I-367 | | H | N(CH₃)₂ | SCHF₂ | N |
| I-368 | | H | NHCH₃ | OCH₃ | N |
| I-369 | | H | OC₂H₅ | OC₂H₅ | N |
| I-370 | | H | OCF₂CHF₂ | SCH₃ | N |
| I-371 | | H | OCF₂CHFBr | SCH₃ | N |
| I-372 | | H | OCF₂CHFCF₃ | SCH₃ | N |
| I-373 | | H | OCH(CH₃)₂ | OCH₃ | N |
| I-374 | | H | OCH(CH₃)₂ | SCH₃ | N |
| I-375 | | H | OCH(CH₃)CH₂CH₃ | OCH₃ | N |
| I-376 | | H | OCH₂CF₃ | OCF₂CHF₂ | N |
| I-377 | | H | OCH₂CF₃ | OCH₃ | N |
| I-378 | | H | OCH₂CHF₂ | OCH₃ | N |
| I-379 | | H | OCH₃ | OC₂H₅ | N |
| I-380 | | H | OCH₃ | OCF₂CHF₂ | N |
| I-381 | | H | OCH₃ | OCF₂CHFBr | N |
| I-382 | | H | OCH₃ | OCF₂CHFCF₃ | N |
| I-383 | | H | OCH₃ | OCF₂CHFCl | N |
| I-384 | | H | OCH₃ | OCH₃ | N |
| I-385 | | H | OCH₃ | OCHF₂ | N |
| I-386 | | H | OCH₃ | SCH(CH₃)₂ | N |
| I-387 | | H | OCH₃ | SCH₃ | N |
| I-388 | | H | OCH₃ | SCHF₂ | N |
| I-389 | | CH₃ | CH₃ | CH₃ | CH |
| I-390 | | CH₃ | CH₃ | Cl | CH |
| I-391 | | CH₃ | CH₃ | OCH₃ | CH |
| I-392 | | CH₃ | Cl | Cl | CH |
| I-393 | | CH₃ | Cl | OCH₃ | CH |
| I-394 | | CH₃ | OCH₃ | OCH₃ | CH |
| I-395 | | CH₃ | CH₃ | CH₃ | N |
| I-396 | | CH₃ | CH₃ | Cl | N |
| I-397 | | CH₃ | CH₃ | OCH₃ | N |
| I-398 | | CH₃ | Cl | Cl | N |
| I-399 | | CH₃ | Cl | OCH₃ | N |
| I-400 | | CH₃ | N(CH₃)₂ | OCH₃ | N |
| I-401 | | CH₃ | OCH₂CH₂F | OCH₃ | N |
| I-402 | | CH₃ | OCH₃ | OCH₃ | N |
| I-403 | In I-403– | H | CF₃ | OCH₃ | CH |
| I-404 | I-536, | H | CF₃ | OCHF₂ | CH |
| I-405 | | H | CH(CH₃)₂ | OCH₃ | CH |
| I-406 | R² = COCH₃ | H | CH(OCH₃)₂ | CH₃ | CH |
| I-407 | R³ = H | H | CH₂F | OCH₃ | CH |
| I-408 | R⁴ = H | H | CH₂F | OCHF₂ | CH |
| I-409 | R⁵ = H | H | CH₂OCH₃ | CH₃ | CH |
| I-410 | | H | CH₂OCH₃ | OCH₃ | CH |
| I-411 | | H | CH₂OCH₃ | OCHF₂ | CH |
| I-412 | | H | CH₃ | CF₃ | CH |
| I-413 | | H | CH₃ | CH₃ | CH |
| I-414 | | H | CH₃ | Cl | CH |
| I-415 | | H | CH₃ | F | CH |
| I-416 | | H | CH₃ | H | CH |
| I-417 | | H | CH₃ | OC₂H₅ | CH |
| I-418 | | H | CH₃ | OCF₂CHF₂ | CH |
| I-419 | | H | CH₃ | OCF₂CHFCF₃ | CH |
| I-420 | | H | CH₃ | OCH₂CF₃ | CH |
| I-421 | | H | CH₃ | OCH₂CH₂F | CH |
| I-422 | | H | CH₃ | OCH₂CHF₂ | CH |
| I-423 | | H | CH₃ | OCH₃ | CH |
| I-424 | | H | CH₃ | OCHF₂ | CH |
| I-425 | | H | CH₃ | SCH₃ | CH |
| I-426 | | H | CHF₂ | CH₃ | CH |
| I-427 | | H | Cl | Cl | CH |
| I-428 | | H | Cl | H | CH |
| I-429 | | H | Cl | N(CH₃)₂ | CH |
| I-430 | | H | Cl | NH₂ | CH |
| I-431 | | H | Cl | OC₂H₅ | CH |
| I-432 | | H | Cl | OCF₂CHF₂ | CH |
| I-433 | | H | Cl | OCF₂CHFCl | CH |
| I-434 | | H | Cl | OCH₃ | CH |
| I-435 | | H | Cl | OCHF₂ | CH |
| I-436 | | H | N(CH₃)₂ | OCF₂CHF₂ | CH |
| I-437 | | H | N(CH₃)₂ | OCH₃ | CH |
| I-438 | | H | N(CH₃)₂ | OCHF₂ | CH |
| I-439 | | H | N(CH₃)₂ | SCHF₂ | CH |
| I-440 | | H | N(CH₃)C₂H₅ | OCHF₂ | CH |
| I-441 | | H | N(CH₃)OCH₃ | OCHF₂ | CH |
| I-442 | | H | NH₂ | OCH₃ | CH |
| I-443 | | H | NHCH₃ | OCH₃ | CH |

TABLE 1-continued

| No. | R², R³, R⁴, R⁵ | R⁶ | X¹ | X² | Z |
|---|---|---|---|---|---|
| I-444 | | H | NHCH₃ | OCHF₂ | CH |
| I-445 | | H | OC₂H₅ | OC₂H₅ | CH |
| I-446 | | H | OCF₂CHF₂ | SCH₃ | CH |
| I-447 | | H | OCH(CH₃)₂ | OCHF₂ | CH |
| I-448 | | H | OCH₂CF₃ | OCH₃ | CH |
| I-449 | | H | OCH₂CH₂F | OCH₃ | CH |
| I-450 | | H | OCH₂CHF₂ | OCH₃ | CH |
| I-451 | | H | OCH₃ | OC₂H₅ | CH |
| I-452 | | H | OCH₃ | OCF₂CHF₂ | CH |
| I-453 | | H | OCH₃ | OCF₂CHFCF₃ | CH |
| I-454 | | H | OCH₃ | OCH(CH₃)₂ | CH |
| I-455 | | H | OCH₃ | OCH₃ | CH |
| I-456 | | H | OCH₃ | SCH₃ | CH |
| I-457 | | H | OCH₃ | SCHF₂ | CH |
| I-458 | | H | OCHF₂ | OCH₂CF₃ | CH |
| I-459 | | H | OCHF₂ | OCH₂CH₃ | CH |
| I-460 | | H | OCHF₂ | OCH₃ | CH |
| I-461 | | H | OCHF₂ | OCHF₂ | CH |
| I-462 | | H | OCHF₂ | SCH₃ | CH |
| I-463 | | H | C₂H₅ | OCH₃ | N |
| I-464 | | H | C₂H₅ | SCH₃ | N |
| I-465 | | H | CF₃ | OCH₃ | N |
| I-466 | | H | CH(CH₃)₂ | CH₃ | N |
| I-467 | | H | CH(CH₃)₂ | Cl | N |
| I-468 | | H | CH(CH₃)₂ | OCH₃ | N |
| I-469 | | H | CH(CH₃)₂ | SCH₃ | N |
| I-470 | | H | CH₂CF₃ | CH₃ | N |
| I-471 | | H | CH₂F | CH₃ | N |
| I-472 | | H | CH₂F | OCH₃ | N |
| I-473 | | H | CH₂OCH₃ | CH₃ | N |
| I-474 | | H | CH₂OCH₃ | OCH₃ | N |
| I-475 | | H | CH₂SCH₃ | CH₃ | N |
| I-476 | | H | CH₂SCH₃ | Cl | N |
| I-477 | | H | CH₂SCH₃ | OC₂H₅ | N |
| I-478 | | H | CH₂SCH₃ | OCH₃ | N |
| I-479 | | H | CH₂SCH₃ | SCH₃ | N |
| I-480 | | H | CH₃ | CF₃ | N |
| I-481 | | H | CH₃ | CH₃ | N |
| I-482 | | H | CH₃ | Cl | N |
| I-483 | | H | CH₃ | F | N |
| I-484 | | H | CH₃ | H | N |
| I-485 | | H | CH₃ | OCH₂CF₃ | N |
| I-486 | | H | CH₃ | OCH₂CH₂F | N |
| I-487 | | H | CH₃ | OCH₂CHF₂ | N |
| I-488 | | H | CH₃ | OCH₃ | N |
| I-489 | | H | CH₃ | SCH₃ | N |
| I-490 | | H | CH₃ | SCHF₂ | N |
| I-491 | | H | CHF₂ | CH₃ | N |
| I-492 | | H | CHF₂ | OCH₃ | N |
| I-493 | | H | Cl | Cl | N |
| I-494 | | H | Cl | OCH(CH₃)₂ | N |
| I-495 | | H | Cl | OCH₂CF₃ | N |
| I-496 | | H | Cl | OCH₃ | N |
| I-497 | | H | Cl | SCH₃ | N |
| I-498 | | H | F | OCH₃ | N |
| I-499 | | H | H | NH(CH₃) | N |
| I-500 | | H | N(CH₃)₂ | OCH₃ | N |
| I-501 | | H | N(CH₃)₂ | SCHF₂ | N |
| I-502 | | H | NHCH₃ | OCH₃ | N |
| I-503 | | H | OC₂H₅ | OC₂H₅ | N |
| I-504 | | H | OCF₂CHF₂ | SCH₃ | N |
| I-505 | | H | OCF₂CHFBr | SCH₃ | N |
| I-506 | | H | OCF₂CHFCF₃ | SCH₃ | N |
| I-507 | | H | OCH(CH₃)₂ | OCH₃ | N |
| I-508 | | H | OCH(CH₃)₂ | SCH₃ | N |
| I-509 | | H | OCH(CH₃)CH₂CH₃ | OCH₃ | N |
| I-510 | | H | OCH₂CF₃ | OCF₂CHF₂ | N |
| I-511 | | H | OCH₂CF₃ | OCH₃ | N |
| I-512 | | H | OCH₂CHF₂ | OCH₃ | N |
| I-513 | | H | OCH₃ | OC₂H₅ | N |
| I-514 | | H | OCH₃ | OCF₂CHF₂ | N |
| I-515 | | H | OCH₃ | OCF₂CHFBr | N |
| I-516 | | H | OCH₃ | OCF₂CHFCF₃ | N |
| I-517 | | H | OCH₃ | OCF₂CHFCl | N |
| I-518 | | H | OCH₃ | OCH₃ | N |
| I-519 | | H | OCH₃ | OCHF₂ | N |
| I-520 | | H | OCH₃ | SCH(CH₃)₂ | N |

TABLE 1-continued

| No. | R², R³, R⁴, R⁵ | R⁶ | X¹ | X² | Z |
|---|---|---|---|---|---|
| I-521 | | H | OCH₃ | SCH₃ | N |
| I-522 | | H | OCH₃ | SCHF₂ | N |
| I-523 | | CH₃ | CH₃ | CH₃ | CH |
| I-524 | | CH₃ | CH₃ | Cl | CH |
| I-525 | | CH₃ | CH₃ | OCH₃ | CH |
| I-526 | | CH₃ | Cl | Cl | CH |
| I-527 | | CH₃ | Cl | OCH₃ | CH |
| I-528 | | CH₃ | OCH₃ | OCH₃ | CH |
| I-529 | | CH₃ | CH₃ | CH₃ | N |
| I-530 | | CH₃ | CH₃ | Cl | N |
| I-531 | | CH₃ | CH₃ | OCH₃ | N |
| I-532 | | CH₃ | Cl | Cl | N |
| I-533 | | CH₃ | Cl | OCH₃ | N |
| I-534 | | CH₃ | N(CH₃)₂ | OCH₃ | N |
| I-535 | | CH₃ | OCH₂CH₂F | OCH₃ | N |
| I-536 | | CH₃ | OCH₃ | OCH₃ | N |
| I-537 | In I-537– | H | CF₃ | OCH₃ | CH |
| I-538 | I-670, | H | CF₃ | OCHF₂ | CH |
| I-539 | | H | CH(CH₃)₂ | OCH₃ | CH |
| I-540 | R² = COC₂H₅ | H | CH(OCH₃)₂ | CH₃ | CH |
| I-541 | R³ = H | H | CH₂F | OCH₃ | CH |
| I-542 | R⁴ = H | H | CH₂F | OCHF₂ | CH |
| I-543 | R⁵ = H | H | CH₂OCH₃ | CH₃ | CH |
| I-544 | | H | CH₂OCH₃ | OCH₃ | CH |
| I-545 | | H | CH₂OCH₃ | OCHF₂ | CH |
| I-546 | | H | CH₃ | CF₃ | CH |
| I-547 | | H | CH₃ | CH₃ | CH |
| I-548 | | H | CH₃ | Cl | CH |
| I-549 | | H | CH₃ | F | CH |
| I-550 | | H | CH₃ | H | CH |
| I-551 | | H | CH₃ | OC₂H₅ | CH |
| I-552 | | H | CH₃ | OCF₂CHF₂ | CH |
| I-553 | | H | CH₃ | OCF₂CHFCF₃ | CH |
| I-554 | | H | CH₃ | OCH₂CF₃ | CH |
| I-555 | | H | CH₃ | OCH₂CH₂F | CH |
| I-556 | | H | CH₃ | OCH₂CHF₂ | CH |
| I-557 | | H | CH₃ | OCH₃ | CH |
| I-558 | | H | CH₃ | OCHF₂ | CH |
| I-559 | | H | CH₃ | SCH₃ | CH |
| I-560 | | H | CHF₂ | CH₃ | CH |
| I-561 | | H | Cl | Cl | CH |
| I-562 | | H | Cl | H | CH |
| I-563 | | H | Cl | N(CH₃)₂ | CH |
| I-564 | | H | Cl | NH₂ | CH |
| I-565 | | H | Cl | OC₂H₅ | CH |
| I-566 | | H | Cl | OCF₂CHF₂ | CH |
| I-567 | | H | Cl | OCF₂CHFCl | CH |
| I-568 | | H | Cl | OCH₃ | CH |
| I-569 | | H | Cl | OCHF₂ | CH |
| I-570 | | H | N(CH₃)₂ | OCF₂CHF₂ | CH |
| I-571 | | H | N(CH₃)₂ | OCH₃ | CH |
| I-572 | | H | N(CH₃)₂ | OCHF₂ | CH |
| I-573 | | H | N(CH₃)₂ | SCHF₂ | CH |
| I-574 | | H | N(CH₃)C₂H₅ | OCHF₂ | CH |
| I-575 | | H | N(CH₃)OCH₃ | OCHF₂ | CH |
| I-576 | | H | NH₂ | OCH₃ | CH |
| I-577 | | H | NHCH₃ | OCH₃ | CH |
| I-578 | | H | NHCH₃ | OCHF₂ | CH |
| I-579 | | H | OC₂H₅ | OC₂H₅ | CH |
| I-580 | | H | OCF₂CHF₂ | SCH₃ | CH |
| I-581 | | H | OCH(CH₃)₂ | OCHF₂ | CH |
| I-582 | | H | OCH₂CF₃ | OCH₃ | CH |
| I-583 | | H | OCH₂CH₂F | OCH₃ | CH |
| I-584 | | H | OCH₂CHF₂ | OCH₃ | CH |
| I-585 | | H | OCH₃ | OC₂H₅ | CH |
| I-586 | | H | OCH₃ | OCF₂CHF₂ | CH |
| I-587 | | H | OCH₃ | OCF₂CHFCF₃ | CH |
| I-588 | | H | OCH₃ | OCH(CH₃)₂ | CH |
| I-589 | | H | OCH₃ | OCH₃ | CH |
| I-590 | | H | OCH₃ | SCH₃ | CH |
| I-591 | | H | OCH₃ | SCHF₂ | CH |
| I-592 | | H | OCHF₂ | OCH₂CF₃ | CH |
| I-593 | | H | OCHF₂ | OCH₂CH₃ | CH |
| I-594 | | H | OCHF₂ | OCH₃ | CH |
| I-595 | | H | OCHF₂ | OCHF₂ | CH |
| I-596 | | H | OCHF₂ | SCH₃ | CH |
| I-597 | | H | C₂H₅ | OCH₃ | N |

TABLE 1-continued

| No. | R², R³, R⁴, R⁵ | R⁶ | X¹ | X² | Z |
|---|---|---|---|---|---|
| I-598 | | H | C₂H₅ | SCH₃ | N |
| I-599 | | H | CF₃ | OCH₃ | N |
| I-600 | | H | CH(CH₃)₂ | CH₃ | N |
| I-601 | | H | CH(CH₃)₂ | Cl | N |
| I-602 | | H | CH(CH₃)₂ | OCH₃ | N |
| I-603 | | H | CH(CH₃)₂ | SCH₃ | N |
| I-604 | | H | CH₂CF₃ | CH₃ | N |
| I-605 | | H | CH₂F | CH₃ | N |
| I-606 | | H | CH₂F | OCH₃ | N |
| I-607 | | H | CH₂OCH₃ | CH₃ | N |
| I-608 | | H | CH₂OCH₃ | OCH₃ | N |
| I-609 | | H | CH₂SCH₃ | CH₃ | N |
| I-610 | | H | CH₂SCH₃ | Cl | N |
| I-611 | | H | CH₂SCH₃ | OC₂H₅ | N |
| I-612 | | H | CH₂SCH₃ | OCH₃ | N |
| I-613 | | H | CH₂SCH₃ | SCH₃ | N |
| I-614 | | H | CH₃ | CF₃ | N |
| I-615 | | H | CH₃ | CH₃ | N |
| I-616 | | H | CH₃ | Cl | N |
| I-617 | | H | CH₃ | F | N |
| I-618 | | H | CH₃ | H | N |
| I-619 | | H | CH₃ | OCH₂CF₃ | N |
| I-620 | | H | CH₃ | OCH₂CH₂F | N |
| I-621 | | H | CH₃ | OCH₂CHF₂ | N |
| I-622 | | H | CH₃ | OCH₃ | N |
| I-623 | | H | CH₃ | SCH₃ | N |
| I-624 | | H | CH₃ | SCHF₂ | N |
| I-625 | | H | CHF₂ | CH₃ | N |
| I-626 | | H | CHF₂ | OCH₃ | N |
| I-627 | | H | Cl | Cl | N |
| I-628 | | H | Cl | OCH(CH₃)₂ | N |
| I-629 | | H | Cl | OCH₂CF₃ | N |
| I-630 | | H | Cl | OCH₃ | N |
| I-631 | | H | Cl | SCH₃ | N |
| I-632 | | H | F | OCH₃ | N |
| I-633 | | H | H | NH(CH₃) | N |
| I-634 | | H | N(CH₃)₂ | OCH₃ | N |
| I-635 | | H | N(CH₃)₂ | SCHF₂ | N |
| I-636 | | H | NHCH₃ | OCH₃ | N |
| I-637 | | H | OC₂H₅ | OC₂H₅ | N |
| I-638 | | H | OCF₂CHF₂ | SCH₃ | N |
| I-639 | | H | OCF₂CHFBr | SCH₃ | N |
| I-640 | | H | OCF₂CHFCF₃ | SCH₃ | N |
| I-641 | | H | OCH(CH₃)₂ | OCH₃ | N |
| I-642 | | H | OCH(CH₃)₂ | SCH₃ | N |
| I-643 | | H | OCH(CH₃)CH₂CH₃ | OCH₃ | N |
| I-644 | | H | OCH₂CF₃ | OCF₂CHF₂ | N |
| I-645 | | H | OCH₂CF₃ | OCH₃ | N |
| I-646 | | H | OCH₂CHF₂ | OCH₃ | N |
| I-647 | | H | OCH₃ | OC₂H₅ | N |
| I-648 | | H | OCH₃ | OCF₂CHF₂ | N |
| I-649 | | H | OCH₃ | OCF₂CHFBr | N |
| I-650 | | H | OCH₃ | OCF₂CHFCF₃ | N |
| I-651 | | H | OCH₃ | OCF₂CHFCl | N |
| I-652 | | H | OCH₃ | OCH₃ | N |
| I-653 | | H | OCH₃ | OCHF₂ | N |
| I-654 | | H | OCH₃ | SCH(CH₃)₂ | N |
| I-655 | | H | OCH₃ | SCH₃ | N |
| I-656 | | H | OCH₃ | SCHF₂ | N |
| I-657 | | CH₃ | CH₃ | CH₃ | CH |
| I-658 | | CH₃ | CH₃ | Cl | CH |
| I-659 | | CH₃ | CH₃ | OCH₃ | CH |
| I-660 | | CH₃ | Cl | Cl | CH |
| I-661 | | CH₃ | Cl | OCH₃ | CH |
| I-662 | | CH₃ | OCH₃ | OCH₃ | CH |
| I-663 | | CH₃ | CH₃ | CH₃ | N |
| I-664 | | CH₃ | CH₃ | Cl | N |
| I-665 | | CH₃ | CH₃ | OCH₃ | N |
| I-666 | | CH₃ | Cl | Cl | N |
| I-667 | | CH₃ | Cl | OCH₃ | N |
| I-668 | | CH₃ | N(CH₃)₂ | OCH₃ | N |
| I-669 | | CH₃ | OCH₂CH₂F | OCH₃ | N |
| I-670 | | CH₃ | OCH₃ | OCH₃ | N |
| I-671 | In I-671– | H | CF₃ | OCH₃ | CH |
| I-672 | I-804, | H | CF₃ | OCHF₂ | CH |
| I-673 | | H | CH(CH₃)₂ | OCH₃ | CH |
| I-674 | R² = COCF₃ | H | CH(OCH₃)₂ | CH₃ | CH |

TABLE 1-continued

| No. | $R^2, R^3, R^4, R^5$ | $R^6$ | $X^1$ | $X^2$ | Z |
|---|---|---|---|---|---|
| I-675 | $R^3 = H$ | H | $CH_2F$ | $OCH_3$ | CH |
| I-676 | $R^4 = H$ | H | $CH_2F$ | $OCHF_2$ | CH |
| I-677 | $R^5 = H$ | H | $CH_2OCH_3$ | $CH_3$ | CH |
| I-678 | | H | $CH_2OCH_3$ | $OCH_3$ | CH |
| I-679 | | H | $CH_2OCH_3$ | $OCHF_2$ | CH |
| I-680 | | H | $CH_3$ | $CF_3$ | CH |
| I-681 | | H | $CH_3$ | $CH_3$ | CH |
| I-682 | | H | $CH_3$ | Cl | CH |
| I-683 | | H | $CH_3$ | F | CH |
| I-684 | | H | $CH_3$ | H | CH |
| I-685 | | H | $CH_3$ | $OC_2H_5$ | CH |
| I-686 | | H | $CH_3$ | $OCF_2CHF_2$ | CH |
| I-687 | | H | $CH_3$ | $OCF_2CHFCF_3$ | CH |
| I-688 | | H | $CH_3$ | $OCH_2CF_3$ | CH |
| I-689 | | H | $CH_3$ | $OCH_2CH_2F$ | CH |
| I-690 | | H | $CH_3$ | $OCH_2CHF_2$ | CH |
| I-691 | | H | $CH_3$ | $OCH_3$ | CH |
| I-692 | | H | $CH_3$ | $OCHF_2$ | CH |
| I-693 | | H | $CH_3$ | $SCH_3$ | CH |
| I-694 | | H | $CHF_2$ | $CH_3$ | CH |
| I-695 | | H | Cl | Cl | CH |
| I-696 | | H | Cl | H | CH |
| I-697 | | H | Cl | $N(CH_3)_2$ | CH |
| I-698 | | H | Cl | $NH_2$ | CH |
| I-699 | | H | Cl | $OC_2H_5$ | CH |
| I-700 | | H | Cl | $OCF_2CHF_2$ | CH |
| I-701 | | H | Cl | $OCF_2CHFCl$ | CH |
| I-702 | | H | Cl | $OCH_3$ | CH |
| I-703 | | H | Cl | $OCHF_2$ | CH |
| I-704 | | H | $N(CH_3)_2$ | $OCF_2CHF_2$ | CH |
| I-705 | | H | $N(CH_3)_2$ | $OCH_3$ | CH |
| I-706 | | H | $N(CH_3)_2$ | $OCHF_2$ | CH |
| I-707 | | H | $N(CH_3)_2$ | $SCHF_2$ | CH |
| I-708 | | H | $N(CH_3)C_2H_5$ | $OCHF_2$ | CH |
| I-709 | | H | $N(CH_3)OCH_3$ | $OCHF_2$ | CH |
| I-710 | | H | $NH_2$ | $OCH_3$ | CH |
| I-711 | | H | $NHCH_3$ | $OCH_3$ | CH |
| I-712 | | H | $NHCH_3$ | $OCHF_2$ | CH |
| I-713 | | H | $OC_2H_5$ | $OC_2H_5$ | CH |
| I-714 | | H | $OCF_2CHF_2$ | $SCH_3$ | CH |
| I-715 | | H | $OCH(CH_3)_2$ | $OCHF_2$ | CH |
| I-716 | | H | $OCH_2CF_3$ | $OCH_3$ | CH |
| I-717 | | H | $OCH_2CH_2F$ | $OCH_3$ | CH |
| I-718 | | H | $OCH_2CHF_2$ | $OCH_3$ | CH |
| I-719 | | H | $OCH_3$ | $OC_2H_5$ | CH |
| I-720 | | H | $OCH_3$ | $OCF_2CHF_2$ | CH |
| I-721 | | H | $OCH_3$ | $OCF_2CHFCF_3$ | CH |
| I-722 | | H | $OCH_3$ | $OCH(CH_3)_2$ | CH |
| I-723 | | H | $OCH_3$ | $OCH_3$ | CH |
| I-724 | | H | $OCH_3$ | $SCH_3$ | CH |
| I-725 | | H | $OCH_3$ | $SCHF_2$ | CH |
| I-726 | | H | $OCHF_2$ | $OCH_2CF_3$ | CH |
| I-727 | | H | $OCHF_2$ | $OCH_2CH_3$ | CH |
| I-728 | | H | $OCHF_2$ | $OCH_3$ | CH |
| I-729 | | H | $OCHF_2$ | $OCHF_2$ | CH |
| I-730 | | H | $OCHF_2$ | $SCH_3$ | CH |
| I-731 | | H | $C_2H_5$ | $OCH_3$ | N |
| I-732 | | H | $C_2H_5$ | $SCH_3$ | N |
| I-733 | | H | $CF_3$ | $OCH_3$ | N |
| I-734 | | H | $CH(CH_3)_2$ | $CH_3$ | N |
| I-735 | | H | $CH(CH_3)_2$ | Cl | N |
| I-736 | | H | $CH(CH_3)_2$ | $OCH_3$ | N |
| I-737 | | H | $CH(CH_3)_2$ | $SCH_3$ | N |
| I-738 | | H | $CH_2CF_3$ | $CH_3$ | N |
| I-739 | | H | $CH_2F$ | $CH_3$ | N |
| I-740 | | H | $CH_2F$ | $OCH_3$ | N |
| I-741 | | H | $CH_2OCH_3$ | $CH_3$ | N |
| I-742 | | H | $CH_2OCH_3$ | $OCH_3$ | N |
| I-743 | | H | $CH_2SCH_3$ | $CH_3$ | N |
| I-744 | | H | $CH_2SCH_3$ | Cl | N |
| I-745 | | H | $CH_2SCH_3$ | $OC_2H_5$ | N |
| I-746 | | H | $CH_2SCH_3$ | $OCH_3$ | N |
| I-747 | | H | $CH_2SCH_3$ | $SCH_3$ | N |
| I-748 | | H | $CH_3$ | $CF_3$ | N |
| I-749 | | H | $CH_3$ | $CH_3$ | N |
| I-750 | | H | $CH_3$ | Cl | N |
| I-751 | | H | $CH_3$ | F | N |

TABLE 1-continued

| No. | $R^2, R^3, R^4, R^5$ | $R^6$ | $X^1$ | $X^2$ | Z |
|---|---|---|---|---|---|
| I-752 | | H | $CH_3$ | H | N |
| I-753 | | H | $CH_3$ | $OCH_2CF_3$ | N |
| I-754 | | H | $CH_3$ | $OCH_2CH_2F$ | N |
| I-755 | | H | $CH_3$ | $OCH_2CHF_2$ | N |
| I-756 | | H | $CH_3$ | $OCH_3$ | N |
| I-757 | | H | $CH_3$ | $SCH_3$ | N |
| I-758 | | H | $CH_3$ | $SCHF_2$ | N |
| I-759 | | H | $CHF_2$ | $CH_3$ | N |
| I-760 | | H | $CHF_2$ | $OCH_3$ | N |
| I-761 | | H | Cl | Cl | N |
| I-762 | | H | Cl | $OCH(CH_3)_2$ | N |
| I-763 | | H | Cl | $OCH_2CF_3$ | N |
| I-764 | | H | Cl | $OCH_3$ | N |
| I-765 | | H | Cl | $SCH_3$ | N |
| I-766 | | H | F | $OCH_3$ | N |
| I-767 | | H | H | $NH(CH_3)$ | N |
| I-768 | | H | $N(CH_3)_2$ | $OCH_3$ | N |
| I-769 | | H | $N(CH_3)_2$ | $SCHF_2$ | N |
| I-770 | | H | $NHCH_3$ | $OCH_3$ | N |
| I-771 | | H | $OC_2H_5$ | $OC_2H_5$ | N |
| I-772 | | H | $OCF_2CHF_2$ | $SCH_3$ | N |
| I-773 | | H | $OCF_2CHFBr$ | $SCH_3$ | N |
| I-774 | | H | $OCF_2CHFCF_3$ | $SCH_3$ | N |
| I-775 | | H | $OCH(CH_3)_2$ | $OCH_3$ | N |
| I-776 | | H | $OCH(CH_3)_2$ | $SCH_3$ | N |
| I-777 | | H | $OCH(CH_3)CH_2CH_3$ | $OCH_3$ | N |
| I-778 | | H | $OCH_2CF_3$ | $OCF_2CHF_2$ | N |
| I-779 | | H | $OCH_2CF_3$ | $OCH_3$ | N |
| I-780 | | H | $OCH_2CHF_2$ | $OCH_3$ | N |
| I-781 | | H | $OCH_3$ | $OC_2H_5$ | N |
| I-782 | | H | $OCH_3$ | $OCF_2CHF_2$ | N |
| I-783 | | H | $OCH_3$ | $OCF_2CHFBr$ | N |
| I-784 | | H | $OCH_3$ | $OCF_2CHFCF_3$ | N |
| I-785 | | H | $OCH_3$ | $OCF_2CHFCl$ | N |
| I-786 | | H | $OCH_3$ | $OCH_3$ | N |
| I-787 | | H | $OCH_3$ | $OCHF_2$ | N |
| I-788 | | H | $OCH_3$ | $SCH(CH_3)_2$ | N |
| I-789 | | H | $OCH_3$ | $SCH_3$ | N |
| I-790 | | H | $OCH_3$ | $SCHF_2$ | N |
| I-791 | | $CH_3$ | $CH_3$ | $CH_3$ | CH |
| I-792 | | $CH_3$ | $CH_3$ | Cl | CH |
| I-793 | | $CH_3$ | $CH_3$ | $OCH_3$ | CH |
| I-794 | | $CH_3$ | Cl | Cl | CH |
| I-795 | | $CH_3$ | Cl | $OCH_3$ | CH |
| I-796 | | $CH_3$ | $OCH_3$ | $OCH_3$ | CH |
| I-797 | | $CH_3$ | $CH_3$ | $CH_3$ | N |
| I-798 | | $CH_3$ | $CH_3$ | Cl | N |
| I-799 | | $CH_3$ | $CH_3$ | $OCH_3$ | N |
| I-800 | | $CH_3$ | Cl | Cl | N |
| I-801 | | $CH_3$ | Cl | $OCH_3$ | N |
| I-802 | | $CH_3$ | $N(CH_3)_2$ | $OCH_3$ | N |
| I-803 | | $CH_3$ | $OCH_2CH_2F$ | $OCH_3$ | N |
| I-804 | | $CH_3$ | $OCH_3$ | $OCH_3$ | N |
| I-805 | In I-805– | H | $CF_3$ | $OCH_3$ | CH |
| I-806 | I-938, | H | $CF_3$ | $OCHF_2$ | CH |
| I-807 | | H | $CH(CH_3)_2$ | $OCH_3$ | CH |
| I-808 | $R^2 = CO(CH_2)_3Cl$ | H | $CH(OCH_3)_2$ | $CH_3$ | CH |
| I-809 | $R^3 = H$ | H | $CH_2F$ | $OCH_3$ | CH |
| I-810 | $R^4 = H$ | H | $CH_2F$ | $OCHF_2$ | CH |
| I-811 | $R^5 = H$ | H | $CH_2OCH_3$ | $CH_3$ | CH |
| I-812 | | H | $CH_2OCH_3$ | $OCH_3$ | CH |
| I-813 | | H | $CH_2OCH_3$ | $OCHF_2$ | CH |
| I-814 | | H | $CH_3$ | $CF_3$ | CH |
| I-815 | | H | $CH_3$ | $CH_3$ | CH |
| I-816 | | H | $CH_3$ | Cl | CH |
| I-817 | | H | $CH_3$ | F | CH |
| I-818 | | H | $CH_3$ | H | CH |
| I-819 | | H | $CH_3$ | $OC_2H_5$ | CH |
| I-820 | | H | $CH_3$ | $OCF_2CHF_2$ | CH |
| I-821 | | H | $CH_3$ | $OCF_2CHFCF_3$ | CH |
| I-822 | | H | $CH_3$ | $OCH_2CF_3$ | CH |
| I-823 | | H | $CH_3$ | $OCH_2CH_2F$ | CH |
| I-824 | | H | $CH_3$ | $OCH_2CHF_2$ | CH |
| I-825 | | H | $CH_3$ | $OCH_3$ | CH |
| I-826 | | H | $CH_3$ | $OCHF_2$ | CH |
| I-827 | | H | $CH_3$ | $SCH_3$ | CH |
| I-828 | | H | $CHF_2$ | $CH_3$ | CH |

TABLE 1-continued

| No. | R², R³, R⁴, R⁵ | R⁶ | X¹ | X² | Z |
|---|---|---|---|---|---|
| I-829 | | H | Cl | Cl | CH |
| I-830 | | H | Cl | H | CH |
| I-831 | | H | Cl | N(CH₃)₂ | CH |
| I-832 | | H | Cl | NH₂ | CH |
| I-833 | | H | Cl | OC₂H₅ | CH |
| I-834 | | H | Cl | OCF₂CHF₂ | CH |
| I-835 | | H | Cl | OCF₂CHFCl | CH |
| I-836 | | H | Cl | OCH₃ | CH |
| I-837 | | H | Cl | OCHF₂ | CH |
| I-838 | | H | N(CH₃)₂ | OCF₂CHF₂ | CH |
| I-839 | | H | N(CH₃)₂ | OCH₃ | CH |
| I-840 | | H | N(CH₃)₂ | OCHF₂ | CH |
| I-841 | | H | N(CH₃)₂ | SCHF₂ | CH |
| I-842 | | H | N(CH₃)C₂H₅ | OCHF₂ | CH |
| I-843 | | H | N(CH₃)OCH₃ | OCHF₂ | CH |
| I-844 | | H | NH₂ | OCH₃ | CH |
| I-845 | | H | NHCH₃ | OCH₃ | CH |
| I-846 | | H | NHCH₃ | OCHF₂ | CH |
| I-847 | | H | OC₂H₅ | OC₂H₅ | CH |
| I-848 | | H | OCF₂CHF₂ | SCH₃ | CH |
| I-849 | | H | OCH(CH₃)₂ | OCHF₂ | CH |
| I-850 | | H | OCH₂CF₃ | OCH₃ | CH |
| I-851 | | H | OCH₂CH₂F | OCH₃ | CH |
| I-852 | | H | OCH₂CHF₂ | OCH₃ | CH |
| I-853 | | H | OCH₃ | OC₂H₅ | CH |
| I-854 | | H | OCH₃ | OCF₂CHF₂ | CH |
| I-855 | | H | OCH₃ | OCF₂CHFCF₃ | CH |
| I-856 | | H | OCH₃ | OCH(CH₃)₂ | CH |
| I-857 | | H | OCH₃ | OCH₃ | CH |
| I-858 | | H | OCH₃ | SCH₃ | CH |
| I-859 | | H | OCH₃ | SCHF₂ | CH |
| I-860 | | H | OCHF₂ | OCH₂CF₃ | CH |
| I-861 | | H | OCHF₂ | OCH₂CH₃ | CH |
| I-862 | | H | OCHF₂ | OCH₃ | CH |
| I-863 | | H | OCHF₂ | OCHF₂ | CH |
| I-864 | | H | OCHF₂ | SCH₃ | CH |
| I-865 | | H | C₂H₅ | OCH₃ | N |
| I-866 | | H | C₂H₅ | SCH₃ | N |
| I-867 | | H | CF₃ | OCH₃ | N |
| I-868 | | H | CH(CH₃)₂ | CH₃ | N |
| I-869 | | H | CH(CH₃)₂ | Cl | N |
| I-870 | | H | CH(CH₃)₂ | OCH₃ | N |
| I-871 | | H | CH(CH₃)₂ | SCH₃ | N |
| I-872 | | H | CH₂CF₃ | CH₃ | N |
| I-873 | | H | CH₂F | CH₃ | N |
| I-874 | | H | CH₂F | OCH₃ | N |
| I-875 | | H | CH₂OCH₃ | CH₃ | N |
| I-876 | | H | CH₂OCH₃ | OCH₃ | N |
| I-877 | | H | CH₂SCH₃ | CH₃ | N |
| I-878 | | H | CH₂SCH₃ | Cl | N |
| I-879 | | H | CH₂SCH₃ | OC₂H₅ | N |
| I-880 | | H | CH₂SCH₃ | OCH₃ | N |
| I-881 | | H | CH₂SCH₃ | SCH₃ | N |
| I-882 | | H | CH₃ | CF₃ | N |
| I-883 | | H | CH₃ | CH₃ | N |
| I-884 | | H | CH₃ | Cl | N |
| I-885 | | H | CH₃ | F | N |
| I-886 | | H | CH₃ | H | N |
| I-887 | | H | CH₃ | OCH₂CF₃ | N |
| I-888 | | H | CH₃ | OCH₂CH₂F | N |
| I-889 | | H | CH₃ | OCH₂CHF₂ | N |
| I-890 | | H | CH₃ | OCH₃ | N |
| I-891 | | H | CH₃ | SCH₃ | N |
| I-892 | | H | CH₃ | SCHF₂ | N |
| I-893 | | H | CHF₂ | CH₃ | N |
| I-894 | | H | CHF₂ | OCH₃ | N |
| I-895 | | H | Cl | Cl | N |
| I-896 | | H | Cl | OCH(CH₃)₂ | N |
| I-897 | | H | Cl | OCH₂CF₃ | N |
| I-898 | | H | Cl | OCH₃ | N |
| I-899 | | H | Cl | SCH₃ | N |
| I-900 | | H | F | OCH₃ | N |
| I-901 | | H | H | NH(CH₃) | N |
| I-902 | | H | N(CH₃)₂ | OCH₃ | N |
| I-903 | | H | N(CH₃)₂ | SCHF₂ | N |
| I-904 | | H | NHCH₃ | OCH₃ | N |
| I-905 | | H | OC₂H₅ | OC₂H₅ | N |

TABLE 1-continued

| No. | R², R³, R⁴, R⁵ | R⁶ | X¹ | X² | Z |
|---|---|---|---|---|---|
| I-906 | | H | OCF₂CHF₂ | SCH₃ | N |
| I-907 | | H | OCF₂CHFBr | SCH₃ | N |
| I-908 | | H | OCF₂CHFCF₃ | SCH₃ | N |
| I-909 | | H | OCH(CH₃)₂ | OCH₃ | N |
| I-910 | | H | OCH(CH₃)₂ | SCH₃ | N |
| I-911 | | H | OCH(CH₃)CH₂CH₃ | OCH₃ | N |
| I-912 | | H | OCH₂CF₃ | OCF₂CHF₂ | N |
| I-913 | | H | OCH₂CF₃ | OCH₃ | N |
| I-914 | | H | OCH₂CHF₂ | OCH₃ | N |
| I-915 | | H | OCH₃ | OC₂H₅ | N |
| I-916 | | H | OCH₃ | OCF₂CHF₂ | N |
| I-917 | | H | OCH₃ | OCF₂CHFBr | N |
| I-918 | | H | OCH₃ | OCF₂CHFCF₃ | N |
| I-919 | | H | OCH₃ | OCF₂CHFCl | N |
| I-920 | | H | OCH₃ | OCH₃ | N |
| I-921 | | H | OCH₃ | OCHF₂ | N |
| I-922 | | H | OCH₃ | SCH(CH₃)₂ | N |
| I-923 | | H | OCH₃ | SCH₃ | N |
| I-924 | | H | OCH₃ | SCHF₂ | N |
| I-925 | | CH₃ | CH₃ | CH₃ | CH |
| I-926 | | CH₃ | CH₃ | Cl | CH |
| I-927 | | CH₃ | CH₃ | OCH₃ | CH |
| I-928 | | CH₃ | Cl | Cl | CH |
| I-929 | | CH₃ | Cl | OCH₃ | CH |
| I-930 | | CH₃ | OCH₃ | OCH₃ | CH |
| I-931 | | CH₃ | CH₃ | CH₃ | N |
| I-932 | | CH₃ | CH₃ | Cl | N |
| I-933 | | CH₃ | CH₃ | OCH₃ | N |
| I-934 | | CH₃ | Cl | Cl | N |
| I-935 | | CH₃ | Cl | OCH₃ | N |
| I-936 | | CH₃ | N(CH₃)₂ | OCH₃ | N |
| I-937 | | CH₃ | OCH₂CH₂F | OCH₃ | N |
| I-938 | | CH₃ | OCH₃ | OCH₃ | N |
| I-939 | In I-939– | H | CF₃ | OCH₃ | CH |
| I-940 | I-1072, | H | CF₃ | OCHF₂ | CH |
| I-941 | | H | CH(CH₃)₂ | OCH₃ | CH |
| I-942 | R² = CO—cyc—Pr | H | CH(OCH₃)₂ | CH₃ | CH |
| I-943 | R³ = H | H | CH₂F | OCH₃ | CH |
| I-944 | R⁴ = H | H | CH₂F | OCHF₂ | CH |
| I-945 | R⁵ = H | H | CH₂OCH₃ | CH₃ | CH |
| I-946 | | H | CH₂OCH₃ | OCH₃ | CH |
| I-947 | | H | CH₂OCH₃ | OCHF₂ | CH |
| I-948 | | H | CH₃ | CF₃ | CH |
| I-949 | | H | CH₃ | CH₃ | CH |
| I-950 | | H | CH₃ | Cl | CH |
| I-951 | | H | CH₃ | F | CH |
| I-952 | | H | CH₃ | H | CH |
| I-953 | | H | CH₃ | OC₂H₅ | CH |
| I-954 | | H | CH₃ | OCF₂CHF₂ | CH |
| I-955 | | H | CH₃ | OCF₂CHFCF₃ | CH |
| I-956 | | H | CH₃ | OCH₂CF₃ | CH |
| I-957 | | H | CH₃ | OCH₂CH₂F | CH |
| I-958 | | H | CH₃ | OCH₂CHF₂ | CH |
| I-959 | | H | CH₃ | OCH₃ | CH |
| I-960 | | H | CH₃ | OCHF₂ | CH |
| I-961 | | H | CH₃ | SCH₃ | CH |
| I-962 | | H | CHF₂ | CH₃ | CH |
| I-963 | | H | Cl | Cl | CH |
| I-964 | | H | Cl | H | CH |
| I-965 | | H | Cl | N(CH₃)₂ | CH |
| I-966 | | H | Cl | NH₂ | CH |
| I-967 | | H | Cl | OC₂H₅ | CH |
| I-968 | | H | Cl | OCF₂CHF₂ | CH |
| I-969 | | H | Cl | OCF₂CHFCl | CH |
| I-970 | | H | Cl | OCH₃ | CH |
| I-971 | | H | Cl | OCHF₂ | CH |
| I-972 | | H | N(CH₃)₂ | OCF₂CHF₂ | CH |
| I-973 | | H | N(CH₃)₂ | OCH₃ | CH |
| I-974 | | H | N(CH₃)₂ | OCHF₂ | CH |
| I-975 | | H | N(CH₃)₂ | SCHF₂ | CH |
| I-976 | | H | N(CH₃)C₂H₅ | OCHF₂ | CH |
| I-977 | | H | N(CH₃)OCH₃ | OCHF₂ | CH |
| I-978 | | H | NH₂ | OCH₃ | CH |
| I-979 | | H | NHCH₃ | OCH₃ | CH |
| I-980 | | H | NHCH₃ | OCHF₂ | CH |
| I-981 | | H | OC₂H₅ | OC₂H₅ | CH |
| I-982 | | H | OCF₂CHF₂ | SCH₃ | CH |

TABLE 1-continued

| No. | R², R³, R⁴, R⁵ | R⁶ | X¹ | X² | Z |
|---|---|---|---|---|---|
| I-983 | | H | OCH(CH₃)₂ | OCHF₂ | CH |
| I-984 | | H | OCH₂CF₃ | OCH₃ | CH |
| I-985 | | H | OCH₂CH₂F | OCH₃ | CH |
| I-986 | | H | OCH₂CHF₂ | OCH₃ | CH |
| I-987 | | H | OCH₃ | OC₂H₅ | CH |
| I-988 | | H | OCH₃ | OCF₂CHF₂ | CH |
| I-989 | | H | OCH₃ | OCF₂CHFCF₃ | CH |
| I-990 | | H | OCH₃ | OCH(CH₃)₂ | CH |
| I-991 | | H | OCH₃ | OCH₃ | CH |
| I-992 | | H | OCH₃ | SCH₃ | CH |
| I-993 | | H | OCH₃ | SCHF₂ | CH |
| I-994 | | H | OCHF₂ | OCH₂CF₃ | CH |
| I-995 | | H | OCHF₂ | OCH₂CH₃ | CH |
| I-996 | | H | OCHF₂ | OCH₃ | CH |
| I-997 | | H | OCHF₂ | OCHF₂ | CH |
| I-998 | | H | OCHF₂ | SCH₃ | CH |
| I-999 | | H | C₂H₅ | OCH₃ | N |
| I-1000 | | H | C₂H₅ | SCH₃ | N |
| I-1001 | | H | CF₃ | OCH₃ | N |
| I-1002 | | H | CH(CH₃)₂ | CH₃ | N |
| I-1003 | | H | CH(CH₃)₂ | Cl | N |
| I-1004 | | H | CH(CH₃)₂ | OCH₃ | N |
| I-1005 | | H | CH(CH₃)₂ | SCH₃ | N |
| I-1006 | | H | CH₂CF₃ | CH₃ | N |
| I-1007 | | H | CH₂F | CH₃ | N |
| I-1008 | | H | CH₂F | OCH₃ | N |
| I-1009 | | H | CH₂OCH₃ | CH₃ | N |
| I-1010 | | H | CH₂OCH₃ | OCH₃ | N |
| I-1011 | | H | CH₂SCH₃ | CH₃ | N |
| I-1012 | | H | CH₂SCH₃ | Cl | N |
| I-1013 | | H | CH₂SCH₃ | OC₂H₅ | N |
| I-1014 | | H | CH₂SCH₃ | OCH₃ | N |
| I-1015 | | H | CH₂SCH₃ | SCH₃ | N |
| I-1016 | | H | CH₃ | CF₃ | N |
| I-1017 | | H | CH₃ | CH₃ | N |
| I-1018 | | H | CH₃ | Cl | N |
| I-1019 | | H | CH₃ | F | N |
| I-1020 | | H | CH₃ | H | N |
| I-1021 | | H | CH₃ | OCH₂CF₃ | N |
| I-1022 | | H | CH₃ | OCH₂CH₂F | N |
| I-1023 | | H | CH₃ | OCH₂CHF₂ | N |
| I-1024 | | H | CH₃ | OCH₃ | N |
| I-1025 | | H | CH₃ | SCH₃ | N |
| I-1026 | | H | CH₃ | SCHF₂ | N |
| I-1027 | | H | CHF₂ | CH₃ | N |
| I-1028 | | H | CHF₂ | OCH₃ | N |
| I-1029 | | H | Cl | Cl | N |
| I-1030 | | H | Cl | OCH(CH₃)₂ | N |
| I-1031 | | H | Cl | OCH₂CF₃ | N |
| I-1032 | | H | Cl | OCH₃ | N |
| I-1033 | | H | Cl | SCH₃ | N |
| I-1034 | | H | F | OCH₃ | N |
| I-1035 | | H | H | NH(CH₃) | N |
| I-1036 | | H | N(CH₃)₂ | OCH₃ | N |
| I-1037 | | H | N(CH₃)₂ | SCHF₂ | N |
| I-1038 | | H | NHCH₃ | OCH₃ | N |
| I-1039 | | H | OC₂H₅ | OC₂H₅ | N |
| I-1040 | | H | OCF₂CHF₂ | SCH₃ | N |
| I-1041 | | H | OCF₂CHFBr | SCH₃ | N |
| I-1042 | | H | OCF₂CHFCF₃ | SCH₃ | N |
| I-1043 | | H | OCH(CH₃)₂ | OCH₃ | N |
| I-1044 | | H | OCH(CH₃)₂ | SCH₃ | N |
| I-1045 | | H | OCH(CH₃)CH₂CH₃ | OCH₃ | N |
| I-1046 | | H | OCH₂CF₃ | OCF₂CHF₂ | N |
| I-1047 | | H | OCH₂CF₃ | OCH₃ | N |
| I-1048 | | H | OCH₂CHF₂ | OCH₃ | N |
| I-1049 | | H | OCH₃ | OC₂H₅ | N |
| I-1050 | | H | OCH₃ | OCF₂CHF₂ | N |
| I-1051 | | H | OCH₃ | OCF₂CHFBr | N |
| I-1052 | | H | OCH₃ | OCF₂CHFCF₃ | N |
| I-1053 | | H | OCH₃ | OCF₂CHFCl | N |
| I-1054 | | H | OCH₃ | OCH₃ | N |
| I-1055 | | H | OCH₃ | OCHF₂ | N |
| I-1056 | | H | OCH₃ | SCH(CH₃)₂ | N |
| I-1057 | | H | OCH₃ | SCH₃ | N |
| I-1058 | | H | OCH₃ | SCHF₂ | N |
| I-1059 | | CH₃ | CH₃ | CH₃ | CH |

TABLE 1-continued

| No. | R², R³, R⁴, R⁵ | R⁶ | X¹ | X² | Z |
|---|---|---|---|---|---|
| I-1060 | | CH₃ | CH₃ | Cl | CH |
| I-1061 | | CH₃ | CH₃ | OCH₃ | CH |
| I-1062 | | CH₃ | Cl | Cl | CH |
| I-1063 | | CH₃ | Cl | OCH₃ | CH |
| I-1064 | | CH₃ | OCH₃ | OCH₃ | CH |
| I-1065 | | CH₃ | CH₃ | CH₃ | N |
| I-1066 | | CH₃ | CH₃ | Cl | N |
| I-1067 | | CH₃ | CH₃ | OCH₃ | N |
| I-1068 | | CH₃ | Cl | Cl | N |
| I-1069 | | CH₃ | Cl | OCH₃ | N |
| I-1070 | | CH₃ | N(CH₃)₂ | OCH₃ | N |
| I-1071 | | CH₃ | OCH₂CH₂F | OCH₃ | N |
| I-1072 | | CH₃ | OCH₃ | OCH₃ | N |
| I-1073 | In I-1073– | H | CF₃ | OCH₃ | CH |
| I-1074 | I-1206, | H | CF₃ | OCHF₂ | CH |
| I-1075 | | H | CH(CH₃)₂ | OCH₃ | CH |
| I-1076 | R² = COPh | H | CH(OCH₃)₂ | CH₃ | CH |
| I-1077 | R³ = H | H | CH₂F | OCH₃ | CH |
| I-1078 | R⁴ = H | H | CH₂F | OCHF₂ | CH |
| I-1079 | R⁵ = H | H | CH₂OCH₃ | CH₃ | CH |
| I-1080 | | H | CH₂OCH₃ | OCH₃ | CH |
| I-1081 | | H | CH₂OCH₃ | OCHF₂ | CH |
| I-1082 | | H | CH₃ | CF₃ | CH |
| I-1083 | | H | CH₃ | CH₃ | CH |
| I-1084 | | H | CH₃ | Cl | CH |
| I-1085 | | H | CH₃ | F | CH |
| I-1086 | | H | CH₃ | H | CH |
| I-1087 | | H | CH₃ | OC₂H₅ | CH |
| I-1088 | | H | CH₃ | OCF₂CHF₂ | CH |
| I-1089 | | H | CH₃ | OCF₂CHFCF₃ | CH |
| I-1090 | | H | CH₃ | OCH₂CF₃ | CH |
| I-1091 | | H | CH₃ | OCH₂CH₂F | CH |
| I-1092 | | H | CH₃ | OCH₂CHF₂ | CH |
| I-1093 | | H | CH₃ | OCH₃ | CH |
| I-1094 | | H | CH₃ | OCHF₂ | CH |
| I-1095 | | H | CH₃ | SCH₃ | CH |
| I-1096 | | H | CHF₂ | CH₃ | CH |
| I-1097 | | H | Cl | Cl | CH |
| I-1098 | | H | Cl | H | CH |
| I-1099 | | H | Cl | N(CH₃)₂ | CH |
| I-1100 | | H | Cl | NH₂ | CH |
| I-1101 | | H | Cl | OC₂H₅ | CH |
| I-1102 | | H | Cl | OCF₂CHF₂ | CH |
| I-1103 | | H | Cl | OCF₂CHFCl | CH |
| I-1104 | | H | Cl | OCH₃ | CH |
| I-1105 | | H | Cl | OCHF₂ | CH |
| I-1106 | | H | N(CH₃)₂ | OCF₂CHF₂ | CH |
| I-1107 | | H | N(CH₃)₂ | OCH₃ | CH |
| I-1108 | | H | N(CH₃)₂ | OCHF₂ | CH |
| I-1109 | | H | N(CH₃)₂ | SCHF₂ | CH |
| I-1110 | | H | N(CH₃)C₂H₅ | OCHF₂ | CH |
| I-1111 | | H | N(CH₃)OCH₃ | OCHF₂ | CH |
| I-1112 | | H | NH₂ | OCH₃ | CH |
| I-1113 | | H | NHCH₃ | OCH₃ | CH |
| I-1114 | | H | NHCH₃ | OCHF₂ | CH |
| I-1115 | | H | OC₂H₅ | OC₂H₅ | CH |
| I-1116 | | H | OCF₂CHF₂ | SCH₃ | CH |
| I-1117 | | H | OCH(CH₃)₂ | OCHF₂ | CH |
| I-1118 | | H | OCH₂CF₃ | OCH₃ | CH |
| I-1119 | | H | OCH₂CH₂F | OCH₃ | CH |
| I-1120 | | H | OCH₂CHF₂ | OCH₃ | CH |
| I-1121 | | H | OCH₃ | OC₂H₅ | CH |
| I-1122 | | H | OCH₃ | OCF₂CHF₂ | CH |
| I-1123 | | H | OCH₃ | OCF₂CHFCF₃ | CH |
| I-1124 | | H | OCH₃ | OCH(CH₃)₂ | CH |
| I-1125 | | H | OCH₃ | OCH₃ | CH |
| I-1126 | | H | OCH₃ | SCH₃ | CH |
| I-1127 | | H | OCH₃ | SCHF₂ | CH |
| I-1128 | | H | OCHF₂ | OCH₂CF₃ | CH |
| I-1129 | | H | OCHF₂ | OCH₂CH₃ | CH |
| I-1130 | | H | OCHF₂ | OCH₃ | CH |
| I-1131 | | H | OCHF₂ | OCHF₂ | CH |
| I-1132 | | H | OCHF₂ | SCH₃ | CH |
| I-1133 | | H | C₂H₅ | OCH₃ | N |
| I-1134 | | H | C₂H₅ | SCH₃ | N |
| I-1135 | | H | CF₃ | OCH₃ | N |
| I-1136 | | H | CH(CH₃)₂ | CH₃ | N |

TABLE 1-continued

| No. | $R^2, R^3, R^4, R^5$ | $R^6$ | $X^1$ | $X^2$ | Z |
|---|---|---|---|---|---|
| I-1137 | | H | $CH(CH_3)_2$ | Cl | N |
| I-1138 | | H | $CH(CH_3)_2$ | $OCH_3$ | N |
| I-1139 | | H | $CH(CH_3)_2$ | $SCH_3$ | N |
| I-1140 | | H | $CH_2CF_3$ | $CH_3$ | N |
| I-1141 | | H | $CH_2F$ | $CH_3$ | N |
| I-1142 | | H | $CH_2F$ | $OCH_3$ | N |
| I-1143 | | H | $CH_2OCH_3$ | $CH_3$ | N |
| I-1144 | | H | $CH_2OCH_3$ | $OCH_3$ | N |
| I-1145 | | H | $CH_2SCH_3$ | $CH_3$ | N |
| I-1146 | | H | $CH_2SCH_3$ | Cl | N |
| I-1147 | | H | $CH_2SCH_3$ | $OC_2H_5$ | N |
| I-1148 | | H | $CH_2SCH_3$ | $OCH_3$ | N |
| I-1149 | | H | $CH_2SCH_3$ | $SCH_3$ | N |
| I-1150 | | H | $CH_3$ | $CF_3$ | N |
| I-1151 | | H | $CH_3$ | $CH_3$ | N |
| I-1152 | | H | $CH_3$ | Cl | N |
| I-1153 | | H | $CH_3$ | F | N |
| I-1154 | | H | $CH_3$ | H | N |
| I-1155 | | H | $CH_3$ | $OCH_2CF_3$ | N |
| I-1156 | | H | $CH_3$ | $OCH_2CH_2F$ | N |
| I-1157 | | H | $CH_3$ | $OCH_2CHF_2$ | N |
| I-1158 | | H | $CH_3$ | $OCH_3$ | N |
| I-1159 | | H | $CH_3$ | $SCH_3$ | N |
| I-1160 | | H | $CH_3$ | $SCHF_2$ | N |
| I-1161 | | H | $CHF_2$ | $CH_3$ | N |
| I-1162 | | H | $CHF_2$ | $OCH_3$ | N |
| I-1163 | | H | Cl | Cl | N |
| I-1164 | | H | Cl | $OCH(CH_3)_2$ | N |
| I-1165 | | H | Cl | $OCH_2CF_3$ | N |
| I-1166 | | H | Cl | $OCH_3$ | N |
| I-1167 | | H | Cl | $SCH_3$ | N |
| I-1168 | | H | F | $OCH_3$ | N |
| I-1169 | | H | H | $NH(CH_3)$ | N |
| I-1170 | | H | $N(CH_3)_2$ | $OCH_3$ | N |
| I-1171 | | H | $N(CH_3)_2$ | $SCHF_2$ | N |
| I-1172 | | H | $NHCH_3$ | $OCH_3$ | N |
| I-1173 | | H | $OC_2H_5$ | $OC_2H_5$ | N |
| I-1174 | | H | $OCF_2CHF_2$ | $SCH_3$ | N |
| I-1175 | | H | $OCF_2CHFBr$ | $SCH_3$ | N |
| I-1176 | | H | $OCF_2CHFCF_3$ | $SCH_3$ | N |
| I-1177 | | H | $OCH(CH_3)_2$ | $OCH_3$ | N |
| I-1178 | | H | $OCH(CH_3)_2$ | $SCH_3$ | N |
| I-1179 | | H | $OCH(CH_3)CH_2CH_3$ | $OCH_3$ | N |
| I-1180 | | H | $OCH_2CF_3$ | $OCF_2CHF_2$ | N |
| I-1181 | | H | $OCH_2CF_3$ | $OCH_3$ | N |
| I-1182 | | H | $OCH_2CHF_2$ | $OCH_3$ | N |
| I-1183 | | H | $OCH_3$ | $OC_2H_5$ | N |
| I-1184 | | H | $OCH_3$ | $OCF_2CHF_2$ | N |
| I-1185 | | H | $OCH_3$ | $OCF_2CHFBr$ | N |
| I-1186 | | H | $OCH_3$ | $OCF_2CHFCF_3$ | N |
| I-1187 | | H | $OCH_3$ | $OCF_2CHFCl$ | N |
| I-1188 | | H | $OCH_3$ | $OCH_3$ | N |
| I-1189 | | H | $OCH_3$ | $OCHF_2$ | N |
| I-1190 | | H | $OCH_3$ | $SCH(CH_3)_2$ | N |
| I-1191 | | H | $OCH_3$ | $SCH_3$ | N |
| I-1192 | | H | $OCH_3$ | $SCHF_2$ | N |
| I-1193 | | $CH_3$ | $CH_3$ | $CH_3$ | CH |
| I-1194 | | $CH_3$ | $CH_3$ | Cl | CH |
| I-1195 | | $CH_3$ | $CH_3$ | $OCH_3$ | CH |
| I-1196 | | $CH_3$ | Cl | Cl | CH |
| I-1197 | | $CH_3$ | Cl | $OCH_3$ | CH |
| I-1198 | | $CH_3$ | $OCH_3$ | $OCH_3$ | CH |
| I-1199 | | $CH_3$ | $CH_3$ | $CH_3$ | N |
| I-1200 | | $CH_3$ | $CH_3$ | Cl | N |
| I-1201 | | $CH_3$ | $CH_3$ | $OCH_3$ | N |
| I-1202 | | $CH_3$ | Cl | Cl | N |
| I-1203 | | $CH_3$ | Cl | $OCH_3$ | N |
| I-1204 | | $CH_3$ | $N(CH_3)_2$ | $OCH_3$ | N |
| I-1205 | | $CH_3$ | $OCH_2CH_2F$ | $OCH_3$ | N |
| I-1206 | | $CH_3$ | $OCH_3$ | $OCH_3$ | N |
| I-1207 | In I-1207– | H | $CF_3$ | $OCH_3$ | CH |
| I-1208 | I-1340, | H | $CF_3$ | $OCHF_2$ | CH |
| I-1209 | | H | $CH(CH_3)_2$ | $OCH_3$ | CH |
| I-1210 | $R^2 = COOCH_3$ | H | $CH(OCH_3)_2$ | $CH_3$ | CH |
| I-1211 | $R^3 = H$ | H | $CH_2F$ | $OCH_3$ | CH |
| I-1212 | $R^4 = H$ | H | $CH_2F$ | $OCHF_2$ | CH |
| I-1213 | $R^5 = H$ | H | $CH_2OCH_3$ | $CH_3$ | CH |

TABLE 1-continued

| No. | R², R³, R⁴, R⁵ | R⁶ | X¹ | X² | Z |
|---|---|---|---|---|---|
| I-1214 | | H | CH₂OCH₃ | OCH₃ | CH |
| I-1215 | | H | CH₂OCH₃ | OCHF₂ | CH |
| I-1216 | | H | CH₃ | CF₃ | CH |
| I-1217 | | H | CH₃ | CH₃ | CH |
| I-1218 | | H | CH₃ | Cl | CH |
| I-1219 | | H | CH₃ | F | CH |
| I-1220 | | H | CH₃ | H | CH |
| I-1221 | | H | CH₃ | OC₂H₅ | CH |
| I-1222 | | H | CH₃ | OCF₂CHF₂ | CH |
| I-1223 | | H | CH₃ | OCF₂CHFCF₃ | CH |
| I-1224 | | H | CH₃ | OCH₂CF₃ | CH |
| I-1225 | | H | CH₃ | OCH₂CH₂F | CH |
| I-1226 | | H | CH₃ | OCH₂CHF₂ | CH |
| I-1227 | | H | CH₃ | OCH₃ | CH |
| I-1228 | | H | CH₃ | OCHF₂ | CH |
| I-1229 | | H | CH₃ | SCH₃ | CH |
| I-1230 | | H | CHF₂ | CH₃ | CH |
| I-1231 | | H | Cl | Cl | CH |
| I-1232 | | H | Cl | H | CH |
| I-1233 | | H | Cl | N(CH₃)₂ | CH |
| I-1234 | | H | Cl | NH₂ | CH |
| I-1235 | | H | Cl | OC₂H₅ | CH |
| I-1236 | | H | Cl | OCF₂CHF₂ | CH |
| I-1237 | | H | Cl | OCF₂CHFCl | CH |
| I-1238 | | H | Cl | OCH₃ | CH |
| I-1239 | | H | Cl | OCHF₂ | CH |
| I-1240 | | H | N(CH₃)₂ | OCF₂CHF₂ | CH |
| I-1241 | | H | N(CH₃)₂ | OCH₃ | CH |
| I-1242 | | H | N(CH₃)₂ | OCHF₂ | CH |
| I-1243 | | H | N(CH₃)₂ | SCHF₂ | CH |
| I-1244 | | H | N(CH₃)C₂H₅ | OCHF₂ | CH |
| I-1245 | | H | N(CH₃)OCH₃ | OCHF₂ | CH |
| I-1246 | | H | NH₂ | OCH₃ | CH |
| I-1247 | | H | NHCH₃ | OCH₃ | CH |
| I-1248 | | H | NHCH₃ | OCHF₂ | CH |
| I-1249 | | H | OC₂H₅ | OC₂H₅ | CH |
| I-1250 | | H | OCF₂CHF₂ | SCH₃ | CH |
| I-1251 | | H | OCH(CH₃)₂ | OCHF₂ | CH |
| I-1252 | | H | OCH₂CF₃ | OCH₃ | CH |
| I-1253 | | H | OCH₂CH₂F | OCH₃ | CH |
| I-1254 | | H | OCH₂CHF₂ | OCH₃ | CH |
| I-1255 | | H | OCH₃ | OC₂H₅ | CH |
| I-1256 | | H | OCH₃ | OCF₂CHF₂ | CH |
| I-1257 | | H | OCH₃ | OCF₂CHFCF₃ | CH |
| I-1258 | | H | OCH₃ | OCH(CH₃)₂ | CH |
| I-1259 | | H | OCH₃ | OCH₃ | CH |
| I-1260 | | H | OCH₃ | SCH₃ | CH |
| I-1261 | | H | OCH₃ | SCHF₂ | CH |
| I-1262 | | H | OCHF₂ | OCH₂CF₃ | CH |
| I-1263 | | H | OCHF₂ | OCH₂CH₃ | CH |
| I-1264 | | H | OCHF₂ | OCH₃ | CH |
| I-1265 | | H | OCHF₂ | OCHF₂ | CH |
| I-1266 | | H | OCHF₂ | SCH₃ | CH |
| I-1267 | | H | C₂H₅ | OCH₃ | N |
| I-1268 | | H | C₂H₅ | SCH₃ | N |
| I-1269 | | H | CF₃ | OCH₃ | N |
| I-1270 | | H | CH(CH₃)₂ | CH₃ | N |
| I-1271 | | H | CH(CH₃)₂ | Cl | N |
| I-1272 | | H | CH(CH₃)₂ | OCH₃ | N |
| I-1273 | | H | CH(CH₃)₂ | SCH₃ | N |
| I-1274 | | H | CH₂CF₃ | CH₃ | N |
| I-1275 | | H | CH₂F | CH₃ | N |
| I-1276 | | H | CH₂F | OCH₃ | N |
| I-1277 | | H | CH₂OCH₃ | CH₃ | N |
| I-1278 | | H | CH₂OCH₃ | OCH₃ | N |
| I-1279 | | H | CH₂SCH₃ | CH₃ | N |
| I-1280 | | H | CH₂SCH₃ | Cl | N |
| I-1281 | | H | CH₂SCH₃ | OC₂H₅ | N |
| I-1282 | | H | CH₂SCH₃ | OCH₃ | N |
| I-1283 | | H | CH₂SCH₃ | SCH₃ | N |
| I-1284 | | H | CH₃ | CF₃ | N |
| I-1285 | | H | CH₃ | CH₃ | N |
| I-1286 | | H | CH₃ | Cl | N |
| I-1287 | | H | CH₃ | F | N |
| I-1288 | | H | CH₃ | H | N |
| I-1289 | | H | CH₃ | OCH₂CF₃ | N |
| I-1290 | | H | CH₃ | OCH₂CH₂F | N |

TABLE 1-continued

| No. | $R^2, R^3, R^4, R^5$ | $R^6$ | $X^1$ | $X^2$ | Z |
|---|---|---|---|---|---|
| I-1291 | | H | $CH_3$ | $OCH_2CHF_2$ | N |
| I-1292 | | H | $CH_3$ | $OCH_3$ | N |
| I-1293 | | H | $CH_3$ | $SCH_3$ | N |
| I-1294 | | H | $CH_3$ | $SCHF_2$ | N |
| I-1295 | | H | $CHF_2$ | $CH_3$ | N |
| I-1296 | | H | $CHF_2$ | $OCH_3$ | N |
| I-1297 | | H | Cl | Cl | N |
| I-1298 | | H | Cl | $OCH(CH_3)_2$ | N |
| I-1299 | | H | Cl | $OCH_2CF_3$ | N |
| I-1300 | | H | Cl | $OCH_3$ | N |
| I-1301 | | H | Cl | $SCH_3$ | N |
| I-1302 | | H | F | $OCH_3$ | N |
| I-1303 | | H | H | $NH(CH_3)$ | N |
| I-1304 | | H | $N(CH_3)_2$ | $OCH_3$ | N |
| I-1305 | | H | $N(CH_3)_2$ | $SCHF_2$ | N |
| I-1306 | | H | $NHCH_3$ | $OCH_3$ | N |
| I-1307 | | H | $OC_2H_5$ | $OC_2H_5$ | N |
| I-1308 | | H | $OCF_2CHF_2$ | $SCH_3$ | N |
| I-1309 | | H | $OCF_2CHFBr$ | $SCH_3$ | N |
| I-1310 | | H | $OCF_2CHFCF_3$ | $SCH_3$ | N |
| I-1311 | | H | $OCH(CH_3)_2$ | $OCH_3$ | N |
| I-1312 | | H | $OCH(CH_3)_2$ | $SCH_3$ | N |
| I-1313 | | H | $OCH(CH_3)CH_2CH_3$ | $OCH_3$ | N |
| I-1314 | | H | $OCH_2CF_3$ | $OCF_2CHF_2$ | N |
| I-1315 | | H | $OCH_2CF_3$ | $OCH_3$ | N |
| I-1316 | | H | $OCH_2CHF_2$ | $OCH_3$ | N |
| I-1317 | | H | $OCH_3$ | $OC_2H_5$ | N |
| I-1318 | | H | $OCH_3$ | $OCF_2CHF_2$ | N |
| I-1319 | | H | $OCH_3$ | $OCF_2CHFBr$ | N |
| I-1320 | | H | $OCH_3$ | $OCF_2CHFCF_3$ | N |
| I-1321 | | H | $OCH_3$ | $OCF_2CHFCl$ | N |
| I-1322 | | H | $OCH_3$ | $OCH_3$ | N |
| I-1323 | | H | $OCH_3$ | $OCHF_2$ | N |
| I-1324 | | H | $OCH_3$ | $SCH(CH_3)_2$ | N |
| I-1325 | | H | $OCH_3$ | $SCH_3$ | N |
| I-1326 | | H | $OCH_3$ | $SCHF_2$ | N |
| I-1327 | | $CH_3$ | $CH_3$ | $CH_3$ | CH |
| I-1328 | | $CH_3$ | $CH_3$ | Cl | CH |
| I-1329 | | $CH_3$ | $CH_3$ | $OCH_3$ | CH |
| I-1330 | | $CH_3$ | Cl | Cl | CH |
| I-1331 | | $CH_3$ | Cl | $OCH_3$ | CH |
| I-1332 | | $CH_3$ | $OCH_3$ | $OCH_3$ | CH |
| I-1333 | | $CH_3$ | $CH_3$ | $CH_3$ | N |
| I-1334 | | $CH_3$ | $CH_3$ | Cl | N |
| I-1335 | | $CH_3$ | $CH_3$ | $OCH_3$ | N |
| I-1336 | | $CH_3$ | Cl | Cl | N |
| I-1337 | | $CH_3$ | Cl | $OCH_3$ | N |
| I-1338 | | $CH_3$ | $N(CH_3)_2$ | $OCH_3$ | N |
| I-1339 | | $CH_3$ | $OCH_2CH_2F$ | $OCH_3$ | N |
| I-1340 | | $CH_3$ | $OCH_3$ | $OCH_3$ | N |
| I-1341 | In I-1341– | H | $CF_3$ | $OCH_3$ | CH |
| I-1342 | I-1474, | H | $CF_3$ | $OCHF_2$ | CH |
| I-1343 | | H | $CH(CH_3)_2$ | $OCH_3$ | CH |
| I-1344 | $R^2 = CON(CH_3)_2$ | H | $CH(OCH_3)_2$ | $CH_3$ | CH |
| I-1345 | $R^3 = H$ | H | $CH_2F$ | $OCH_3$ | CH |
| I-1346 | $R^4 = H$ | H | $CH_2F$ | $OCHF_2$ | CH |
| I-1347 | $R^5 = H$ | H | $CH_2OCH_3$ | $CH_3$ | CH |
| I-1348 | | H | $CH_2OCH_3$ | $OCH_3$ | CH |
| I-1349 | | H | $CH_2OCH_3$ | $OCHF_2$ | CH |
| I-1350 | | H | $CH_3$ | $CF_3$ | CH |
| I-1351 | | H | $CH_3$ | $CH_3$ | CH |
| I-1352 | | H | $CH_3$ | Cl | CH |
| I-1353 | | H | $CH_3$ | F | CH |
| I-1354 | | H | $CH_3$ | H | CH |
| I-1355 | | H | $CH_3$ | $OC_2H_5$ | CH |
| I-1356 | | H | $CH_3$ | $OCF_2CHF_2$ | CH |
| I-1357 | | H | $CH_3$ | $OCF_2CHFCF_3$ | CH |
| I-1358 | | H | $CH_3$ | $OCH_2CF_3$ | CH |
| I-1359 | | H | $CH_3$ | $OCH_2CH_2F$ | CH |
| I-1360 | | H | $CH_3$ | $OCH_2CHF_2$ | CH |
| I-1361 | | H | $CH_3$ | $OCH_3$ | CH |
| I-1362 | | H | $CH_3$ | $OCHF_2$ | CH |
| I-1363 | | H | $CH_3$ | $SCH_3$ | CH |
| I-1364 | | H | $CHF_2$ | $CH_3$ | CH |
| I-1365 | | H | Cl | Cl | CH |
| I-1366 | | H | Cl | H | CH |
| I-1367 | | H | Cl | $N(CH_3)_2$ | CH |

TABLE 1-continued

| No. | R², R³, R⁴, R⁵ | R⁶ | X¹ | X² | Z |
|---|---|---|---|---|---|
| I-1368 | | H | Cl | NH₂ | CH |
| I-1369 | | H | Cl | OC₂H₅ | CH |
| I-1370 | | H | Cl | OCF₂CHF₂ | CH |
| I-1371 | | H | Cl | OCF₂CHFCl | CH |
| I-1372 | | H | Cl | OCH₃ | CH |
| I-1373 | | H | Cl | OCHF₂ | CH |
| I-1374 | | H | N(CH₃)₂ | OCF₂CHF₂ | CH |
| I-1375 | | H | N(CH₃)₂ | OCH₃ | CH |
| I-1376 | | H | N(CH₃)₂ | OCHF₂ | CH |
| I-1377 | | H | N(CH₃)₂ | SCHF₂ | CH |
| I-1378 | | H | N(CH₃)C₂H₅ | OCHF₂ | CH |
| I-1379 | | H | N(CH₃)OCH₃ | OCHF₂ | CH |
| I-1380 | | H | NH₂ | OCH₃ | CH |
| I-1381 | | H | NHCH₃ | OCH₃ | CH |
| I-1382 | | H | NHCH₃ | OCHF₂ | CH |
| I-1383 | | H | OC₂H₅ | OC₂H₅ | CH |
| I-1384 | | H | OCF₂CHF₂ | SCH₃ | CH |
| I-1385 | | H | OCH(CH₃)₂ | OCHF₂ | CH |
| I-1386 | | H | OCH₂CF₃ | OCH₃ | CH |
| I-1387 | | H | OCH₂CH₂F | OCH₃ | CH |
| I-1388 | | H | OCH₂CHF₂ | OCH₃ | CH |
| I-1389 | | H | OCH₃ | OC₂H₅ | CH |
| I-1390 | | H | OCH₃ | OCF₂CHF₂ | CH |
| I-1391 | | H | OCH₃ | OCF₂CHFCF₃ | CH |
| I-1392 | | H | OCH₃ | OCH(CH₃)₂ | CH |
| I-1393 | | H | OCH₃ | OCH₃ | CH |
| I-1394 | | H | OCH₃ | SCH₃ | CH |
| I-1395 | | H | OCH₃ | SCHF₂ | CH |
| I-1396 | | H | OCHF₂ | OCH₂CF₃ | CH |
| I-1397 | | H | OCHF₂ | OCH₂CH₃ | CH |
| I-1398 | | H | OCHF₂ | OCH₃ | CH |
| I-1399 | | H | OCHF₂ | OCHF₂ | CH |
| I-1400 | | H | OCHF₂ | SCH₃ | CH |
| I-1401 | | H | C₂H₅ | OCH₃ | N |
| I-1402 | | H | C₂H₅ | SCH₃ | N |
| I-1403 | | H | CF₃ | OCH₃ | N |
| I-1404 | | H | CH(CH₃)₂ | CH₃ | N |
| I-1405 | | H | CH(CH₃)₂ | Cl | N |
| I-1406 | | H | CH(CH₃)₂ | OCH₃ | N |
| I-1407 | | H | CH(CH₃)₂ | SCH₃ | N |
| I-1408 | | H | CH₂CF₃ | CH₃ | N |
| I-1409 | | H | CH₂F | CH₃ | N |
| I-1410 | | H | CH₂F | OCH₃ | N |
| I-1411 | | H | CH₂OCH₃ | CH₃ | N |
| I-1412 | | H | CH₂OCH₃ | OCH₃ | N |
| I-1413 | | H | CH₂SCH₃ | CH₃ | N |
| I-1414 | | H | CH₂SCH₃ | Cl | N |
| I-1415 | | H | CH₂SCH₃ | OC₂H₅ | N |
| I-1416 | | H | CH₂SCH₃ | OCH₃ | N |
| I-1417 | | H | CH₂SCH₃ | SCH₃ | N |
| I-1418 | | H | CH₃ | CF₃ | N |
| I-1419 | | H | CH₃ | CH₃ | N |
| I-1420 | | H | CH₃ | Cl | N |
| I-1421 | | H | CH₃ | F | N |
| I-1422 | | H | CH₃ | H | N |
| I-1423 | | H | CH₃ | OCH₂CF₃ | N |
| I-1424 | | H | CH₃ | OCH₂CH₂F | N |
| I-1425 | | H | CH₃ | OCH₂CHF₂ | N |
| I-1426 | | H | CH₃ | OCH₃ | N |
| I-1427 | | H | CH₃ | SCH₃ | N |
| I-1428 | | H | CH₃ | SCHF₂ | N |
| I-1429 | | H | CHF₂ | CH₃ | N |
| I-1430 | | H | CHF₂ | OCH₃ | N |
| I-1431 | | H | Cl | Cl | N |
| I-1432 | | H | Cl | OCH(CH₃)₂ | N |
| I-1433 | | H | Cl | OCH₂CF₃ | N |
| I-1434 | | H | Cl | OCH₃ | N |
| I-1435 | | H | Cl | SCH₃ | N |
| I-1436 | | H | F | OCH₃ | N |
| I-1437 | | H | H | NH(CH₃) | N |
| I-1438 | | H | N(CH₃)₂ | OCH₃ | N |
| I-1439 | | H | N(CH₃)₂ | SCHF₂ | N |
| I-1440 | | H | NHCH₃ | OCH₃ | N |
| I-1441 | | H | OC₂H₅ | OC₂H₅ | N |
| I-1442 | | H | OCF₂CHF₂ | SCH₃ | N |
| I-1443 | | H | OCF₂CHFBr | SCH₃ | N |
| I-1444 | | H | OCF₂CHFCF₃ | SCH₃ | N |

TABLE 1-continued

| No. | R², R³, R⁴, R⁵ | R⁶ | X¹ | X² | Z |
|---|---|---|---|---|---|
| I-1445 | | H | OCH(CH₃)₂ | OCH₃ | N |
| I-1446 | | H | OCH(CH₃)₂ | SCH₃ | N |
| I-1447 | | H | OCH(CH₃)CH₂CH₃ | OCH₃ | N |
| I-1448 | | H | OCH₂CF₃ | OCF₂CHF₂ | N |
| I-1449 | | H | OCH₂CF₃ | OCH₃ | N |
| I-1450 | | H | OCH₂CHF₂ | OCH₃ | N |
| I-1451 | | H | OCH₃ | OC₂H₅ | N |
| I-1452 | | H | OCH₃ | OCF₂CHF₂ | N |
| I-1453 | | H | OCH₃ | OCF₂CHFBr | N |
| I-1454 | | H | OCH₃ | OCF₂CHFCF₃ | N |
| I-1455 | | H | OCH₃ | OCF₂CHFCl | N |
| I-1456 | | H | OCH₃ | OCH₃ | N |
| I-1457 | | H | OCH₃ | OCHF₂ | N |
| I-1458 | | H | OCH₃ | SCH(CH₃)₂ | N |
| I-1459 | | H | OCH₃ | SCH₃ | N |
| I-1460 | | H | OCH₃ | SCHF₂ | N |
| I-1461 | | CH₃ | CH₃ | CH₃ | CH |
| I-1462 | | CH₃ | CH₃ | Cl | CH |
| I-1463 | | CH₃ | CH₃ | OCH₃ | CH |
| I-1464 | | CH₃ | Cl | Cl | CH |
| I-1465 | | CH₃ | Cl | OCH₃ | CH |
| I-1466 | | CH₃ | OCH₃ | OCH₃ | CH |
| I-1467 | | CH₃ | CH₃ | CH₃ | N |
| I-1468 | | CH₃ | CH₃ | Cl | N |
| I-1469 | | CH₃ | CH₃ | OCH₃ | N |
| I-1470 | | CH₃ | Cl | Cl | N |
| I-1471 | | CH₃ | Cl | OCH₃ | N |
| I-1472 | | CH₃ | N(CH₃)₂ | OCH₃ | N |
| I-1473 | | CH₃ | OCH₂CH₂F | OCH₃ | N |
| I-1474 | | CH₃ | OCH₃ | OCH₃ | N |

TABLE 2

| No. | R² R³ R⁴ R⁵ | R⁶ | X¹ X² Z |
|---|---|---|---|
| I-1475 | In I-1475–I-1488, | C₂H₅ | In I-1475–I-1483 |
| I-1476 | R² = COCH₃ | i-C₃H₇ | X¹ = OCH₃ |
|  | R³ = H |  | X² = OCH₃ |
| I-1477 | R⁴ = H | (CH₂)₃OCH₃ | Z = CH |
|  | R⁵ = H |  |  |
| I-1478 |  | CH₂CH=CHCH₃ |  |
| I-1479 |  | CH₂CH=CCl₂ |  |
| I-1480 |  | CH₂CCH |  |
| I-1481 |  | CH₂Ph |  |
| I-1482 |  | CH₂(Ph-4-Cl) |  |
| I-1483 |  | CH₂(Ph-4-CH₃) |  |
| I-1484 |  | C₂H₅ | In I-1484–I-1488 |
| I-1485 |  | CH₂CH=CHCH₃ | X¹ = CH₃ |
|  |  |  | X² = OCH₃ |
| I-1486 |  | CH₂Ph | Z = CH |
| I-1487 |  | CH₂(Ph-4-Cl) |  |
| I-1488 |  | CH₂(Ph-4-CH₃) |  |

TABLE 3

| No. | R² R³ R⁴ R⁵ | R⁶ X¹ X² Z |
|---|---|---|
| I-1489 | R² = Cl | In I-1489–I-1541 |
|  | R³ = R⁴ = R⁵ = H |  |
| I-1490 | R² = CH₃ | R⁶ = H |
|  | R³ = R⁴ = R⁵ = H | X¹ = OCH₃ |
|  |  | X² = OCH₃ |
|  |  | Z = CH |
| I-1491 | R² = CH₂CH=CHCH₃ |  |
|  | R³ = R⁴ = R⁵ = H |  |
| I-1492 | R² = CH₂CH=CCl₂ |  |
|  | R³ = R⁴ = R⁵ = H |  |
| I-1493 | R² = CH₂CCH |  |
|  | R³ = R⁴ = R⁵ = H |  |
| I-1494 | R² = Ph |  |
|  | R³ = R⁴ = R⁵ = H |  |
| I-1495 | R² = Ph-4-Cl |  |

TABLE 3-continued

| No. | R² R³ R⁴ R⁵ | R⁶ X¹ X² Z |
|---|---|---|
|  | R³ = R⁴ = R⁵ = H |  |
| I-1496 | R² = Ph-4-CH₃ |  |
|  | R³ = R⁴ = R⁵ = H |  |
| I-1497 | R² = CH₂Ph |  |
|  | R³ = R⁴ = R⁵ = H |  |
| I-1498 | R² = CH₂(Ph-4-Cl) |  |
|  | R³ = R⁴ = R⁵ = H |  |
| I-1499 | R² = CH₂(Ph-4-CH₃) |  |
|  | R³ = R⁴ = R⁵ = H |  |
| I-1500 | R² = COCH=CHCH₃ |  |
|  | R³ = R⁴ = R⁵ = H |  |
| I-1501 | R² = COOCH₂CF₃ |  |
|  | R³ = R⁴ = R⁵ = H |  |
| I-1502 | R² = COOCH₂CH₂F |  |
|  | R³ = R⁴ = R⁵ = H |  |
| I-1503 | R² = COOCH₂CH₂OCH₃ |  |
|  | R³ = R⁴ = R⁵ = H |  |
| I-1504 | R² = COOCH₂CH=CHCH₃ |  |
|  | R³ = R⁴ = R⁵ = H |  |
| I-1505 | R² = COOCH₂CH=CCl₂ |  |
|  | R³ = R⁴ = R⁵ = H |  |
| I-1506 | R² = COOC₂CCH |  |
|  | R³ = R⁴ = R⁵ = H |  |
| I-1507 | R² = CO(Ph-4-Cl) |  |
|  | R³ = R⁴ = R⁵ = H |  |
| I-1508 | R² = CO(Ph-4-CH₃) |  |
|  | R³ = R⁴ = R⁵ = H |  |
| I-1509 | R² = COCH₂Ph |  |
|  | R³ = R⁴ = R⁵ = H |  |
| I-1510 | R² = COCH₂(Ph-4-Cl) |  |
|  | R³ = R⁴ = R⁵ = H |  |
| I-1511 | R² = COCH₂(Ph-4-CH₃) |  |
|  | R³ = R⁴ = R⁵ = H |  |
| I-1512 | R² = H    R⁴ = H |  |
|  | R³ = Br   R⁵ = H |  |
| I-1513 | R² = H    R⁴ = H |  |
|  | R³ = CH₃  R⁵ = H |  |
| I-1514 | R² = H    R⁴ = H |  |
|  | R³ = CH₂CF₃  R⁵ = H |  |

TABLE 3-continued

| No. | R² R³ R⁴ R⁵ | | R⁶ X¹ X² Z |
|---|---|---|---|
| I-1515 | R² = H<br>R³ = CH₂Ph | R⁴ = H<br>R⁵ = H | |
| I-1516 | R² = H<br>R³ = COCH₃ | R⁴ = H<br>R⁵ = H | |
| I-1517 | R² = R⁴ = R⁵ = H<br>R³ = CO—cyc—Pr | | |
| I-1518 | R² = H<br>R³ = COCF₃ | R⁴ = H<br>R⁵ = H | |
| I-1519 | R² = R⁴ = R⁵ = H<br>R³ = CON(CH₃)₂ | | |
| I-1520 | R² = H<br>R³ = COOCH₃ | R⁴ = H<br>R⁵ = H | |
| I-1521 | R² = R⁴ = R⁵ = H<br>R³ = COOCH₂CH₂F | | |
| I-1522 | R² = H<br>R³ = COPh | R⁴ = H<br>R⁵ = H | |
| I-1523 | R² = H<br>R³ = COCH₂Ph | R⁴ = H<br>R⁵ = H | |
| I-1524 | R² = H<br>R³ = CH₂CF₃ | R⁴ = H<br>R⁵ = H | |
| I-1525 | R² = H<br>R³ = CH₂Ph | R⁴ = H<br>R⁵ = H | |
| I-1526 | R² = H<br>R³ = COCH₃ | R⁴ = H<br>R⁵ = H | |
| I-1527 | R² = R⁴ = R⁵ = H<br>R³ = CO—cyc—Pr | | |
| I-1528 | R² = H<br>R³ = COCF₃ | R⁴ = H<br>R⁵ = H | |
| I-1529 | R² = R⁴ = R⁵ = H<br>R³ = CON(CH₃)₂ | | |
| I-1530 | R² = H<br>R³ = COOCH₃ | R⁴ = H<br>R⁵ = H | |
| I-1531 | R² = R⁴ = R⁵ = H<br>R³ = COOCH₂CH₂F | | |
| I-1532 | R² = CH₃<br>R³ = Br | R⁴ = H<br>R⁵ = CH₃ | |
| I-1533 | R² = CH₃<br>R³ = COCH₃ | R⁴ = H<br>R⁵ = CH₃ | |
| I-1534 | R² = CH₃<br>R³ = COC₂H₅ | R⁴ = H<br>R⁵ = CH₃ | |
| I-1535 | R² = CH₃<br>R³ = COOCH₃ | R⁴ = H<br>R⁵ = CH₃ | |
| I-1536 | R² = COCH₃<br>R³ = H | R⁴ = H<br>R⁵ = Br | |
| I-1537 | R² = COC₂H₅<br>R³ = H | R⁴ = H<br>R⁵ = Br | |
| I-1538 | R² = COPh<br>R³ = H | R⁴ = H<br>R⁵ = Br | |
| I-1539 | R² = COCH₃<br>R³ = H | R⁴ = H<br>R⁵ = CH₃ | |
| I-1540 | R² = COC₂H₅<br>R³ = H | R⁴ = H<br>R⁵ = CH₃ | |
| I-1541 | R² = COPh<br>R³ = H | R⁴ = H<br>R⁵ = CH₃ | |
| I-1542 | R² = Cl<br>R³ = R⁴ = R⁵ = H | | In I-1542–I-1594<br>R⁶ = H<br>X¹ = CH₃<br>X² = OCH₃<br>Z = CH |
| I-1543 | R² = CH₃<br>R³ = R⁴ = R⁵ = H | | |
| I-1544 | R² = CH₂CH=CHCH₃<br>R³ = R⁴ = R⁵ = H | | |
| I-1545 | R² = CH₂CH=CCl₂<br>R³ = R⁴ = R⁵ = H | | |
| I-1546 | R² = CH₂CCH<br>R³ = R⁴ = R⁵ = H | | |
| I-1547 | R² = Ph<br>R³ = R⁴ = R⁵ = H | | |
| I-1548 | R² = Ph-4-Cl<br>R³ = R⁴ = R⁵ = H | | |
| I-1549 | R² = Ph-4-CH₃<br>R³ = R⁴ = R⁵ = H | | |
| I-1550 | R² = CH₂Ph<br>R³ = R⁴ = R⁵ = H | | |
| I-1551 | R² = CH₂(Ph-4-Cl)<br>R³ = R⁴ = R⁵ = H | | |
| I-1552 | R² = CH₂(Ph-4-CH₃)<br>R³ = R⁴ = R⁵ = H | | |
| I-1553 | R² = COCH=CHCH₃<br>R³ = R⁴ = R⁵ = H | | |
| I-1554 | R² = COOCH₂CF₃<br>R³ = R⁴ = R⁵ = H | | |
| I-1555 | R² = COOCH₂CH₂F<br>R³ = R⁴ = R⁵ = H | | |
| I-1556 | R² = COOCH₂CH₂OCH₃<br>R³ = R⁴ = R⁵ = H | | |
| I-1557 | R² = COOCH₂CH=CHCH₃<br>R³ = R⁴ = R⁵ = H | | |
| I-1558 | R² = COOCH₂CH=CCl₂<br>R³ = R⁴ = R⁵ = H | | |
| I-1559 | R² = COOC₂CCH<br>R³ = R⁴ = R⁵ = H | | |
| I-1560 | R² = CO(Ph-4-Cl)<br>R³ = R⁴ = R⁵ = H | | |
| I-1561 | R² = CO(Ph-4-CH₃)<br>R³ = R⁴ = R⁵ = H | | |
| I-1562 | R² = COCH₂Ph<br>R³ = R⁴ = R⁵ = H | | |
| I-1563 | R² = COCH₂(Ph-4-Cl)<br>R³ = R⁴ = R⁵ = H | | |
| I-1564 | R² = COCH₂(Ph-4-CH₃)<br>R³ = R⁴ = R⁵ = H | | |
| I-1565 | R² = H<br>R³ = Br | R⁴ = H<br>R⁵ = H | |
| I-1566 | R² = H<br>R³ = CH₃ | R⁴ = H<br>R⁵ = H | |
| I-1567 | R² = H<br>R³ = CH₂CF₃ | R⁴ = H<br>R⁵ = H | |
| I-1568 | R² = H<br>R³ = CH₂Ph | R⁴ = H<br>R⁵ = H | |
| I-1569 | R² = H<br>R³ = COCH₃ | R⁴ = H<br>R⁵ = H | |
| I-1570 | R² = R⁴ = R⁵ = H<br>R³ = CO—cyc—Pr | | |
| I-1571 | R² = H<br>R³ = COCF₃ | R⁴ = H<br>R⁵ = H | |
| I-1572 | R² = R⁴ = R⁵ = H<br>R³ = CON(CH₃)₂ | | |
| I-1573 | R² = H<br>R³ = COOCH₃ | R⁴ = H<br>R⁵ = H | |
| I-1574 | R² = R⁴ = R⁵ = H<br>R³ = COOCH₂CH₂F | | |
| I-1575 | R² = H<br>R³ = COPh | R⁴ = H<br>R⁵ = H | |
| I-1576 | R² = H<br>R³ = COCH₂Ph | R⁴ = H<br>R⁵ = H | |
| I-1577 | R² = H<br>R³ = CH₂CF₃ | R⁴ = H<br>R⁵ = H | |
| I-1578 | R² = H<br>R³ = CH₂Ph | R⁴ = H<br>R⁵ = H | |
| I-1579 | R² = H<br>R³ = COCH₃ | R⁴ = H<br>R⁵ = H | |
| I-1580 | R² = R⁴ = R⁵ = H<br>R³ = CO—cyc—Pr | | |
| I-1581 | R² = H<br>R³ = COCF₃ | R⁴ = H<br>R⁵ = H | |
| I-1582 | R² = R⁴ = R⁵ = H<br>R³ = CON(CH₃)₂ | | |
| I-1583 | R² = H<br>R³ = COOCH₃ | R⁴ = H<br>R⁵ = H | |
| I-1584 | R² = R⁴ = R⁵ = H<br>R³ = COOCH₂CH₂F | | |
| I-1585 | R² = CH₃<br>R³ = Br | R⁴ = H<br>R⁵ = CH₃ | |
| I-1586 | R² = CH₃<br>R³ = COCH₃ | R⁴ = H<br>R⁵ = CH₃ | |
| I-1587 | R² = CH₃<br>R³ = COC₂H₅ | R⁴ = H<br>R⁵ = CH₃ | |
| I-1588 | R² = CH₃<br>R³ = COOCH₃ | R⁴ = H<br>R⁵ = CH₃ | |
| I-1589 | R² = COCH₃<br>R³ = H | R⁴ = H<br>R⁵ = CH₃ | |
| I-1590 | R² = COC₂H₅<br>R³ = H | R⁴ = H<br>R⁵ = Br | |

TABLE 3-continued

| No. | $R^2$ $R^3$ $R^4$ $R^5$ | $R^6$ $X^1$ $X^2$ Z |
|---|---|---|
| I-1591 | $R^2$ = COPh<br>$R^3$ = H | $R^4$ = H<br>$R^5$ = Br |
| I-1592 | $R^2$ = COCH$_3$<br>$R^3$ = H | $R^4$ = H<br>$R^5$ = CH$_3$ |
| I-1593 | $R^2$ = COC$_2$H$_5$<br>$R^3$ = H | $R^4$ = H<br>$R^5$ = CH$_3$ |
| I-1594 | $R^2$ = COPh<br>$R^3$ = H | $R^4$ = H<br>$R^5$ = CH$_3$ |

TABLE 4

| No. | $R^2$<br>$R^3$<br>$R^4$<br>$R^5$ | $R^6$<br>$X^1$<br>$X^2$<br>Z |
|---|---|---|
| I-1595 | $R^2$ = Cl<br>$R^3$ = $R^4$ = $R^5$ = H | $R^6$ = H<br>$X^1$ = CH$_3$<br>$X^2$ = CH$_3$<br>Z = CH |
| I-1596 | $R^2$ = CH$_3$<br>$R^3$ = $R^4$ = $R^5$ = H | $R^6$ = H<br>$X^1$ = CH$_3$<br>$X^2$ = Cl<br>Z = CH |
| I-1597 | $R^2$ = CH$_2$CH=CHCH$_3$<br>$R^3$ = $R^4$ = $R^5$ = H | $R^6$ = CH$_3$<br>$X^1$ = CH$_3$<br>$X^2$ = OCH$_3$<br>Z = CH |
| I-1598 | $R^2$ = CH$_2$CH=CCl$_2$<br>$R^3$ = $R^4$ = $R^5$ = H | $R^6$ = H<br>$X^1$ = Cl<br>$X^2$ = Cl<br>Z = CH |
| I-1599 | $R^2$ = CH$_2$CCH<br>$R^3$ = $R^4$ = $R^5$ = H | $R^6$ = H<br>$X^1$ = Cl<br>$X^2$ = OCH$_3$<br>Z = CH |
| I-1600 | $R^2$ = Ph<br>$R^3$ = $R^4$ = $R^5$ = H | $R^6$ = CH$_3$<br>$X^1$ = OCH$_3$<br>$X^2$ = OCH$_3$<br>Z = CH |
| I-1601 | $R^2$ = (Ph-4-Cl)<br>$R^3$ = $R^4$ = $R^5$ = H | $R^6$ = H<br>$X^1$ = CH$_3$<br>$X^2$ = CH$_3$<br>Z = N |
| I-1602 | $R^2$ = (Ph-4-CH$_3$)<br>$R^3$ = $R^4$ = $R^5$ = H | $R^6$ = H<br>$X^1$ = CH$_3$<br>$X^2$ = Cl<br>Z = N |
| I-1603 | $R^2$ = CH$_2$Ph<br>$R^3$ = $R^4$ = $R^5$ = H | $R^6$ = H<br>$X^1$ = CH$_3$<br>$X^2$ = OCH$_3$<br>Z = N |
| I-1604 | $R^2$ = CH$_2$(Ph-4-Cl)<br>$R^3$ = $R^4$ = $R^5$ = H | $R^6$ = H<br>$X^1$ = Cl<br>$X^2$ = Cl<br>Z = N |
| I-1605 | $R^2$ = CH$_2$(Ph-4-CH$_3$)<br>$R^3$ = $R^4$ = $R^5$ = H | $R^6$ = H<br>$X^1$ = Cl<br>$X^2$ = OCH$_3$<br>Z = N |
| I-1606 | $R^2$ = COCH=CHCH$_3$<br>$R^3$ = $R^4$ = $R^5$ = H | $R^6$ = H<br>$X^1$ = N(CH$_3$)$_2$<br>$X^2$ = OCH$_3$<br>Z = N |
| I-1607 | $R^2$ = COOCH$_2$CF$_3$<br>$R^3$ = $R^4$ = $R^5$ = H | $R^6$ = H<br>$X^1$ = OCH$_2$CH$_2$F<br>$X^2$ = OCH$_3$<br>Z = N |
| I-1608 | $R^2$ = COOCH$_2$CH$_2$F<br>$R^3$ = $R^4$ = $R^5$ = H | $R^6$ = H<br>$X^1$ = OCH$_3$<br>$X^2$ = OCH$_3$<br>Z = N |
| I-1609 | $R^2$ = COOCH$_2$CH$_2$OCH$_3$<br>$R^3$ = $R^4$ = $R^5$ = H | $R^6$ = H<br>$X^1$ = CH$_3$<br>$X^2$ = CH$_3$<br>Z = CH |
| I-1610 | $R^2$ = COOCH$_2$CH=CHCH$_3$<br>$R^3$ = $R^4$ = $R^5$ = H | $R^6$ = H<br>$X^1$ = CH$_3$<br>$X^2$ = Cl<br>Z = CH |
| I-1611 | $R^2$ = COOCH$_2$CH=CCl$_2$<br>$R^3$ = $R^4$ = $R^5$ = H | $R^6$ = CH$_3$<br>$X^1$ = CH$_3$<br>$X^2$ = OCH$_3$<br>Z = CH |
| I-1612 | $R^2$ = COOC$_2$CCH<br>$R^3$ = $R^4$ = $R^5$ = H | $R^6$ = H<br>$X^1$ = Cl<br>$X^2$ = Cl<br>Z = CH |
| I-1613 | $R^2$ = CO(Ph-4-Cl)<br>$R^3$ = $R^4$ = $R^5$ = H | $R^6$ = H<br>$X^1$ = Cl<br>$X^2$ = OCH$_3$<br>Z = CH |
| I-1614 | $R^2$ = CO(Ph-4-CH$_3$)<br>$R^3$ = $R^4$ = $R^5$ = H | $R^6$ = CH$_3$<br>$X^1$ = OCH$_3$<br>$X^2$ = OCH$_3$<br>Z = CH |
| I-1615 | $R^2$ = COCH$_2$Ph<br>$R^3$ = $R^4$ = $R^5$ = H | $R^6$ = H<br>$X^1$ = CH$_3$<br>$X^2$ = CH$_3$<br>Z = N |
| I-1616 | $R^2$ = COCH$_2$(Ph-4-Cl)<br>$R^3$ = $R^4$ = $R^5$ = H | $R^6$ = H<br>$X^1$ = CH$_3$<br>$X^2$ = Cl<br>Z = N |
| I-1617 | $R^2$ = COCH$_2$(Ph-4-CH$_3$)<br>$R^3$ = $R^4$ = $R^5$ = H | $R^6$ = H<br>$X^1$ = CH$_3$<br>$X^2$ = OCH$_3$<br>Z = N |
| I-1618 | $R^2$ = H<br>$R^3$ = Br<br>$R^4$ = H<br>$R^5$ = H | $R^6$ = H<br>$X^1$ = Cl<br>$X^2$ = Cl<br>Z = N |
| I-1619 | $R^2$ = H<br>$R^3$ = CH$_3$<br>$R^4$ = H<br>$R^5$ = H | $R^6$ = H<br>$X^1$ = Cl<br>$X^2$ = OCH$_3$<br>Z = N |
| I-1620 | $R^2$ = H<br>$R^3$ = CH$_2$CF$_3$<br>$R^4$ = H<br>$R^5$ = H | $R^6$ = H<br>$X^1$ = N(CH$_3$)$_2$<br>$X^2$ = OCH$_3$<br>Z = N |
| I-1621 | $R^2$ = H<br>$R^3$ = Ph<br>$R^4$ = H<br>$R^5$ = H | $R^6$ = H<br>$X^1$ = OCH$_2$CH$_2$F<br>$X^2$ = OCH$_3$<br>Z = N |
| I-1622 | $R^2$ = H<br>$R^3$ = CH$_2$Ph<br>$R^4$ = H<br>$R^5$ = H | $R^6$ = H<br>$X^1$ = OCH$_3$<br>$X^2$ = OCH$_3$<br>Z = N |
| I-1623 | $R^2$ = H<br>$R^3$ = COCH$_3$<br>$R^4$ = H<br>$R^5$ = H | $R^6$ = H<br>$X^1$ = CH$_3$<br>$X^2$ = CH$_3$<br>Z = CH |
| I-1624 | $R^2$ = $R^4$ = $R^5$ = H<br>$R^3$ = CO-cyc-Pr | $R^6$ = H<br>$X^1$ = CH$_3$<br>$X^2$ = Cl<br>Z = CH |
| I-1625 | $R^2$ = H<br>$R^3$ = COCF$_3$<br>$R^4$ = H<br>$R^5$ = H | $R^6$ = CH$_3$<br>$X^1$ = CH$_3$<br>$X^2$ = OCH$_3$<br>Z = CH |
| I-1626 | $R^2$ = $R^4$ = $R^5$ = H<br>$R^3$ = CON(CH$_3$)$_2$ | $R^6$ = H<br>$X^1$ = Cl<br>$X^2$ = Cl<br>Z = CH |
| I-1627 | $R^2$ = H<br>$R^3$ = COOCH$_3$<br>$R^4$ = H<br>$R^5$ = H | $R^6$ = H<br>$X^1$ = Cl<br>$X^2$ = OCH$_3$<br>Z = CH |
| I-1628 | $R^2$ = $R^4$ = $R^5$ = H | $R^6$ = CH$_3$ |

TABLE 4-continued

| No. | R² R³ R⁴ R⁵ | R⁶ X¹ X² Z |
|---|---|---|
| | R³ = COOCH₂CH₂F | X¹ = OCH₃<br>X² = OCH₃<br>Z = CH |
| I-1629 | R² = H<br>R³ = COPh<br>R⁴ = H<br>R⁵ = H | R⁶ = H<br>X¹ = CH₃<br>X² = CH₃<br>Z = N |
| I-1630 | R² = H<br>R³ = COCH₂Ph<br>R⁴ = H<br>R⁵ = H | R⁶ = H<br>X¹ = CH₃<br>X² = Cl<br>Z = N |
| I-1631 | R² = H<br>R³ = CH₂CF₃<br>R⁴ = H<br>R⁵ = H | R⁶ = H<br>X¹ = CH₃<br>X² = OCH₃<br>Z = N |
| I-1632 | R² = H<br>R³ = Ph<br>R⁴ = H<br>R⁵ = H | R⁶ = H<br>X¹ = Cl<br>X² = Cl<br>Z = N |
| I-1633 | R² = H<br>R³ = CH₂Ph<br>R⁴ = H<br>R⁵ = H | R⁶ = H<br>X¹ = Cl<br>X² = OCH₃<br>Z = N |
| I-1634 | R² = H<br>R³ = COCH₃<br>R⁴ = H<br>R⁵ = H | R⁶ = H<br>X¹ = N(CH₃)₂<br>X² = OCH₃<br>Z = N |
| I-1635 | R² = R⁴ = R⁵ = H<br>R³ = CO-cyc-Pr | R⁶ = H<br>X¹ = OCH₂CH₂F<br>X² = OCH₃<br>Z = N |
| I-1636 | R² = H<br>R³ = COCF₃<br>R⁴ = H<br>R⁵ = H | R⁶ = H<br>X¹ = OCH₃<br>X² = OCH₃<br>Z = N |
| I-1637 | R² = R⁴ = R⁵ = H<br>R³ = CON(CH₃)₂ | R⁶ = H<br>X¹ = CH₃<br>X² = CH₃<br>Z = CH |
| I-1638 | R² = H<br>R³ = COOCH₃<br>R⁴ = H<br>R⁵ = H | R⁶ = H<br>X¹ = CH₃<br>X² = Cl<br>Z = CH |
| I-1639 | R² = R⁴ = R⁵ = H<br>R³ = COOCH₂CH₂F | R⁶ = CH₃<br>X¹ = CH₃<br>X² = OCH₃<br>Z = CH |
| I-1640 | R² = CH₃<br>R³ = Br<br>R⁴ = H<br>R⁵ = CH₃ | R⁶ = H<br>X¹ = Cl<br>X² = Cl<br>Z = CH |
| I-1641 | R² = CH₃<br>R³ = COCH₃<br>R⁴ = H<br>R⁵ = CH₃ | R⁶ = H<br>X¹ = Cl<br>X² = OCH₃<br>Z = CH |
| I-1642 | R² = CH₃<br>R³ = COC₂H₅<br>R⁴ = H<br>R⁵ = CH₃ | R⁶ = CH₃<br>X¹ = OCH₃<br>X² = OCH₃<br>Z = CH |
| I-1643 | R² = CH₃<br>R³ = COOCH₃<br>R⁴ = H<br>R⁵ = CH₃ | R⁶ = H<br>X¹ = CH₃<br>X² = CH₃<br>Z = N |
| I-1644 | R² = COCH₃<br>R³ = H<br>R⁴ = H<br>R⁵ = Br | R⁶ = H<br>X¹ = CH₃<br>X² = Cl<br>Z = N |
| I-1645 | R² = COC₂H₅<br>R³ = H<br>R⁴ = H<br>R⁵ = Br | R⁶ = H<br>X¹ = CH₃<br>X² = OCH₃<br>Z = N |
| I-1646 | R² = COPh<br>R³ = H<br>R⁴ = H | R⁶ = H<br>X¹ = Cl<br>X² = Cl |
| | R⁵ = Br | Z = N |
| I-1647 | R² = COCH₃<br>R³ = H<br>R⁴ = H<br>R⁵ = CH₃ | R⁶ = H<br>X¹ = Cl<br>X² = OCH₃<br>Z = N |
| I-1648 | R² = COC₂H₅<br>R³ = H<br>R⁴ = H<br>R⁵ = CH₃ | R⁶ = H<br>X¹ = N(CH₃)₂<br>X² = OCH₃<br>Z = N |
| I-1649 | R² = COPh<br>R³ = H<br>R⁴ = H<br>R⁵ = CH₃ | R⁶ = H<br>X¹ = OCH₂CH₂F<br>X² = OCH₃<br>Z = N |
| I-1650 | R² = COCH₂OCH₃<br>R³ = H<br>R⁴ = H<br>R⁵ = H | R⁶ = H<br>X¹ = CH₃<br>X² = OCH₃<br>Z = CH |
| I-1651 | R² = COCH₂OCH₃<br>R³ = H<br>R⁴ = H<br>R⁵ = H | R⁶ = H<br>X¹ = OCH₃<br>X² = OCH₃<br>Z = CH |
| I-1652 | R² = COCH₂OC₂H₅<br>R³ = H<br>R⁴ = H<br>R⁵ = H | R⁶ = H<br>X¹ = OCH₃<br>X² = OCH₃<br>Z = CH |
| I-1653 | R² = CONH₂<br>R³ = H<br>R⁴ = H<br>R⁵ = H | R⁶ = H<br>X¹ = OCH₃<br>X² = OCH₃<br>Z = CH |
| I-1654 | R² = CONHCH₃<br>R³ = H<br>R⁴ = H<br>R⁵ = H | R⁶ = H<br>X¹ = CH₃<br>X² = OCH₃<br>Z = CH |
| I-1655 | R² = CONHCH₃<br>R³ = H<br>R⁴ = H<br>R⁵ = H | R⁶ = H<br>X¹ = OCH₃<br>X² = OCH₃<br>Z = CH |
| I-1656 | R² = CONHC₂H₅<br>R³ = H<br>R⁴ = H<br>R⁵ = H | R⁶ = H<br>X¹ = OCH₃<br>X² = OCH₃<br>Z = CH |
| I-1657 | R² = COOH<br>R³ = H<br>R⁴ = H<br>R⁵ = H | R⁶ = H<br>X¹ = OCH₃<br>X² = OCH₃<br>Z = CH |

The N-(substituted amino)pyrrole derivative of the above formula (I) can be synthesized by reacting an aminoazine derivative of the formula (IV) with a halogenosulfonyl isocyanate of the formula (V) to form an (azinylureylene) sulfonylisocyanate of the formula (III), followed by reacting it with an N-aminopyrrole derivative of the formula (II) without preferably isolating the intermediate, according to the following reaction formula.

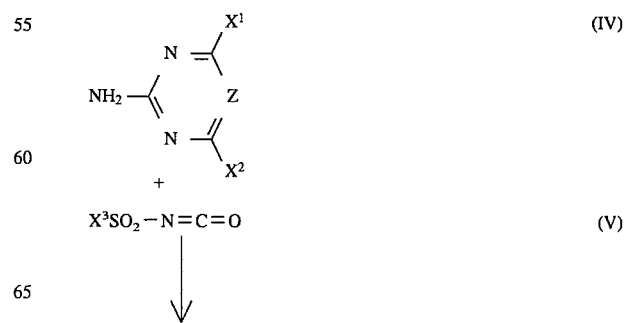

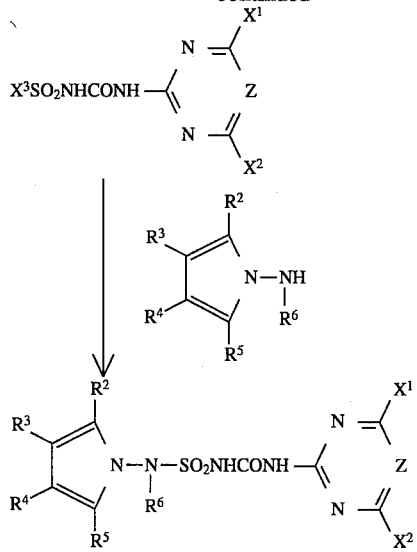

Reaction steps of the above reaction formula are carried out at a temperature in a range of from −78° C. to a boiling point of the solvent, and preferably from 0° C. to 40° C., in an inert organic solvent, for example, hydrocarbons such as benzene, toluene, xylene, cyclohexane, etc., chlorinated hydrocarbons such as methylene chloride, chloroform, carbon tetrachloride and chlorobenzene, ethers such as diethylether, dimethoxyethane, diethyleneglycol, dimethylether, tetrahydrofuran and dioxane, and aprotic polar solvent such as acetonitrile or nitromethane.

In these reactions, it is preferred to use an organic tertiary amine, preferably pyridine or triethylamine, or an inorganic base such as carbonates of alkali metal as an acid acceptor.

If necessary, the compound of the formula (II) may be used in an excess amount so as to simultaneously react as an auxilliary base.

In the compound of the formula (I), preferable groups of $X^1$ and $X^2$ are exemplified as follows. Hydrogen atom, chlorine atom and fluorine atom; methyl group, ethyl group and i-propyl group; ethoxy group, i-propoxy group, methoxy group and sec-butoxy group; thiomethoxy group and thio-i-propoxy group; trifluoromethyl group, fluoromethyl group, difluoromethyl group and 2,2,2-trifluoroethyl group; 1,1,2,2-tetrafluoroethoxy group, 2,2,2-trifluoroethoxy group, 2-fluoroethoxy group, difluoromethoxy group, 2-bromo-1,1,2-trifluoroethoxy group, 1,1,2,3,3,3-hexafluoropropoxy group and 2-chloro-1,1,2-trifluoroethoxy group; difluorothiomethoxy group; dimethoxymethyl group and methoxymethyl group; thiomethoxymethyl group; dimethylamino group, ethyl(methyl)amino group, methoxy(methyl) amino group, amino group and methylamino group.

The N-(substituted amino)pyrrole derivative of the above formula (I-b) can also be produced by reacting an N-(substituted amino)pyrrole derivative of the above formula (I-a) with a compound of the formula (VI) in the presence of a base to substitute hydrogen atom of N-amino group on the pyrrole ring of the compound of the formula (I-a) with the group $R^1$ as shown in the above reaction formula.

The reaction for replacing hydrogen atom of N-amino group on the pyrrole ring of the compound represented by the formula (I-a) with the group $R^1$ is carried out at a temperature in a range of from 0° C. to a boiling point of the solvent in the presence of an inorganic base such as sodium hydride or potassium carbonate in a solvent such as dioxane or dimethylformamide. As a substitution reagent, a compound of the formula (VI) which form the group $R^1$ as an electrophilic cation can be used.

Examples of such compound of the formula (VI) include methyl iodide, ethyl iodide, i-propyl iodide, n-butyl bromide, dimethyl sulfate, 2,2,2-trifluoroethyl iodide, 3-methoxypropyl bromide, crotyl bromide, propargyl chloride, 1,1,3-trichloropropene, benzyl bromide, 4-chlorobenzyl bromide and 4-methylbenzyl bromide etc.

After completion of the reaction, the reaction mixture is added to an aqueous solution of dilute hydrochloric acid and the precipitate thus formed is collected by filtration. The precipitate is dried in air and then purified by column chromatography or by a washing technique, whereby the N-(substituted amino)pyrrole derivative of the formula (I-b) in which the hydrogen atom of N-amino group on the pyrrole ring is replaced with the group R can be obtained.

Compounds of the formula (I-d) which has the following substituents can also be obtained by an electrophilic substitution of the hydrogen of $R^2$–$R^5$ on the pyrrole ring in the compound represented by the formula (I-c).

Halogen atoms such as bromine atom and chlorine atom, and the like; $C_1$–$C_4$ alkyl groups such as methyl and ethyl, and the like; $C_1$–$C_5$ haloalkyl groups such as 2,2,2-trifluoroethyl, and the like; $C_2$–$C_5$ alkoxyalkyl group such as 3-methoxypropyl, and the like; $C_3$–$C_5$ alkenyl groups such as crotyl, and the like; $C_3$–$C_5$ haloalkenyl groups such as 3,3-dichloroallyl, and the like; $C_3$–$C_5$ aklinyl groups such as propargyl, and the like; phenyl grops which may be substituted with 1–3 halogen atoms and/or $C_1$–$C_4$ alkyl groups, such as phenyl, 4-methylphenyl, 4-chlorophenyl, and the like; $C_7$–$C_9$ aralkyl groups which may be substituted with 1–3 halogen atoms and/or $C_1$–$C_4$ alkyl groups, such as benzyl, 4-methylbenzyl, 4-chlorobenzyl, and the like; ($C_1$–$C_4$ alkyl)carbonyl groups such as acetyl, propionyl and the like; ($C_2$–$C_5$ alkoxyalkyl)carbonyl group such as methoxyacetyl, ethoxyacetyl, and the like; ($C_3$–$C_6$ cycloalkyl) carbonyl groups such as cyclopropanecarbonyl, and the like; ($C_1$–$C_4$ haloalkyl)carbonyl groups such as trifluoroacetyl, 4-chlorobutyryl, and the like; ($C_3$–$C_5$ alkenyl)carbonyl such as crotonyl and the like; benzoyl groups which may be substituted with 1–3 halogen atoms and/or $C_1$–$C_4$ alkyl groups such as benzoyl, 4chlorobenzoyl, 4-methylbenzoyl, and the like; ($C_7$–$C_9$ aralkyl)carbonyl groups which may be substituted with 1–3 halogen atoms and/or $C_1$–$C_4$ alkyl groups such as phenylacetyl, 4-chlorophenylacetyl, 4-methylphenylacetyl, and the like; carbamoyl groups; N-($C_1$–$C_4$ alkyl)aminocarbonyl groups such as N-methylaminocarbonyl, N-ethylaminocarbonyl, and the like; N,N-[(di-($C_1$–$C_4$ alkyl)aminocarbonyl groups such as dimethylcarbamoyl, diethylcarbamoyl, and the like; carboxyl group; ($C_1$–$C_4$ alkoxy)carbonyl groups such as methoxycarbonyl and the like; ($C_1$–$C_4$ haloalkoxy)carbonyl groups such as (2,2,2-trifluoroethoxy)carbonyl, and the like; ($C_2$–$C_5$ alkoxyalkoxy)carbonyl groups such as (2-methoxyethoxy)carbonyl, and the like; ($C_3$–$C_5$ alkenyloxy)carbonyl groups such as crotyloxycarbonyl, and the like; ($C_3$–$C_5$ haloalkenyloxy) carbonyl groups such as (3,3-dichloroallyloxy)carbonyl and the like; and ($C_3$–$C_5$ alkynyloxy)carbonyl groups such as propargyloxycarbonyl, and the like. (Refer to J. Org. Chem., 48. 3214–3219 (1983). ibid 40, 3161–3169 (1975). ibid 46, 2221–2225 (1981). Org. Synth., 44, 69 (1964). J. Chem. Soc., Perkin Trans. 1., 1983, 93–102.)

The compound of the formula (I) is possible to replace a hydrogen atom on the nitrogen atom of ureylene group with a suitable cation to form a salt. Examples of the salt generally include metal salts, particularly alkali metal salts and alkaline earth metal salts, and if necessary, ammonium salts and organic amine salts.

The salts can be produced preferably at a temperature in a range of from 20° to 100° C. in a solvent such as water, alcohol or acetone.

The compound of the formula (IV) can be synthesized by cyclization of a suitable guanidine derivative with a substituted 1,3-diketone. (The Chemistry of Heterocyclic Compounds. Vol.XVI (1962) and Supplement I (1970))

The above compound can also be synthesized from an N-cyanoamidine derivative or an N-cyanoimidate derivative. (Refer to J. Org. Chem., 28. 1812–1821 (1963))

Further, the above compound can be synthesized from cyanuric chloride. (L. Rapoport: The Chemistry of Heterocyclic Compounds. (1959))

In the compound of the formula (IV), it is possible to change halogen atom of $X^1$ or $X^2$ into $C_1$–$C_4$ alkoxy group, $C_1$–$C_4$ alkylthio group, $C_1$–$C_4$ haloalkoxy group, $C_1$–$C_4$ haloalkylthio group or $NR^7R^8$ by reacting with an alcohol, thioalcohol or amine in a diluent under a basic condition. (Refer to J. Chem. Soc., 1946, 81–85. British Patent 571014 (1945): Chem. Abstr., 40, 7238 (1946).

The compounds (IV) in which $X^1$ or $X^2$ is $C_1$–$C_4$ alkoxy, $C_1$–$C_4$ alkylthio, $C_1$–$C_4$ haloalkoxy, $C_1$–$C_4$ haloalkylthio and so on can also be obtained by alkylation of hydroxyl group or mercapto group bonded to the 4-position or 6-position of the pyrimidine ring or 1,3,5-triazine ring in a diluent under a basic condition. (Refer to EP-A-70804)

The compound of the formula (II) can be synthesized as follows.

That is, an N-(1H-pyrrol-1-yl)phthalimide derivative can be obtained by reacting an amino group of an N-aminophthalimide with a γ-dioxo compound of the formula (VII-e1) or a cyclized product of a γ-dioxo compound of the formula (VII-e2) in dioxane or acetic acid containing an acid catalyst with heating under stirring. (Refer to Chem. Ber., 102, 3268–76 (1969))

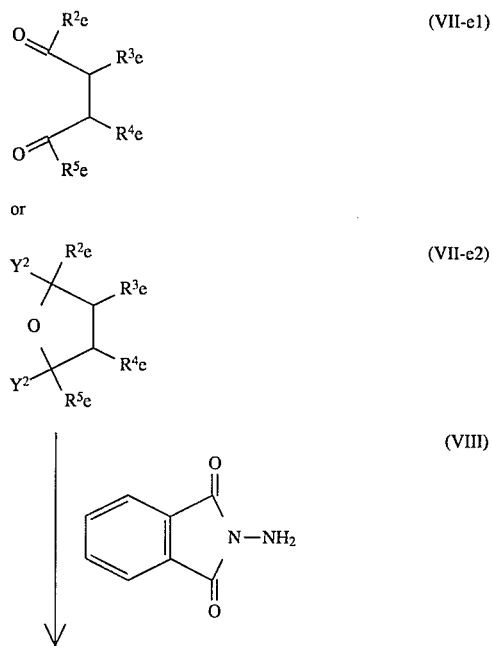

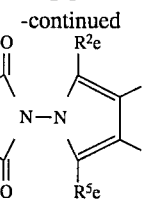

wherein $R^2e$, $R^3e$, $R^4e$ and $R^5e$ are independently hydrogen atom, halogen atom, $C_1$–$C_4$ alkyl group, $C_1$–$C_5$ haloalkyl group, $C_2$–$C_5$ alkoxyalkyl group, $C_3$–$C_5$ alkenyl group, $C_3$–$C_5$ haloalkenyl group, $C_3$–$C_5$ alkynyl group, phenyl group which may be substituted with 1–3 halogen atoms and/or $C_1$–$C_4$ alkyl groups, $C_7$–$C_9$ aralkyl group which may be substituted with 1–3 halogen atoms and/or $C_1$–$C_4$ alkyl groups, ($C_1$–$C_4$ alkyl)carbonyl group, ($C_2$–$C_5$ alkoxyalkyl)carbonyl group, ($C_3$–$C_6$ cycloalkyl)carbonyl group, ($C_1$–$C_4$ haloalkyl)carbonyl group, ($C_3$–$C_5$ alkenyl)carbonyl group, benzoyl group which may be substituted with 1–3 halogen atoms and/or $C_1$–$C_4$ alkyl groups, ($C_7$–$C_9$ aralkyl)carbonyl group which may be substituted with 1–3 halogen atoms and/or $C_1$–$C_4$ alkyl groups, carbamoyl group, N-($C_1$–$C_4$ alkyl)aminocarbonyl groups, N,N-[(di-$C_1$–$C_4$ alkyl)amino]carbonyl group, carboxyl group, ($C_1$–$C_4$ alkoxy)carbonyl group, ($C_1$–$C_4$ haloalkoxy)carbonyl group, ($C_2$–$C_5$ alkoxyalkoxy)carbonyl group, ($C_3$–$C_5$ alkenyloxy)carbonyl group, ($C_3$–$C_5$ haloalkenyloxy)carbonyl group or ($C_3$–$C_5$ alkynyloxy)carbonyl group, and $Y^2$ is $C_1$–$C_4$ alkoxy group.

This cyclic condensation reaction is particularly suitable for synthesizing compounds of (IX-e) in which $R^2e$–$R^5e$ on the pyrrole ring are each hydrogen atom, halogen atom, $C_1$–$C_4$ alkyl group, $C_1$–$C_5$ haloalkyl group, $C_2$–$C_5$ alkoxyalkyl group, $C_3$–$C_5$ alkenyl group, $C_3$–$C_5$ haloalkenyl group, $C_3$–$C_5$ alkynyl group, phenyl group which may be substituted with 1–3 halogen atoms and/or $C_1$–$C_4$ alkyl groups, $C_7$–$C_9$ aralkyl group which may be substituted with 1–3 halogen atoms and/or $C_1$–$C_4$ alkyl groups.

Compound represented by the formula [IX, $R^2q$–$R^5q$ are replaced by $R^2$–$R^5$ in compound (IX-q) wherein $R^2$–$R^5$ are not hydrogen atom can be synthesized as follows. Namely, compounds of the formula (IX-g) can be synthesized by electrophilic substitution of hydrogen atom on the pyrrole ring of a compound represented by the formula (IX-f) according to the following reaction formula similarly to the reaction of deriving a compound of the formula (I-d) from a compound of the formula (I-c).

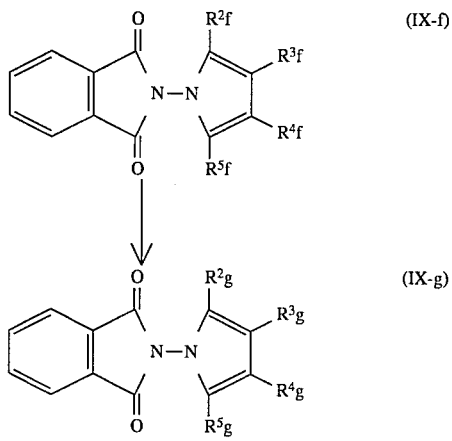

wherein at least one of $R^2$-f–$R^5$f is hydrogen atom and the others are independently hydrogen atom, halogen atom, $C_1$–$C_4$ alkyl group, $C_1$–$C_5$ haloalkyl group, $C_2$–$C_5$ group, $C_3$–$C_5$ alkenyl group, $C_3$–$C_5$ haloalkenyl group, $C_3$–$C_5$ alkynyl group, phenyl group which may be substituted with 1–3 halogen atoms and/or $C_1$–$C_4$ alkyl groups, $C_7$–$C_9$ aralkyl group which may be substituted with 1–3 halogen atoms and/or $C_1$–$C_4$ alkyl groups, ($C_1$–$C_4$ alkyl)carbonyl group, ($C_2$–$C_5$ alkoxyalkyl)carbonyl group, ($C_3$–$C_6$ cycloalkyl)carbonyl group, ($C_1$–$C_4$ haloalkyl)carbonyl group, ($C_3$–$C_5$ alkenyl)carbonyl group, benzoyl group which may be substituted with 1–3 halogen atoms and/or $C_1$–$C_4$ alkyl groups, ($C_7$–$C_9$ aralkyl)carbonyl group which may be substituted with 1–3 halogen atoms and/or $C_1$–$C_4$ alkyl groups, carbamoyl group, N-($C_1$–$C_4$ alkyl)aminocarbonyl group, N,N-[(di-$C_1$–$C_4$ alkyl)amino]carbonyl group, carboxyl group, ($C_1$–$C_4$ alkoxy)carbonyl group, ($C_1$–$C_4$ haloalkoxy)carbonyl group, ($C_2$–$C_5$ alkoxyalkoxy)carbonyl group, ($C_3$–$C_5$ alkenyloxy)carbonyl group, ($C_3$–$C_5$ haloalkenyloxy)carbonyl group or ($C_3$–$C_5$ alkynyloxy)carbonyl group;

at least one of $R^2g$–$R^5g$, which is a substituent for the hydrogen atom, is halogen atom, $C_1$–$C_4$ alkyl group, $C_1$–$C_5$ haloalkyl group, $C_2$–$C_5$ alkoxyalkyl group, $C_3$–$C_5$ alkenyl group, $C_3$–$C_5$ haloalkenyl group, $C_3$–$C_5$ alkynyl group, phenyl group which may be substituted with 1–3 halogen atoms and/or $C_1$–$C_4$ alkyl groups, $C_7$–$C_9$ aralkyl group which may be substituted with 1–3 halogen atoms and/or $C_1$–$C_4$ alkyl groups, ($C_1$–$C_4$ alkyl)carbonyl group, ($C_2$–$C_5$ alkoxyalkyl)carbonyl group, ($C_3$–$C_6$ cycloalkyl)carbonyl group, ($C_1$–$C_4$ haloalkyl)carbonyl group, ($C_3$–$C_5$ alkenyl)carbonyl group, benzoyl group which may be substituted with 1–3 halogen atoms and/or $C_1$–$C_4$ alkyl groups, ($C_7$–$C_9$ aralkyl)carbonyl group which may be substituted with 1–3 halogen atoms and/or $C_1$–$C_4$ alkyl groups, carbamoyl group, N-($C_1$–$C_4$ alkyl)aminocarbonyl group, N,N-[(di-$C_1$–$C_4$ alkyl)aminocarbonyl group, carboxyl group, ($C_1$–$C_4$ alkoxy)carbonyl group, ($C_1$–$C_4$ haloalkoxy)carbonyl group, ($C_2$–$C_5$ alkoxyalkoxy)carbonyl group, ($C_3$–$C_5$ alkenyloxy)carbonyl group, ($C_3$–$C_5$ haloalkenyloxy)carbonyl group or ($C_3$–$C_5$ alkynyloxy)carbonyl group;

and the others of $R^2g$–$R^5g$ are independently hydrogen atom, halogen atom, $C_1$–$C_4$ alkyl group, $C_1$–$C_5$ haloalkyl group, $C_2$–$C_5$ alkoxyalkyl group, $C_3$–$C_5$ alkenyl group, $C_3$–$C_5$ haloalkenyl group, $C_3$–$C_5$ alkynyl group, phenyl group which may be substituted with 1–3 halogen atoms and/or $C_1$–$C_4$ alkyl groups, $C_7$–$C_9$ aralkyl group which may be substituted with 1–3 halogen atoms and/or $C_1$–$C_4$ alkyl groups, ($C_1$–$C_4$ alkyl)carbonyl group, ($C_2$–$C_5$ alkoxyalkyl)carbonyl group, ($C_3$–$C_6$ cycloalkyl)carbonyl group, ($C_1$–$C_4$ haloalkyl)carbonyl group, ($C_3$–$C_5$ alkenyl)carbonyl group, benzoyl group which may be substituted with 1–3 halogen atoms and/or $C_1$–$C_4$ alkyl groups, ($C_7$–$C_9$ aralkyl)carbonyl group which may be substituted with 1–3 halogen atoms and/or $C_1$–$C_4$ alkyl groups, carbamoyl group, N-($C_1$–$C_4$ alkyl)aminocarbonyl groups, N,N-[(di-$C_1$–$C_4$ alkyl)amino]carbonyl group, carboxyl group, ($C_1$–$C_4$ alkoxy)carbonyl group, ($C_1$–$C_4$ haloalkoxy)carbonyl group, ($C_2$–$C_5$ alkoxyalkoxy)carbonyl group, ($C_3$–$C_5$ alkenyloxy)carbonyl group, ($C_3$–$C_5$ haloalkenyloxy)carbonyl group or ($C_3$–$C_5$ alkynyloxy)carbonyl group.

Regarding the electrophilic reactions of the pyrrole ring, alkylation and acylation can be conducted by a Friedel-Crafts reaction.

Alkylation and acylation is carried out using as a reagent an alkylating agent such as halogenated hydrocarbon or sulfuric acid ester or an acylating agent such as organic acid halide or acid anhydride, by reacting with a Lewis acid to form a cation by which the pyrrole ring is electrophilically attacked to cause replacement of the hydrogen atom. (J. Org. Chem., 48, 3214–3219 (1983))

It is preferred to carry out the reaction in alkyl halide such as 1,2-dichloroethane at 0°–50° C. for 30 minutes to few hours, by which the target compound is obtained. obtained.

The carbamoyl group, N-($C_1$–$C_4$ alkyl)aminocarbonyl groups, N,N-[(di-$C_1$–$C_4$ alkyl)amino]carbonyl group, carboxyl group, ($C_1$–$C_4$ alkoxy)carbonyl group, ($C_1$–$C_4$ haloalkoxy)carbonyl group, ($C_2$–$C_5$ alkoxyalkoxy)carbonyl group, ($C_3$–$C_5$ alkenyloxy)carbonyl group, ($C_3$–$C_5$ haloalkenyloxy)carbonyl group or ($C_3$–$C_5$ alkynyloxy)carbonyl group on the pyrrole ring of the compound represented by the formula (IX-g) can be derived from ammonia, $C_1$–$C_4$ alkylamine, (di-$C_1$–$C_4$ alkyl)amine, water, $C_1$–$C_4$ alkanol, $C_1$–$C_4$ aloalkanol, $C_2$–$C_5$ alkoxyalkanol, $C_3$–$C_5$ alkenol, $C_3$–$C_5$ haloalkenol or $C_3$–$C_5$ alkynol by reacting with a chlorocarbonyl group.

Introduction of the chlorocarbonyl group can be carried out by a Friedel-Crafts reaction using oxalyl chloride as a reagent. (Refer to Org. Synth. 44, 69 (1964). J. Org. Chem., 48, 3214–3219 (1983)).

Halogenation reaction may be carried out using a halogenating agent such as chlorine, bromine, iodine, N-chlorosuccinimide, N-bromosuccinimide, sulfuryl chloride or the like in a diluent at −10°–40° C. for few hours. (J. Org. Chem., 40, 3161–3169 (1975). ibid 46, 2221–2225 (1981)).

Compounds of the formulas (I-c) and (IX-f) can also be used as starting materials for conducting halogenation, alkylation and acylation by electrophilic replacement of hydrogen atoms on the pyrrole ring.

It is therefore possible to choose a starting material in consideration of yield, easiness of post-treatment etc.

Metal salt of alkaline earth metal can be used as a catalyst in the above-mentioned electrophilic replacement reaction of hydrogen atoms on the pyrrole ring.

N-aminopyrrole derivatives of the formula (II) are obtained from compounds of the formula (IX). For example, a compound of the formula [II-a, $R^6$ is hydrogen atom in compound (II)] can be obtained by reacting the compound of the formula (IX) with hydrazine hydrate in lower alchohol. (Refer to Chem. Ber., 102, 3268–76 (1969))

A compound of the formula (II) in which $R^6$ is not hydrogen atom can be synthesized by alkylation of one of hydrogen atoms of amino group in compound represented by the formula (II-a). The alkylation reaction is conducted using the same alkylating agent (Compound of the formula (VI)), diluent and reaction condition as those for alkylation of the above described compound (I-a).

Specific examples of compounds represented by the formula (II) used as the above described intermediates are shown in Table 5.

TABLE 5

| No. | $R^2$<br>$R^3$ | $R^4$<br>$R^5$ | $R^6$ |
|---|---|---|---|
| II-1 | H<br>H | H<br>H | H |
| II-2 | Cl<br>H | H<br>H | H |
| II-3 | Br<br>H | H<br>H | H |
| II-4 | $CH_3$<br>H | H<br>H | H |
| II-5 | $CH_3$<br>H | H<br>$CH_3$ | H |
| II-6 | $CH_2CF_3$ | H | H |

TABLE 5-continued

| No. | $R^2$ / $R^3$ | $R^4$ / $R^5$ | $R^6$ |
|---|---|---|---|
| II-7 | H / CH$_2$CH=CHCH$_3$ | H / H | H |
| II-8 | H / CH$_2$CH=CCl$_2$ | H / H | H |
| II-9 | H / CH$_2$CCH | H / H | H |
| II-10 | H / Ph | H / H | H |
| II-11 | H / Ph-4-CH$_3$ | H / H | H |
| II-12 | H / Ph-4-Cl | H / H | H |
| II-13 | H / CH$_2$Ph | H / H | H |
| II-14 | H / CH$_2$(Ph-4-CH$_3$) | H / H | H |
| II-15 | H / CH$_2$(Ph-4-Cl) | H / H | H |
| II-16 | H / COCH$_3$ | H / H | H |
| II-17 | H / COC$_2$H$_5$ | H / H | H |
| II-18 | H / CO-cyc-Pr | H / H | H |
| II-19 | H / COCF$_3$ | H / H | H |
| II-20 | H / CO(CH$_2$)$_3$Cl | H / H | H |
| II-21 | H / COCH=CHCH$_3$ | H / H | H |
| II-22 | H / COPh | H / H | H |
| II-23 | H / CO(Ph-4-Cl) | H / H | H |
| II-24 | H / CO(Ph-4-CH$_3$) | H / H | H |
| II-25 | H / COCH$_2$Ph | H / H | H |
| II-26 | H / COCH$_2$(Ph-4-Cl) | H / H | H |
| II-27 | H / COCH$_2$(Ph-4-CH$_3$) | H / H | H |
| II-28 | H / CON(CH$_3$)$_2$ | H / H | H |
| II-29 | H / COOCH$_3$ | H / H | H |
| II-30 | H / COOCH$_2$CF$_3$ | H / H | H |
| II-31 | H / COOCH$_2$CH$_2$F | H / H | H |
| II-32 | H / COOCH$_2$CH$_2$OCH$_3$ | H / H | H |
| II-33 | H / COOCH$_2$CH=CHCH$_3$ | H / H | H |
| II-34 | H / COOCH$_2$CH=CCl$_2$ | H / H | H |
| II-35 | H / COOC$_2$CCH | H / H | H |
| II-36 | H / Br | H / H | H |
| II-37 | H / CH$_3$ | H / H | H |
| II-38 | H / CH$_2$CF$_3$ | H / H | H |
| II-39 | H / CH$_2$Ph | H / H | H |
| II-40 | H / COCH$_3$ | H / H | H |
| II-41 | H / CO-cyc-Pr | H / H | H |
| II-42 | H / COCF$_3$ | H / H | H |
| II-43 | H / COPh | H / H | H |
| II-44 | H / H | H / H | H |
| II-45 | H / COCH$_2$Ph | H / H | H |
| II-46 | H / CON(CH$_3$)$_2$ | H / H | H |
| II-47 | H / COOCH$_3$ | H / H | H |
| II-48 | CH$_3$ / Br | H / CH$_3$ | H |
| II-49 | CH$_3$ / COCH$_3$ | H / CH$_3$ | H |
| II-50 | CH$_3$ / COC$_2$H$_5$ | H / CH$_3$ | H |
| II-51 | CH$_3$ / COCH$_2$Ph | H / CH$_3$ | H |
| II-52 | CH$_3$ / COOCH$_3$ | H / CH$_3$ | H |
| II-53 | COCH$_3$ / H | H / Br | H |
| II-54 | COC$_2$H$_5$ / H | H / Br | H |
| II-55 | COPh / H | H / Br | H |
| II-56 | COOCH$_3$ / H | H / Br | H |
| II-57 | COCH$_3$ / H | H / CH$_3$ | H |
| II-58 | COC$_2$H$_5$ / H | H / CH$_3$ | H |
| II-59 | COPh / H | H / CH$_3$ | H |
| II-60 | COOCH$_3$ / H | H / CH$_3$ | H |
| II-61 | COCH$_2$OCH$_3$ / H | H / H | H |
| II-62 | COCH$_2$OC$_2$H$_5$ / H | H / H | H |
| II-63 | CONH$_2$ / H | H / H | H |
| II-64 | CONHCH$_3$ / H | H / H | H |
| II-65 | CONHC$_2$H$_5$ / H | H / H | H |
| II-66 | COOH / H | H / H | H |

Examples of compounds represented by formula (IX) which are used as intermidiates for production of compounds of the formula (II) include those described in Table 6.

TABLE 6

| No. | $R^2$ / $R^3$ | $R^4$ / $R^5$ |
|---|---|---|
| IX-1 | H / H | H / H |
| IX-2 | Cl / H | H / H |
| IX-3 | Br / H | H / H |
| IX-4 | CH$_3$ / H | H / H |
| IX-5 | CH$_3$ / H | H / CH$_3$ |
| IX-6 | CH$_2$CF$_3$ / H | H / H |
| IX-7 | CH$_2$CH=CHCH$_3$ / H | H / H |
| IX-8 | CH$_2$CH=CCl$_2$ / H | H / H |
| IX-9 | CH$_2$CCH / H | H / H |

TABLE 6-continued

| No. | R² / R³ | R⁴ / R⁵ |
|---|---|---|
| IX-10 | Ph / H | H / H |
| IX-11 | Ph-4-CH₃ / H | H / H |
| IX-12 | Ph-4-Cl / H | H / H |
| IX-13 | CH₂Ph / H | H / H |
| IX-14 | CH₂(Ph-4-CH₃) / H | H / H |
| IX-15 | CH₂(Ph-4-Cl) / H | H / H |
| IX-16 | COCH₃ / H | H / H |
| IX-17 | COC₂H₅ / H | H / H |
| IX-18 | CO-cyc-Pr / H | H / H |
| IX-19 | COCF₃ / H | H / H |
| IX-20 | CO(CH₂)₃Cl / H | H / H |
| IX-21 | COCH=CHCH₃ / H | H / H |
| IX-22 | COPh / H | H / H |
| IX-23 | CO(Ph-4-Cl) / H | H / H |
| IX-24 | CO(Ph-4-CH₃) / H | H / H |
| IX-25 | COCH₂Ph / H | H / H |
| IX-26 | COCH₂(Ph-4-Cl) / H | H / H |
| IX-27 | COCH₂(Ph-4-CH₃) / H | H / H |
| IX-28 | CON(CH₃)₂ / H | H / H |
| IX-29 | COOCH₃ / H | H / H |
| IX-30 | COOCH₂CF₃ / H | H / H |
| IX-31 | COOCH₂CH₂F / H | H / H |
| IX-32 | COOCH₂CH₂OCH₃ / H | H / H |
| IX-33 | COOCH₂CH=CHCH₃ / H | H / H |
| IX-34 | COOCH₂CH=CCl₂ / H | H / H |
| IX-35 | COOC₂CCH / H | H / H |
| IX-36 | H / Br | H / H |
| IX-37 | H / CH₃ | H / H |
| IX-38 | H / CH₂CF₃ | H / H |
| IX-39 | H / CH₂Ph | H / H |
| IX-40 | H / COCH₃ | H / H |
| IX-41 | H / CO-cyc-Pr | H / H |
| IX-42 | H / COCF₃ | H / H |
| IX-43 | H / COPh | H / H |
| IX-44 | H / COCH₂Ph | H / H |
| IX-45 | H / CON(CH₃)₂ | H / H |
| IX-46 | H / COOCH₃ | H / H |
| IX-47 | H / COOCH₂CH₂F | H / H |
| IX-48 | CH₃ / Br | H / CH₃ |
| IX-49 | CH₃ / COCH₃ | H / CH₃ |
| IX-50 | CH₃ / COC₂H₅ | H / CH₃ |
| IX-51 | CH₃ / COCH₂Ph | H / CH₃ |
| IX-52 | CH₃ / COOCH₃ | H / CH₃ |
| IX-53 | COCH₃ / H | H / Br |
| IX-54 | COC₂H₅ / H | H / Br |
| IX-55 | COPh / H | H / Br |
| IX-56 | COOCH₃ / H | H / Br |
| IX-57 | COCH₃ / H | H / CH₃ |
| IX-58 | COC₂H₅ / H | H / CH₃ |
| IX-59 | COPh / H | H / CH₃ |
| IX-60 | COOCH₃ / H | H / CH₃ |
| IX-61 | COCl / H | H / H |
| IX-62 | COCH₂OCH₃ / H | H / H |
| IX-63 | COCH₂OC₂H₅ / H | H / H |
| IX-64 | CONH₂ / H | H / H |
| IX-65 | CONHCH₃ / H | H / H |
| IX-66 | CONHC₂H₅ / H | H / H |
| IX-67 | COOH / H | H / H |

The N-(substituted amino)pyrrole derivative of the above formula (I) according to the present invention exhibits a certain herbicidal effect in a low dosage, and has a selectivity between crops and weeds. Accordingly, a herbicidal composition comprising this compound as an active ingredient is suitable, e.g., for controlling monocotyledous and dicotyledous weed in important crops, such as wheat, rice, corn, soybean, cotton, beet, potato and tomato, before or after germination.

Examples of dicotyledous weeds which can be prevented by the herbicidal composition of the present invention include weeds belonging to Amaranthus, Bidens, Stellaria, Abutilon, Convolvulus, Matricaria, Galium, Lindernia, and the like.

Examples of monocotyledous weeds include weeds belonging to Echinochloa, Setaria, Digitaria, Avena, Cyperus, Alisma, Monochoria, and the like.

The herbicidal composition according to the present invention may be applied in areas such as farming areas, inclusive of farms paddy fields and orchards, as well as non-farming areas, inclusive of grounds and industrial sites.

The compound of the present invention can be utilized as is, but it is generally used in various forms of preparations, such as dust, wettable powder, granule, emulsion, etc., together with a preparation adjavant.

In this case, a preparation is prepared so that one or more compounds of the present invention are contained in an amount of 0.1 to 95% by weight, preferably 0.5 to 90% by weight, and particularly 2 to 70% by weight.

Examples of carriers, diluents, and surfactant, which can be used as the preparation adjuvant, include talc, kaolin, bentonite, diatom earth, white carbon, clay, and the like. As liquid diluents, water, xylene, toluene, chlorobenzene, cyclohexane, cyclohexanone, dimethylsulfoxide, dimethylformamide, alcohols, and the like can be exemplified.

Surfactants are preferably used depending upon their effects. Examples of emulsifiers are polyoxyethylene alkylaryl ether, polyoxyethylene sorbitan monolaurate, etc.; examples of dispersants are lignin sulfonates, dibutylnaphthalene sulfonate, etc.; and examples of wetting agents are alkylsulfonates, alkylphenyl sulfonates, etc.

The above-mentioned preparation can be roughly divided into one which is used as is and one which is used by diluting with a diluent such as water. In the latter case, the concentration of the compound of the present invention preferably ranges from 0.001 to 1.0%.

The amount of the compound of the present invention used is in a range of from 0.01 kg to 10 kg, preferably 0.05 to 5 kg, per 1 ha.

Since the concentrations and amounts used vary with the form of preparation, the period of usage, the manners of usage, the sites of the usage, the intended crops, and other factors, these values can, of course, be changed in spite of the above ranges. Moreover, the compound of the present invention can be used in combination with other active ingredients, such as fungitides, bactericides, miticides and herbicides.

EXAMPLES

The present invention will now be described in detail by referring to Synthesis Examples of the N-(substituted amino)pyrrole derivative of the present invention, Preparation Examples and Test Examples thereof. The present invention is not limited to these Synthesis Examples, Preparation Examples and Test Examples thereof unless departing from the scope of the present invention.

Synthesis Example 1

Synthesis of N-(4,6-dimethoxypyrimidin-2-yl)-N'-{[(1H-pyrrol-1-yl)amino]sulfonyl}urea (I-53)

Chlorosulfonyl isocyanate (0.94 g; 6.5×1.02 mM) was dissolved in 10 ml of dichloromethane at −70° C., followed by adding dropwise a solution of 2-amino-4,6-dimethoxypyrimidine (1.0 g; 6.5 mM) in 20 ml of dichloromethane.

Thereafter, the temperature of the reaction mixture was raised to nearly 0° C. over 1 hour to prepare [(4,6-dimethoxypyrimidin-2-yl)ureylenesulfonyl chloride.

After cooling again to −70° C., a solution of 1-aminopyrrole (II-1; 1.0 g; 6.5×2. omM) in 10 ml of dichloromethane was added dropwise.

The mixture was then stirred for 20 hours while the temperature was lowered to room temperature. Thereafter, the solvent in the reaction mixture was distilled at room temperature, and water was added to the resultant residue. The precipitated solid was filtered off and washed with water. The resultant product was recrystallized from a mixture of DMF/water to obtain the target product (I-53). White solid; Yield 1.86 g (83.7%); HPLC purity 96.5% (254 nm); m.p. 153° C. (decomposition)

IR(KBr cm$^{-1}$): 3248 1724 1610 1582 1456 1364 1202 1172

NMR(d$_6$-DMSO, δ): 3.66(6H,s:pyrmidine ring OCH$_3$×2) 5.8(1H,s:pyrimidine ring H) 5.9(2H,t,J=2.3 Hz:pyrrole ring C3 H,C4 H) 6.58(2H,t,J=2.3 Hz:pyrrole ring C2 H,C5 H) 10.4(1H,s:NH) 11.4(1H,bs:NH) 12.0(1H,bs:NH)

MS[DI] m/z: 342(M+,5) 261(26.5) 187(15) 81(100)

Synthesis Example 2

Synthesis of N-(4,6-dimethoxy-2-pyrimidinyl)-N'-{[N"-(1H-pyrrol-1-yl)-N"-methylamino]sulfonyl}urea (I-126)

N-(4,6-dimethoxypyrimidin-2-yl)-N'-{[(1H-pyrrol-1yl)amino]sulfonyl}urea (I-53; 0.2 g; 0.58 mM) synthesized according to Synthesis Example 1 at room temperature was dissolved in 10 ml of dried DMF, followed by adding 60% sodium hydride (0.023 g; 0.58 mM). After addition of a solution of methyl iodide (0.3 g; 0.58 g×3.64 mM) in dried DMF, the mixture was stirred at room temperature for 3 hours.

The reaction mixture was poured into ice-water, which was weakly acidified with diluted hydrochloric acid. The precipitated solid was filtered off and washed with water. The crude product was purified with column chromatography on silica gel to obtain the target product (I-126). White crystal; Yield 0.105 g (25.2%); m.p. 143°–145 °C.; HPLC purity 99.4% (254 nm)

IR(KBr cm$^{-1}$): 1714 1622 1570 1452 1392 1360 1202 1170

NMR(d$_6$-DMSO, δ): 3.36(3H,s:CH$_3$—N—SO$_2$) 3.66(6H, s:pyrimidine ring OCH$_3$×2) 5.82(1H,s:pyrimidine ring H) 5.93(2H,t,J=2.3 Hz:pyrrole ring C3 H,C4 H) 6.80(2H,t,J=2.3 Hz:pyrrole ring C2 H,C5 H) 10.6(1H,bs:NH) 12.5(1H, bs:NH)

MS[DI] m/z: 356(M+,2) 261(14) 201(19) 95(100)

Synthesis Example 3

Synthesis of N-(4,6-dimethoxypyrimidin-2-yl)-N'-{[(2,5-dimethyl-1H-pyrrol-1-yl)amino]sulfonyl}urea (I-187)

Compound (I-187) was synthesized by the same manner as in Synthesis Example 1. Light yellow solid; m.p. 157° C. (decomposition); Yield 32 mg (9.4%); HPLC purity 98.6% (254 nm);

IR (KBr cm$^{-1}$): 3320 2932 1719 1614 1584 1458 1365 1170

NMR(CDCl$_3$, δ): 2.16(6H,s:pyrrole ring CH$_3$×2) 3.73(6H,s:pyrimidine ring OCH$_3$×2) 5.6(2H,s:pyrrole ring C3 and C4) 5.65(1H,s:pyrimidine ring H) 8.16(1H,bs:NH) 8.7~9.4(1H,bs:NH) 12.5(1H,bs:NH)

Synthesis Example 4

Synthesis of N-{[(2-bromo-1H-pyrrol-1-yl)amino]sulfonyl}-N'-(4,6-dimethoxypyrimidin-2-yl)urea (I-321)

N-(4,6-dimethoxypyrimidin-2-yl)-N'-{[(1H-pyrrol-1yl)amino]sulfonyl}urea (I-53; 0.164 g; 0.48 mM) synthesized according to synthesis Example 1 at room temperature was dissolved in 10 ml of tetrahydrofuran. To the solution was added under cooling with ice-water N-bromosuccinimide (0.085 g; 0.48 mM). After cooled for a short period of time, the mixture was stirred at room temperature for 3 hours. The solvent in the reaction mixture was then distilled away and the resultant residue was purified with column chromatography on silica gel to obtain the target product. White solid; m.p. 157° C.; Yield 0.095 g (47.5%)

IR (KBr cm$^{-1}$): 3320 3132 1716 1614 1582 1454 1364 1170

NMR(CDCl$_3$, δ): 3.7(6H,s:pyrimidine ring OCH$_3$×2) 5.6(1H,s:pyrimidine ring H) 6.0(2H,m:pyrrole ring C3 and C4) 6.7~6.9(1H,m:pyrrole ring C5) 8.5(1H,bs:NH) 12.5(1H, bs:NH)

Synthesis Example 5

Synthesis of N-{[(2-acetyl-1H-pyrrol-1-yl)amino]sulfonyl}-N'-(4,6-dimethyl-2-pyrimidinyl)urea (I-413)

Using 2-acetyl-1-aminopyrrole (II-16) synthesized according to the below-mentioned Synthesis Example 18 as a starting material, compound (I-413) was synthesized by nearly the same manner as in Synthesis Example 1. Yellow solid; m.p. 149°–150° C. (decomposition); Yield 89 mg (12.1%); HPLC purity 99.4% (254 nm);

IR (KBr cm$^{-1}$): 3172 3076 1722 1640 1614 1558 1480 1414 1392 1346

NMR(d6-DMSO, δ): 2.1(3H,s:pyrrole ring COCH$_3$) 2.26(6H:pyrimidine ring CH$_3$×2) 6.0(1H,dd,J=3,4 Hz:pyrrole ring C4) 6.86(1H,s:pyrimidine ring H) 6.8–7.0(2H, m:pyrrole ring C3 and C5) 10.4(1H,bs:NH) 11.4–12.6(1H, bs:NH) the others of NH are obscure.

Synthesis Example 6

Synthesis of N-{[(2-acetyl-1H-pyrrol-1yl)amino]sulfonyl}-N'-(4-chloro-6-methyl-2-pyrimidinyl)urea (I-414)

Using 2-acetyl-1-aminopyrrole (II-16) synthesized according to the below-mentioned Synthesis Example 18 as a starting material, compound (I-414) was synthesized by nearly the same manner as in Synthesis Example 1. Yellow solid; m.p. 109°–110° C. (decomposition); Yield 0.69 g (58.0%); HPLC purity 96.6% (254 nm);

IR (KBr cm$^{-1}$): 3164 1736 1588 1474 1416 1306 1174

NMR(d$_6$-DMSO, δ): 2.16(3H,s:pyrrole ring COCH$_3$) 2.3(3H,s:pyrimidine ring CH$_3$) 6.06(1H,dd,J=3,4 Hz:pyrrole ring C4) 6.86–7.08(2H,m:pyrrole ring C3 and C5) 7.18(1H, pyrimidine ring H) 10.6(1H,s:NH) 11.4(1H,bs:NH) the others of NH are obscure.

Synthesis Example 7

Synthesis of N-{[(2-acetyl-1H-pyrrol-1-yl)amino]sulfonyl}-N'-(4-methoxy-6-methyl-2-pyrimidinyl)urea (I-423)

Using 2-acetyl-1-aminopyrrole (II-16) synthesized according to the below-mentioned Synthesis Example 18 as a starting material, compound (I-423) was synthesized by nearly the same manner as in Synthesis Example 1. Yellow solid; m.p. 139°–140° C., 145° C. (decomposition);

Yield 36 mg (3.1%); HPLC purity 96% (220 nm);

IR (KBr cm$^{-1}$): 3200 1746 1624 1578 1464 1412 1386 1376 1356 1182

NMR(d$_6$-DMSO, δ): 2.2(3H,s:pyrrole ring COCH$_3$) 2.12(3H,s:pyrimidine ring CH$_3$) 3.75(3H,s:pyrimidine ring OCH$_3$) 6.05(1H,t,J=4 Hz:pyrrole ring C4) 6.4(1H,s:pyrimidine ring H) 6.8–7.06(2H,m:pyrrole ring C3 and C5) 10.4(1H,bs:NH) the others of NH are obscure.

Synthesis Example 8

Synthesis of N-{[(2-acetyl-1H-pyrrol-1-yl)amino]sulfonyl}-N'-(4,6-dimethoxy-2-pyrimidinyl)urea (I-455)

Using 2-acetyl-1-aminopyrrole (II-16) synthesized according to the below-mentioned Synthesis Example 18 as a starting material, compound (I-455) was synthesized by nearly the same manner as in Synthesis Example 1.

Chlorosulfonyl isocyanate (0.26 g; 1.776×1.05 mM) was dissolved in 5 ml of dichloromethane at −70° C., followed by adding dropwise a solution of 2-amino-4,6-dimethoxypyrimidine (0.273 g; 1.77 mM) in 10 ml of dichloromethane.

Thereafter, the temperature of the reaction mixture was raised to nearly 0° C. over 1 hour. After cooling again the reaction mixture to −70° C., a solution of 2-acetyl-1-aminopyrrole (II-16; 0.44 g; 1.77×2.0 mM) in 5 ml of dichloromethane was added dropwise.

The mixture was then stirred for 20 hours while the temperature was lowered to room temperature. Thereafter, the solvent in the reaction mixture was distilled away, and water was added to the resultant residue. The precipitate was filtered off and washed with water.

The crude product was recrystallized from a mixture of DMF/water to obtain the target product. White solid; Yield 0.53 g (78%); HPLC purity 98.6% (254 nm);

m.p. 168° C. (decomposition)

NMR(d$_6$-DMSO, δ): 2.1(3H,s:COCH$_3$) 3.66(6H, s:pyrimidine ring OCH$_3$×2) 5.8(1H,s:pyrimidine ring H) 6.0(1H, t,J=4 Hz:pyrrole ring C4 H) 6.8–7.0(2H,m:pyrrole ring C3 H, C5 H) 10.3(1H,S:NH) 11.5(1H,bs:NH) 12.3(1H,bs:NH)

MS[DI] m/z: 384(M+,2) 261(1) 229(3) 155(100) 123(15)

Synthesis Example 9

Synthesis of N-{[(2-acetyl-1H-pyrrol-1-yl)amino]sulfonyl}-N'-(4,6-dimethoxy-1,3,5-triazin-2-yl)urea (I-518)

Using 2-acetyl-1-aminopyrrole (II-16) synthesized according to the following Synthesis Example 18 as a starting material, compound (I-518) was synthesized by nearly the same manner as in Synthesis Example 1. Yellow solid; m.p. 161°–164° C. (decomposition); Yield 0.2 g (21.7%); HPLC purity 96.2% (254 nm)

IR (KBr cm$^{-1}$) 3140 1742 1632 1576 1498 1374 1168 818

NMR(d$_6$-DMSO, δ): 2.2(3H,s:pyrrole ring COCH$_3$) 3.8(6H,s:triazine ring OCH$_3$×2) 6.1(1H,t,J=4 Hz:pyrrole ring C4) 6.9–7.1(2H,m:pyrrole ring C3 and C5) 10.9(1H, bs:NH) 11.6(1H,bs:NH) the otehrs of NH are obscure.

Synthesis Example 10

Synthesis of N-{[N''-(2-acetyl-1H-pyrrol-1-yl)-N''-methylamino]sulfonyl}-N'-(4,6-dimethoxy-2-pyrimidinyl)urea (I-528)

Using N-{[(2-acetyl-1H-pyrrol-1-yl)amino]sulfonyl}-N'-(4,6-dimethoxy-2-pyrimidinyl)urea (I-455) synthesized according to the Synthesis Example 8 as a starting material, compound (I-528) was synthesized by nearly the same manner as in Synthesis Example 2. White solid; m.p. 158°–160° C.; Yield 100 mg (36%); HPLC purity 99.1% (254 nm)

IR (KBr cm$^{-1}$): 3148 2952 1718 1668 1616 1578 1458 1364 1164

NMR(d$_6$-DMSO, δ): 2.2(3H,s:COCH3) 3.45(3H, S:NCH3) 3.7(6H,s:pyrimidine ring OCH$_3$×2) 5.85(1H,S: pyrimidine ring H) 6.1(1H,dd,J=3,4 Hz:pyrrole ring C4) 7.0(1H,dd,J=2,4 Hz: pyrrole ring C3 or C5) 7.2(1H,dd,J=2,3 Hz: pyrrole ring C3 or C5) 10.5(1H,s:NH) 12.3(1H,bs:NH)

Synthesis Example 11

Synthesis of N-{[(2-ethylcarbonyl-1H-pyrrol-1-yl)amino]sulfonyl}-N'-(4,6-dimethoxy-2-pyrimidinyl)urea (I-589)

Using 1-amino-2-ethylcarbonylpyrrole (II-17) synthesized according to the below-mentioned Synthesis Example 19 as a starting material, compound (I-589) was synthesized by nearly the same manner as in Synthesis Example 9. Light yellow solid; Yield 0.73 (84.8%); HPLC purity 98.6% (254 nm)

IR (KBr cm$^{-1}$): 3208 3100 2950 1731 1656 1617 1578 1518 1458 1365 1197

NMR(d$_6$-DMSO, δ): 0.83(3H,t,J=7 Hz:COCH$_2$CH$_3$) 2.55(2H,q ,J=7 Hz:COCH$_2$) 3.66(6H,s:pyrimidine ring OCH$_3$×2) 5.8(1H,s:pyrimidine ring H) 6.0(1H,dd,J=3,4 Hz:pyrrole ring C4) 6.9(1H,t,J=2 Hz:pyrrole ring C3 or C5)

Synthesis Example 12

Synthesis of N-(4,6-dimethoxy-2-pyrimidinyl)-N'-{[(2-trifluoroacetyl-1H-pyrrol-1-yl)amino]sulfonyl}urea (I-723)

Using 1-amino-2-trifluoroacetylpyrrole (II-19) synthesized according to the below-mentioned Synthesis Example 21 as a starting material, compound (I-723) was synthesized by nearly the same manner as in Synthesis Example 9. White solid; m.p. 145°–7° C.; Yield 133 mg (28%); HPLC purity 96.6% (254 nm)

IR (KBr $cm^{-1}$): 3270 3170 1726 1682 1616 1362 1200 1170

NMR($d_6$-DMSO, δ): 3.7(6H,s:pyrimidine ring $OCH_3 \times 2$) 5.8(1H,s:pyrimidine ring H) 6.3(1H,dd,J=2.5, 4.0:pyrrole ring C4) 7.05(1H,m:pyrrole ring C3) 7.3–7.5(1H,m:pyrrole ring C5) 10.5(1H,s:NH) 11.8–12.6(1H,bs:NH) the others of NH are obscure.

Synthesis Example 13

Synthesis of N-{[(2-(4-chlorobutyryl)-1H-pyrrol-1-yl)amino]sulfonyl}-N'-(4,6-dimethoxy-2-pyrimidinyl)urea (I-857)

Using 1-amino-2-(4-chlorobutyryl)pyrrole (II-20) synthesized according to the below-mentioned Synthesis Example 22 as a starting material, compound (I-857) was synthesized by nearly the same manner as in Synthesis Example 9. White solid; mp.164°–6° C. (decomposition); Yield 57.7 mg (10.8%); HPLC purity 96.0% (254 nm)

IR (KBr $cm^{-1}$) 3406 1734 1650 1614 1584 1458 1377 1200 1173

NMR ($d_6$-DMSO, δ): 1.8(2H,quintet,J=6 Hz:$COCH_2$—$CH_2$) 2.7(2H,t,J=6 Hz:$CH_2Cl$) 3.5(2H,t,J=6 Hz:$COCH_2$) 3.66(6H,s:pyrimidine ring $OCH_3 \times 2$) 5.8(1H,s:pyrimidine ring H) 6.1(1H,dd,J=3,4 Hz:pyrrole ring C4) 6.9–7.1(2H, m:pyrrole ring C3 and C5) 10.4(1H,s:NH2) 11.5(1H,s:NH) 12.2(1H,bs:NH)

Synthesis Example 14

Synthesis of N-{[(2-cyclopropanecarbonyl-1H-pyrrol-1-yl)amino]sulfonyl}-N'-(4,6-dimethoxy-2-pyrimidinyl)urea (I-991)

Using 1-amino-2-cyclopropanecarbonylpyrrole (II-18) synthesized according to the below-mentioned Synthesis Example 20 as a starting material, compound (I-991) was synthesized by nearly the same manner as in Synthesis Example 9. White solid; Yield 0.45 g (60.3%); HPLC purity 96.8% (254 nm)

IR (KBr $cm^{-1}$): 1725 1620 1578 1458 1425 1365 1200

NMR($d_6$-DMSO, δ): 0.46–0.86(4H,m:cyclopropane ring $CH_2$—$CH_2$) 2.3–2.6(1H:cyclopropane ring CH) 3.7(6H, s:pyrimidine ring $OCH_3 \times 2$) 5.85(1H,s:pyrimidine ring H) 6.1(1H,dd,J=3,4 Hz:pyrrole ring C4) 7.0–7.3(2H,m:pyrrole ring C3 or C5) 10.45(1H,s:NH) 11.4(1H,bs:NH) 12.3(1H,bs:NH)

Synthesis Example 15

Synthesis of N-{[(2-benzoyl-1H-pyrrol-1-yl)amino]sulfonyl}-N'-(4,6-dimethoxy-2-pyrimidinyl)urea (I-1125)

Using 1-amino-2-benzoylpyrrole (II-22) synthesized according to the below-mentioned Synthesis Example 23 as starting material, compound (I-1125) was synthesized by nearly the same manner as in Synthesis Example 9. White solid; Yield 0.47 g (66.2%); HPLC purity 99.3% (254 nm)

IR (KBr $cm^{-1}$): 3208 1725 1617 1578 1515 1455 1368 1200 1179

NMR($d_6$-DMSO, δ): 3.6(6H,s:pyrimidine ring $OCH_3 \times 2$) 5.7(1H,s:pyrimidine ring H) 6.1(1H,dd,J=3,4 Hz:pyrrole ring C4) 6.6(1H,dd,J=2,4 Hz:pyrrole ring C3 or C5) 7.05–7.2(1H,m:pyrrole ring C3 or C5) 7.3–7.6(5H,m:aromatic H) 10.4(1H, s:NH) 11.6(1H,s:NH) 12.4 (1H,bs:NH)

Synthesis Example 16

Synthesis of N-[[[[[(4,6-dimethoxy-2-pyrimidinyl)amino]carbonyl]amino]sulfonyl]amino]pyrrol-2-carboxylic acid methyl ester (I-1259)

Using (1-amino-1H-pyrrol-2-yl)carboxylic acid methyl ester (II-29) synthesized according to the below-mentioned Synthesis Example 25 as a starting material, compound (I-1259) was synthesized by nearly the same manner as in Synthesis Example 9. White solid; m.p. 179°–180° C. (decomposition); Yield 0.31 g (56.2%); HPLC purity 99.1% (254 nm)

IR(KBr $cm^{-1}$): 3236 1720 1694 1618 1454 1366 1196

NMR($d_6$-DMSO, δ): 3.5(3H,s:$COOCH_3$) 3.64(6H,s:pyrimidine ring $OCH_3 \times 2$) 5.8(1H,s:pyrimidine ring H) 6.0(1H, t,J=3.4 Hz:pyrrole ring C4 H) 6.6–6.8(1H,m:pyrrole ring C3 H or C5 H) 6.84–7.0(1H,m:pyrrole ring C3 or C5 H) 10.45(1H,s:NH) 11.58(1H,bs:NH) 12.2(1H,bs:NH)

Synthesis Example 17

Synthesis of N-(4,6-dimethoxy-2-pyrimidinyl)-N'-[[[2-(dimethylcarbamoyl)-1H-pyrrol-1-yl)amino]sulfonylurea (I-1393)

Using 1-amino-2-(dimethylcarbamoyl)pyrrole (II-28) synthesized according to the below-mentioned Synthesis Example 24 as a starting material, compound (I-1393) was synthesized by nearly the same manner as in Synthesis Example 9. White solid; m.p. 150°–152° C.; Yield 30 mg (42%); HPLC purity 90%

IR (KBr $cm^{-1}$): 3132 2948 1720 1698 1614 1584 1456 1362 1198

NMR($d_6$-DMSO, δ): 2.1(3H,s:$CONCH_3$) 2.8(3H, S:$CONCH_3$) 3.66(6H,s:pyrimidine ring $OCH_3 \times 2$) 5.8(1H, s:pyrimidine ring H) 6.1(1H,dd,J=2,4 Hz:pyrrole ring C4) 6.76(1H,dd,J=1.5,4 Hz:pyrrole ring C3 or C5) 7.1(1H,t,J=2 Hz:pyrrole ring C3 or C5) 10.4(1H,S:NH) 11.7(1H,bs:NH) the others of NH are obscure.

Synthesis Example 18

Synthesis of 2-acetyl-1-aminopyrrole (II-16)

(1) Synthesis of N-(2-acetyl-1H-pyrrol-1-yl)phthalimide (IX-16)

To a solution of acetic acid anhydride (0.53 g; 4.7×1.1 mM) in 6 ml of dichloroethylene was added boron trifluoride-diethyl ether complex (1.46 g; 4.7×2.2 mM) at room temperature, and the mixture was stirred for 10 minutes.

To the resultant mixture was added dropwise a solution of N-(1H-pyrrol-1-yl)phthalimide (IX-1; 1 g; 4.7 mM) in 15 ml of dichloroethylene, followed by stirring for 90 minutes.

The reaction mixture was poured into ice-water and stirred after addition of ethyl acetate. After insoluble materials were separated by filtration, an organic phase in the filtrate was separated and washed with a saturated saline solution, followed by drying with anhydrous sodium sulfate. The crude product (1.18 g) obtained by removing the solvent by distillation was dissolved in acetonitrile and purified with column chromatography on silica gel (eluent: n-hexane and then ethyl acetate/n-hexane=1/5). White solid; m.p. 195°–8° C.; Yield 0.62 g (52.1%); HPLC purity 98.9% (254 nm)

IR(KBr cm$^{-1}$): 1802 1750 1652 1430 1394 1298 1240 1074 748 714

NMR(CDCl$_3$, δ): 2.3(3H,s:COCH$_3$) 6.26(1H,t,J=3.4 Hz:pyrrole ring H) 6.8–7.1(2H,m: pyrrole ring H) 7.65–8.0 (4H,m:aromatic H)

(2) Synthesis of 2-acetyl-1-aminopyrrole (II-16)

N-(2-acetyl-1H-pyrrol-1-yl)phthalimide (IX-16; 1.64 g; 6.45 mM) was dissolved in 30 ml of ethanol. To the resultant solution was added 80% hydrazine monohydrate (0.42 g; 6.45×1.05 mM), followed by stirring at room temperature for 10 minutes and then refluxing for further 30 minutes with heat.

After the reaction mixurure was cooled, insoluble materials were removed by filtration and the filtrate was concentrated. To the residue was added ethyl acetate and water, followed by well stirring. An organic phase was then separated and dried with sodium sulfate. The dried organic phase was condensed to dryness, and purified with column chromatography on silica gel to obtain semisolid target product. Yield 0.47 g (58.7%); HPLC purity 94.0% (254 nm)

IR(NaCl cm$^{-1}$): 3336 3232 3128 1644 1410 1340 1076 946 738

NMR(CDCl$_3$, δ) 2.3(3H,s:COCH$_3$) 5.75(2H,bs:NH$_2$) 5.8–5.9(1H,m:pyrrole ring C4 H) 6.6–6.9(2H,m:pyrrole ring C3 H, C5 H)

Synthesis Example 19

Synthesis of 1-amino-2-ethylcarbonylpyrrole (II-17)

Compound (II-17) was synthesized according to nearly the same manner as in (1) and (2) of Synthesis Example 18.
(1) Synthesis of N-(2-ethylcarbonyl-1H-pyrrol-1-yl)phthalimide (IX-17) White solid; m.p. 140°–2° C.; Yield 3.5 g (58.3%); HPLC purity 99.1% (254 nm)

IR (KBr cm$^{-1}$): 1800 1760 1652 1428 1246 1230 882

NMR(CDCl$_3$, δ): 1.0(3H,t,J=7 Hz:COCH$_2$CH$_3$) 2.76(2H, q,J=7 Hz:COCH$_2$) 6.3(1H,dd,J=3,4 Hz:pyrrole ring C4) 6.9(1H,dd,J=2,3 Hz:pyrrole ring C3 or C5) 7.05(1H,dd,J= 2,4 Hz:pyrrole ring C3 or C5) 7.6–8.0(4H,m:aromatic H)
(2) Synthesis of 1-amino-2-ethylcarbonylpyrrole (II-17)

Light yellow liquid; Yield 1.1 g (58.0%); HPLC purity 97.5% (254 nm)

IR (NaCl cm$^{-1}$): 3340 2986 1632 1527 1470 1410 1314 1074 1044

NMR(CDCl$_3$, δ): 1.1(3H,t,J=7 Hz:COCH$_2$CH$_3$) 2.68(2H, q,J=7 Hz:COCH$_2$) 5.85(2H,s:NH$_2$) 5.93(1H,dd,J=2,3 Hz:pyrrole ring C4) 6.7(1H,t,J=2 Hz:pyrrole ring C3 or C5) 6.75–6.93(1H,m:pyrrole ring C3 or C5)

Synthesis Example 20

Synthesis of 1-amino-2-cyclopropanecarbonylpyrrole (II-18)

Compound (II-18) was synthesized according to nearly the same manner as in (1) and (2) of the above-mentioned Synthesis Example 18.
(1) Synthesis of N-(2-cyclopropanecarbonyl-1H-pyrrol-1-yl)phthalimide (IX-18)

Boron trifluoride-diethyl ether complex (10 g; 23.6×3 mM) was dissolved in 80 ml of 1,2-dichloroethane at 25° C., followed by adding dropwise cyclopropanecarbonyl chloride (7.4 g; 23.6×3 mM). After a suspension of N-(1H-pyrrol-1-yl)phthalimide (IX-1; 5 g; 23.6 mM) in 40 ml of 1,2-dichloroethane was added, the mixture was stirred at 25° C. for 18 hours. The reaction mixture was poured into ice-water and insoluble materials were removed by filtration. The 1,2-dichloroethane phase of the filtrate was separated and washed with a saturated saline solution, followed by drying with anhydrous sodium sulfate. After dried, it was concentrated and the resultant residue was purified with column chromatography on silica gel. White solid; m.p. 150°–2° C.; Yield 2.35 g (35.6%); HPLC purity 92% (254 nm)

IR (KBr cm$^{-1}$): 1803 1752 1647 1431 1398 1275 1236 1071 975 708

NMR(CDCl$_3$, δ): 0.66–1.28(4H,m:cyclopropane ring CH$_2$—CH$_2$) 2.16–2.5(1H,m:cyclopropane ring CH) 6.3(1H, dd,J=3,4 Hz:pyrrole ring C4) 6.9(1H,dd,J=2,3 Hz:pyrrole ring C3 or C5) 7.2(1H,dd,J=2,4 Hz:pyrrole ring C3 or C5) 7.5–8.0(4H,m:aromatic H)
(2) Synthesis of 1-amino-2-cyclopropanecarbonylpyrrole (II-18)

Compound (II-18) was synthesized according to nearly the same manner as in (2) of the above-mentioned Synthesis Example 18. Light yellow liquid; Yield 0.9 g (82%); HPLC purity 93.1% (254 nm)

IR (NaCl cm$^{-1}$): 3334 3232 3016 1629 1527 1473 1413 1242 1050 978 732

NMR(CDCl$_3$, δ): 0.63–1.3(4H,m:cyclopropane ring CH$_2$—CH$_2$) 2.1–2.5(1H:cyclopropane ring CH) 5.7(2H, s:NH$_2$) 6.0(1H,t,J=3 Hz :pyrrole ring C4) 6.8–7.0(2H,m:pyrrole ring C3 or C5)

Synthesis Example 21

Synthesis of 1-amino-2-trifluoroacetylpyrrole (II-19)

Compound (II-19) was synthesized according to nearly the same manner as in (1) and (2) of the above-mentioned Synthesis Example 18.
(1) Synthesis of N-(2-trifluoroacetyl-1H-pyrrol-1-yl)phthalimide (IX-19) White solid; m.p. 118°–120° C.; Yield 1.25 g (17.2%); HPLC purity 99.1% (254 nm)

IR (KBr cm$^{-1}$): 1798 1756 1682 1430 1320 1260 1242 1212 1188 1158 1080 928 752

NMR(CDCl$_3$, δ): 6.4(1H,dd,J=3,4 Hz:pyrrole ring C4) 7.1(1H,dd,J=1.5,3.0 Hz:pyrrole ring C3) 7.3(1H,dd,J=1.5, 4.0 Hz:pyrrole ring C5) 7.58–7.9(4H,m:aromatic H)
(2) Synthesis of 1-amino-2-trifluoroacetylpyrrole (II-19) Light yellow solid; m.p. 33°–35° C.; Yield 0.847 g (42.3%); HPLC purity 97.6% (254 nm)

IR (KBr cm$^{-1}$): 3364 3148 1660 1532 1418 1274 1152 1086 922 740

NMR(CDCl$_3$, δ): 5.6(2H,bs:NH$_2$) 6.05(1H,dd,J=3,4 Hz:pyrrole ring C4) 6.9–7.3(2H,m:pyrrole ring C3,C5)

Synthesis Example 22

Synthesis of 1-amino-2-(4-chlorobutyryl)pyrrole (II-20)

Compound (II-20) was synthesized according to nearly the same manner as in (1) and (2) of the above-mentioned Synthesis Example 20.
(1) Synthesis of N-[2-(4-chlorobutyryl)-1H-pyrrol-1-yl]phthalimide (IX-20) White solid; m.p. 126°–8° C.; Yield 3.26 g (54%); HPLC purity 97.4% (254 nm)

IR (KBr cm$^{-1}$): 1800 1750 1666 1430 1394 1268 1066 884 708

NMR(CDCl$_3$, δ): 2.1(2H,quintet,J=6 Hz:COCH$_2$—CH$_2$) 2.9(2H,t,J=6 Hz:CH$_2$Cl) 3.43(2H,t,J=6 Hz: COCH$_2$) 6.26(1H,dd,J=3,4 Hz:pyrrole ring C4) 6.8(1H,dd,J=2,3 Hz:pyrrole ring C3 or C5) 6.96–7.15(1H,m:pyrrole ring C3 or C5) 7.5–8.0(4H,m:aromatic H)
(2) Synthesis of 1-amino-2-(4-chlorobutyryl)pyrrole (II-20) Light yellow liquid; Yield 0.31 g (16%); HPLC purity 80.6% (254 nm)

IR (NaCl cm$^{-1}$): 2972 1718 1640 1414 738
NMR(CDCl$_3$, δ): 2.1(2H,quintet,J=6 Hz:COCH$_2$—CH$_2$) 2.9(2H,t,J=6 Hz:CH$_2$Cl) 3.5(2H,t,J=6 Hz:COCH$_2$) 6.0(1H, dd,J=3,4 Hz:pyrrole ring C4) 6.7~6.9(2H,m:pyrrole ring C3 and C5) 7.1(2H,s:NH$_2$)

Synthesis Example 23

Synthesis of 1-amino-2-benzoylpyrrole (II-22)

Compound (II-22) was synthesized according to nearly the same manner as in (1) and (2) of the above-mentioned Synthesis Example 20.
(1) Synthesis of N-(2-benzoyl-1H-pyrrol-1-yl)phthalimide (IX-22) White solid; m.p. 137°–140° C.; Yield 1.6 g (21%); HPLC purity 92% (254 nm)

IR (KBr cm$^{-1}$): 1800 1748 1636 1422 1364 1242
NMR(CDCl$_3$, δ): 6.28(1H,dd,J=3,4 Hz:pyrrole ring C4) 6.8(1H,dd,J=2,4 Hz:pyrrole ring C3 or c5) 7.0(1H,dd,J=2,3, Hz:pyrrole ring C3 or C5) 7.16~7.48(3H,m:aromatic H) 7.48~8(6H,m:aromatic H)
(2) Synthesis of 1-amino-2-benzoylpyrrole (II-22) White solid; m.p. 60°–3° C.; Yield 0.62 g (75.6%)

IR (KBr cm$^{-1}$): 3346 1626 1473 1353 1074 1026 912 723
NMR (CDCl$_3$, δ): 5.8(2H,bs:NH$_2$) 5.9(1H,dd,J=3,4 Hz:pyrrole ring C4) 6.5(1H,dd,J=2,4 Hz:pyrrole ring C3 or c5) 6.9(1H,t,J=2 Hz:pyrrole ring C3 or C5) 7.0~7.5(3H, m:aromatic H) 7.5~7.8(2H,m:aromatic H)

Synthesis Example 24

Synthesis of 1-amino-2-(dimethylcarbamoyl)pyrrole (II-28)
(1) Synthesis of N-[2-(dimethylcarbamoyl)-1H-pyrrol-1-yl] phthalimide (IX-28)

A suspension of anhydrous aluminium chloride (12.6 g; 18.8×5 mM) in 80 ml of 1,2-dichloroethane was cooled with ice to 0°–5° C., and oxalyl chloride (12 g; 18.8×5 mM) was added dropwise to the suspension. After stirred at 0°–5° C. for 20 minutes, a suspension of N-(1H-pyrrol-1-yl)phthalimide (IX-I; 4.0 g; 18.8 mM) in 30 ml of 1,2-dichloroethane was added thereto. Thereafter, the mixture was stirred for 50 minutes with slowly raising the temperature to room temperature. The reaction mixture was poured into ice water and insoluble materials was removed by filteration. The filtrate was concentrated and the residue was dissolved again in 30 ml of 1,2-dichloroethane. To the solution was added little by little a suspension dimethylamine hydrochloride (3 g; 18.8×2 mM) and triethylamine (7.82 g; 18.8×4.1 mM) in 1,2-dichloroethane. The mixture was then stirred at room temperature for 2 hours, followed by pouring the reaction mixture into ice water. After neutralizing with diluted hydrochloric acid, the 1,2-dichloroethane phase was separated. The resultant organic phase was washed with saturated saline solution and dried with anhydrous sodium sulfate, followed by concentrated. The resulted residue was purified with column chromatography on silica gel. Light yellow solid; m.p. 153°–155° C.; Yield 0.845 g (16%); HPLC purity 94% (254 nm)

IR (KBr cm$^{-1}$): 1798 1754 1658 1408 1380 1288 708
NMR(CDCl$_3$, δ): 2.8(3H,s:pyrrole ring CONCH$_3$) 2.9(3H,s:pyrrole ring CONCH$_3$) 6.3(1H,dd,J=2.5,4 Hz:pyrrole ring C4) 6.9–7.1(2H,m:pyrrole ring C3,C5) 7.6–7.9(4H, m:phthalimide ring H)
(2) Synthesis of 1-amino-2-(dimethylcarbamoyl)pyrrole (II-28)

Compound (II-28) was synthesized according to nearly the same manner as in (2) of Synthesis Example 18. Light yellow liquid; Yield 0.33 g (71.7%) (For measurement of IR and NMR, that of HPLC purity 93% (254 nm) was used.)

IR (NaCl film cm$^{-1}$): 3352 3132 2940 1632 1400 1150 1074 980 738
NMR(CDCl$_3$, δ): 2.95(3H,s:CONCH$_3$) 3.0(3H, s:CONCH$_3$) 5.7 (2H,bs:NH$_2$) 6.0(1H,dd,J=2.5,4 Hz:pyrrole ring C4) 6.7(1H,dd,J=2,4 Hz:pyrrole ring C3 or C5) 7.0(1H, t,J=2 Hz:C3 or C5)

Synthesis Example 25

Synthesis of (1-amino-1H-pyrrol-2-yl)carboxylic acid methyl ester (II-29)
(1) Synthesis of N-(2-chlorocarbonyl-1H-pyrrol-1-yl)phthalimide (IX-61)

A suspension of anhydrous aluminium chloride (3.1 g; 4.7×5 mM) in 20 ml of 1,2-dichloroethane was cooled with ice to 0°–5° C., and oxalyl chloride (3 g; 4.7×5 mM) was added dropwise to the suspension. After stirred at 0°–5° C. for 20 minutes, a suspension of N-(1H-pyrrol-1-yl)phthalimide (IX-I; 1.0 g; 4.7 mM) in 1,2-dichloroethane was added thereto. Thereafter, the mixture was stirred for 50 minutes with slowly raising the temperature to room temperature. The reaction mixture was poured into ice water and insoluble materials was removed by filteration. To the filtrate was added ethyl acetate with thoroughly stirring to separate an organic phase. The organic phase was dried with sodium sulfate, and the solvent was then removed by distillation to obtain the compound (IX-61)
(2) Synthesis of N-(2-methoxycarbonyl-1H-pyrrol-1-yl)phthalimide (IX-29)

The compound (IX-61) was refluxed in methanol for 1 hours and the solvent was then removed by distillation. The resultant residue was purified with column chromatography on silica gel to obtain the compound (IX-29) White solid; m.p. 158°–160° C.; Yield 0.29 g (23%); HPLC purity 99.5% (254 nm)

IR(KBr cm$^{-1}$): 1800 1750 1694 1450 1300 1242 710
NMR(d$_6$-DMSO, δ): 3.5(3H,s:COOCH$_3$) 6.3(1H,t,J=3.4 Hz:pyrrole ring C4 H) 6.98(1H,dd,J=1.5,3.4 Hz:pyrrole ring C3 H) 7.3~7.4(1H,m:pyrrole ring C5 H) 7.9(4H,S:aromatic H)
(3) Synthesis of (1-amino-1H-pyrrol-2-yl)carboxylic acid methyl ester (II-29)

The compound (II-29) was synthesized according to nearly the same manner as in (2) of the above-mentioned Synthesis Example 18. Light yellow oil; Yield 0.389 g (86.8%); HPLC purity 99.6% (254 nm)

IR(NaCl cm$^{-1}$): 3320 3210 2950 1694 1250 1100 1017 740
NMR(CDCl$_3$, δ): 3.68(3H,S:COOCH3) 5.4(2H,bs:NH2) 5.85(1H,dd,J=3.0,4.0 Hz: pyrrole ring C4 H) 6.5~6.86(2H, m:pyrrole ring C3 H, C5 H)

Reference Synthesis Example 1

Synthesis of 1-aminopyrrole (II-1)

N-(1H-pyrrol-1-yl)phthalimide (IX-I; 10 g; 61.6 mM) was dissolved in 80 ml of methanol. To the resultant solution was added 80% hydrazine monohydrate (61.6×1.1 mM), and the mixture was stirred at room temperature for minutes. It is further refluxed for 30 minutes with heat.

After the reaction mixture was cooled, 1.4 ml of acetic acid was added with stirring. Thereafter, insoluble materials were removed by filtration and the filtrate was cocentrated. To The resultant residue was added a 5% aqueous sodium hydroxide solution to change into an alkalinity. After the mixture was extracted with ethyl ether, the resultant extract was washed with a saturated saline solution and dried with sodium sulfate. The solvent was removed by filtration to obtain the compound (II-1) by filtration. b.p. 72°–3° C./16 mmHg (lit. 71°–3° C./12 mmHg); HPLC purity 99.7% (220 nm); Yield 1.64 g (32.4%)

IR(NaCl film cm$^{-1}$): 3348 3220 3140 1630 1492 1292 1084 1062 718

NMR(CDCl$_3$, δ): 4.6(2H,bs;NH$_2$) 5.96(2H,t,J=2 Hz;3-position-H,4-position-H) 6.56(2H,t,J=2 Hz;2-position-H,5-position-H)

Formulation Examples and Test Examples will hereinafter be described. It should be borne in mind that the vehicles (diluents), adjuvants, their mixing ratio and effective components can vary in wide ranges respectively. In these examples, all "parts" are by weight.

| Formulation Example 1 (Wettable Powder) | |
|---|---|
| Compound (I-455) | 50 parts |
| A salt of ligninsulfonic acid | 5 parts |
| A salt of alkylsulfonic acid | 3 parts |
| Diatomaceous earth | 42 parts |

The above ingredients are mixed and ground into a wettable powder. For application, it is diluted with water.

| Formulation Example 2 (Emulsion) | |
|---|---|
| Compound (I-1125) | 25 parts |
| Xylene | 65 parts |
| Polyoxyethylene alkylaryl ether | 10 parts |

The above ingredients are mixed intimately into an emulsion. For application, it is diluted with water.

| Formulation Example 3 (Granule) | |
|---|---|
| Compound (I-991) | 8 parts |
| Bentonite | 40 parts |
| Clay | 45 parts |
| Ligninsulfonic acid | 7 parts |

The above ingredients are mixed intimately. After the addition of water, the mixture was kneaded and then formed into granules by an extruding granulator.

Test 1 Test on herbicidal activity by seed treatment

Two sheets of filter paper were placed in a superposed relation in each of Petri dishes having a diameter of 9 cm. Water suspension of each test compound (concentration of the active ingredient: 50 ppm) were separately poured in an amount of 6 ml per dish. Seeds of *Amaranthus retroflexus, Bidens pilosa, Solanum nigrum, Matricaria chamomilla, Setaria viridis, Echinochloa oryzicola*, and *Cyperus iria* were placed at a rate of 10 seeds per dish in the Petri dishes. They were thereafter allowed to germinate in a green house at 28° C. Fourteen days later after placement in the dishes, the degrees of germination and growth inhibition were observed visually. The observation results were ranked in accordance with the below-described 3-stage system. The results are summarized in Table 7.

Growth inhibition rate 1: less than 30%; 2: 30% to less than 70%; 3: 70% or more

TABLE 7

| Compound No. | Concentration (ppm) | A.r. | B.p. | S.n. | M.c. | S.v. | E.o. | C.i. |
|---|---|---|---|---|---|---|---|---|
| I-413 | 50 | 3 | 3 | 3 | 3 | 2 | 2 | 3 |
| I-414 | 50 | 3 | 3 | 3 | 3 | 2 | 2 | 3 |
| I-423 | 50 | 3 | 3 | 3 | 3 | 3 | 3 | 3 |
| I-455 | 50 | 3 | 3 | 3 | 3 | 3 | 3 | 3 |
| I-518 | 50 | 3 | 3 | 3 | 3 | 3 | 3 | 3 |
| I-528 | 50 | 3 | 3 | 3 | 3 | 3 | 3 | 3 |
| I-589 | 50 | 3 | 3 | 3 | 3 | 3 | 3 | 3 |
| I-723 | 50 | 3 | 3 | 3 | 3 | 3 | 3 | 3 |
| I-857 | 50 | 3 | 3 | 3 | 3 | 3 | 3 | 3 |
| I-991 | 50 | 3 | 3 | 3 | 3 | 3 | 3 | 3 |
| I-1125 | 50 | 3 | 3 | 3 | 3 | 2 | 2 | 3 |
| I-1259 | 50 | 3 | 3 | 3 | 3 | 2 | 2 | 3 |
| I-1393 | 50 | 3 | 3 | 3 | 3 | 2 | 2 | 3 |

A.r.: *Amaranthus retroflexus*
B.p.: *Bidens pilosa*
S.n.: *Solanum nigrum*
M.c.: *Matricaria chamomilla*
S.v.: *Setaria viridis*
E.o.: *Echinochloa oryzicola*
C.i.: *Cyperus iria*

Test 2 Test on herbicidal activity by foliar application

Herbicidal solutions of each test compound, which had been prepared by dissolving at predetermined concentrations such as wettable powder of the test compound as that described in the above formulation example, and sprayed at a dosage of 1000 g/ha over foliar parts of *Amaranthus retroflexus, Bidenes pilosa, Sinapis arvensis, Stellaria media, Cassia obtusifolia, Solanum nigrum, Abutilon theophrasti, Convolvulus arvensis, Matricaria chamomilla, Galium aparine, Veronica hederaeforia, Setaria viridis, Echinochloa frumentaceum, Avena fatua, Digitaria adscendens*(which had been allowed to grow individually to 1–2 leaf stage). Fourteen days later after spraying of the test compound, its herbicidal activity was evaluated in accordance with the below-described 3-stage system. The results are summarized in Table 8.

Growth inhibition rate 1: less than 30%; 2: 30% to less than 70%; 3: 70% or more

TABLE 8

| Compound No. | Applicaton Dosage (g/ha) | A.r. | B.p. | S.a. | S.m. | C.o. | S.n. | A.t. | C.a. |
|---|---|---|---|---|---|---|---|---|---|
| I-53 | 1000 | 3 | 3 | 3 | 3 | 2 | 3 | 3 | 3 |
| I-126 | 1000 | 2 | 3 | 3 | 3 | 2 | 2 | 3 | 3 |
| I-187 | 1000 | 3 | 3 | 3 | 2 | 2 | 2 | 3 | 2 |
| I-321 | 1000 | 3 | 3 | 3 | 3 | 2 | 2 | 3 | 2 |
| I-413 | 1000 | 3 | 3 | 3 | 3 | 3 | 3 | 3 | 3 |
| I-414 | 1000 | 3 | 3 | 3 | 3 | 3 | 3 | 3 | 3 |
| I-423 | 1000 | 3 | 3 | 3 | 3 | 3 | 3 | 3 | 3 |
| I-455 | 1000 | 3 | 3 | 3 | 3 | 3 | 3 | 3 | 3 |
| I-518 | 1000 | 3 | 3 | 3 | 3 | 3 | 3 | 3 | 3 |
| I-528 | 1000 | 3 | 3 | 3 | 3 | 3 | 3 | 3 | 3 |
| I-589 | 1000 | 3 | 3 | 3 | 3 | 3 | 3 | 3 | 3 |
| I-723 | 1000 | 3 | 3 | 3 | 3 | 3 | 3 | 3 | 3 |
| I-857 | 1000 | 3 | 3 | 3 | 3 | 3 | 3 | 3 | 3 |
| I-991 | 1000 | 3 | 3 | 3 | 3 | 3 | 3 | 3 | 3 |
| I-1125 | 1000 | 3 | 3 | 3 | 3 | 3 | 3 | 3 | 3 |
| I-1259 | 1000 | 3 | 3 | 3 | 3 | 3 | 3 | 3 | 3 |
| I-1393 | 1000 | 3 | 3 | 3 | 3 | 3 | 3 | 3 | 3 |

TABLE 8-continued

| Compound No. | Application Dosage (g/ha) | M.c. | G.a. | V.h. | S.v. | E.f. | A.f. | D.a |
|---|---|---|---|---|---|---|---|---|
| I-53 | 1000 | 2 | 3 | 3 | 2 | 2 | 2 | 2 |
| I-126 | 1000 | 2 | 3 | 3 | 2 | 2 | 2 | 2 |
| I-187 | 1000 | 2 | 3 | 2 | 3 | 2 | 2 | 2 |
| I-321 | 1000 | 2 | 2 | 3 | 2 | 2 | 2 | 2 |
| I-413 | 1000 | 3 | 3 | 3 | 3 | 2 | 2 | 2 |
| I-414 | 1000 | 3 | 3 | 3 | 3 | 2 | 2 | 2 |
| I-423 | 1000 | 3 | 3 | 3 | 3 | 3 | 3 | 3 |
| I-455 | 1000 | 3 | 3 | 3 | 3 | 3 | 3 | 3 |
| I-518 | 1000 | 3 | 3 | 3 | 3 | 3 | 3 | 3 |
| I-528 | 1000 | 3 | 3 | 3 | 3 | 3 | 3 | 3 |
| I-589 | 1000 | 3 | 3 | 3 | 3 | 3 | 3 | 3 |
| I-723 | 1000 | 3 | 3 | 3 | 3 | 3 | 3 | 3 |
| I-857 | 1000 | 3 | 3 | 3 | 3 | 3 | 3 | 3 |
| I-991 | 1000 | 3 | 3 | 3 | 3 | 3 | 3 | 3 |
| I-1125 | 1000 | 3 | 3 | 3 | 3 | 3 | 2 | 2 |
| I-1259 | 1000 | 3 | 3 | 3 | 3 | 3 | 3 | 2 |
| I-1393 | 1000 | 3 | 3 | 2 | 3 | 3 | 3 | 2 |

A.r.: *Amaranthus retroflexus*
B.p.: *Bindes pilosa*
S.a.: *Sinapis arvensis*
S.m.: *Stellaria meida*
C.o.: *Cassia obtusifolia*
S.n.: *Solanum nigrum*
A.t.: *Abutilon theophrasti*
C.a.: *Convolvulus arvensis*
M.c.: *Matricaria chamomilla*
G.a.: *Galium aparine*
V.h.: *Veronica hederaeforia*
S.v.: *setaria viridis*
E.f.: *Echinochloa frumentaceum*
A.f.: *Avena fatua*
D.a.: *Digitaria adscendens*

What is claimed is:

1. An N-(substituted amino)pyrrole derivative represented by the formula (I):

$$
\begin{array}{c}
R^2 \\
R^3 \\
R^4 \\
R^5
\end{array}
\quad N-N-SO_2NHCONH- \underset{R^6}{\underset{|}{\phantom{N}}} \quad
\begin{array}{c}
N = \\ Z \\ N =
\end{array}
\begin{array}{c}
X^1 \\ \\ X^2
\end{array}
\quad (I)
$$

wherein $R^2$, $R^3$, $R^4$ and $R^5$ is independently hydrogen atom, halogen atom, $C_1-C_4$ alkyl group, $C_1-C_5$ haloalkyl group, $C_2-C_5$ alkoxyalkyl group, $C_3-C_5$ alkenyl group, $C_3-C_5$ haloalkenyl group, $C_3-C_5$ alkinyl group, phenyl group which may be substituted with 1–3 halogen atoms and/or $C_1-C_4$ alkyl groups, $C_7-C_9$ aralkyl group which may be substituted with 1–3 halogen atoms and/or $C_1-C_4$ alkyl groups, $(C_1-C_4$ alkyl)carbonyl group, $(C_2-C_5$ alkoxyalkyl)carbonyl group, $(C_3-C_6$ cycloalkyl)carbonyl group, $(C_1-C_4$ haloalkyl)carbonyl group, $(C_3-C_5$ alkenyl)carbonyl group, benzoyl group which may be substituted with 1–3 halogen atoms and/or $C_1-C_4$ alkyl groups, $(C_7-C_9$ aralkyl)carbonyl group which may be substituted with 1–3 halogen atoms and/or $C_1-C_4$ alkyl groups, carbamoyl group, N-($C_1-C_4$ alkyl)aminocarbonyl group, N,N-[(di-$C_1-C_4$ alkyl)amino]carbonyl group, carboxyl group, ($C_1-C_4$ alkoxy)carbonyl group, ($C_1-C_4$ haloalkoxy)carbonyl group, ($C_2-C_5$ alkoxyalkoxy)carbonyl group, ($C_3-C_5$ alkenyloxy)carbonyl group, ($C_3-C_5$ haloalkenyloxy)carbonyl group or ($C_3-C_5$ alkynyloxy)carbonyl group;

$R^6$ is hydrogen atom, $C_1-C_5$ alkyl group, $C_1-C_5$ haloalkyl group, $C_2-C_5$ alkoxyalkyl group, $C_3-C_5$ alkenyl group, $C_3-C_5$ haloalkenyl group, $C_3-C_5$ alkynyl group or $C_7-C_9$ aralkyl group which may be substituted with 1–3 halogen atoms and/or $C_1-C_4$ alkyl groups;

$X^1$ and $X^2$ are independently hydrogen atom, halogen atom, $C_1-C_4$ alkyl group, $C_1-C_4$ alkoxy group, $C_1-C_4$ alkylthio group, $C_1-C_4$ haloalkyl group, $C_1-C_4$ haloalkoxy group, $C_1-C_4$ haloalkylthio group, $C_2-C_4$ alkoxyalkyl group, $C_2-C_4$ thioalkoxyalkyl group or $NR^7R^8$ wherein $R^7$ and $R^8$ are independently hydrogen atom, $C_1-C_4$ alkyl group or $C_1-C_4$ alkoxy group; and Z is nitrogen atom.

2. An N-(substituted amino)pyrrole derivative of claim 1, wherein $X^1$ and $X^2$ are independently halogen, $C_1-C_2$ alkyl, ethoxy, i-propoxy, methoxy, sec-butoxy, $C_1-C_2$ fluoroalkyl, $C_1-C_2$ fluoroalkoxy, $C_2-C_4$ alkoxyalkyl or $NR^7R^8$, wherein $R^7$ and $R^8$ are independently hydrogen or $C_1-C_2$ alkyl.

3. An N-(substituted amino) pyrrole derivative of claim 1, wherein $R^6$ is hydrogen, methyl, ethyl, i-propyl, n-butyl, 2,2,2-trifluoroethyl, 3-methoxypropyl, crotyl, propargyl, 3,3-dichloroallyl, benzyl, 4-chlorobenzyl or 4-methylbenzyl.

4. An N-(substituted amino)pyrrole derivative of claim 1, wherein $R^3$, $R^4$ and $R^5$ are hydrogens, $R^2$, $R^4$ and $R^5$ are hydrogens or $R^3$ and $R^4$ are hydrogens.

5. An N-(substituted amino)pyrrole derivative of claim 1, wherein $R^3$, $R^4$ and $R^5$ are hydrogens, $R^2$, $R^4$ and $R^5$ are hydrogens or $R^3$ and $R^4$ are hydrogens; $R^6$ is hydrogen, methyl, ethyl, i-propyl, n-butyl, 2,2,2-trifluoroethyl, 3-methoxypropyl, crotyl, propargyl, 3,3-dichloroallyl, benzyl, 4-chlorobenzyl or 4-methoxybenzyl, $X^1$ and $X^2$ are independently halogen, $C_1-C_2$ alkyl, ethoxy, i-propoxy, methoxy, sec-butoxy, $C_1-C_2$ fluoroalkyl, $C_1-C_2$ fluoroalkoxy, $C_2-C_4$ alkoxyalkyl or $NR^7 R^8$, wherein $R^7$ and $R^8$ are independently hydrogen or $C_1-C_2$ alkyl.

6. An N-(substituted amino) pyrrole derivative of claim 1, wherein $R^3$, $R^4$ and $R^5$ are hydrogens and $R^2$ is hydrogen, bromine, methyl, acetyl, propionyl, cyclopropanecarbonyl, trifluoroacetyl, 4-chlorobutyryl, benzoyl, dimethylcarbamoyl or methoxycarbonyl; or $R^2$ and $R^5$ are methyls and $R^3$ and $R^4$ are hydrogens; $R^6$ is hydrogen or methyl; $X^1$ and $X^2$ are independently chlorine, methyl or methoxy.

7. A herbicidal composition which comprises a herbicidally effective amount of an N-(substituted amino)-pyrrole derivative of claim 1 and an agronomically-acceptable carrier or diluent.

* * * * *